US009528993B2

(12) United States Patent
Zhou et al.

(10) Patent No.: US 9,528,993 B2
(45) **Date of Patent: *Dec. 27, 2016**

(54) AGENTS AND METHODS RELATED TO SCREENING FOR RESISTANCE TO DR5 AND REDUCING RESISTANCE TO DR5 AGONISTS

(71) Applicant: The UAB Research Foundation, Birmingham, AL (US)

(72) Inventors: Tong Zhou, Birmingham, AL (US); Robert P. Kimberly, Birmingham, AL (US)

(73) Assignee: The UAB Research Foundation, Birmingham, AL (US)

( * ) Notice: Subject to any disclaimer, the term of this patent is extended or adjusted under 35 U.S.C. 154(b) by 65 days.

This patent is subject to a terminal disclaimer.

(21) Appl. No.: 13/907,035

(22) Filed: May 31, 2013

(65) Prior Publication Data

US 2013/0324433 A1 Dec. 5, 2013

Related U.S. Application Data

(62) Division of application No. 13/356,739, filed on Jan. 24, 2012, now Pat. No. 8,476,030, which is a division (Continued)

(51) Int. Cl.

*G01N 33/566* (2006.01)
*A61K 39/395* (2006.01)

(Continued)

(52) U.S. Cl.

CPC ... *G01N 33/57492* (2013.01); *A61K 39/39558* (2013.01); *C07K 16/2878* (2013.01);

(Continued)

(58) Field of Classification Search

None

See application file for complete search history.

(56) References Cited

U.S. PATENT DOCUMENTS 6,072,047 A 6/2000 Rauch
6,252,050 B1 6/2001 Ashkenazi et al.
6,294,546 B1 9/2001 Rosen et al.
6,313,269 B1 11/2001 Deen et al.
6,342,363 B1 1/2002 Ni et al.

(Continued)

FOREIGN PATENT DOCUMENTS

WO WO9832856 7/1998
WO WO9841629 9/1998

(Continued)

OTHER PUBLICATIONS

Kovacsovics et al., Overexpression of Helicard, a CARD-containing helicase cleaved during apoptosis, accelerates DNA degradation, Current Biol. 12(10): 838-43, May 14, 2002.*

(Continued)

*Primary Examiner* — Claire Kaufman

(74) *Attorney, Agent, or Firm* — Kilpatrick Townsend & Stockton, LLP

(57) ABSTRACT

Provided herein is a method of reversing or preventing a target cell's resistance to a death receptor agonist. Also provided are methods of screening for biomarkers resistance of and monitoring resistance to death receptor agonists. Also provided are methods of selectively inducing apoptosis in a target cell, treating a subject with cancer, autoimmune or inflammatory diseases, comprising administering compositions provided herein. Further provided are compositions comprising agents that modulate CARD containing proteins.

10 Claims, 22 Drawing Sheets

Binding cIAP1

ND1 DDX3: 50-662 aa CARD +

ND2 DDX3: 100-662 aa —

ND3 DDX3: 150-662 aa —

CD5 DDX3: 1-350 aa CARD +

FL DDX3: 1-662 aa CARD +

Related U.S. Application Data of application No. 11/814,551, filed as application No. PCT/US2006/003503 on Jan. 31, 2006, now Pat. No. 8,129,124.

(60) Provisional application No. 60/649,437, filed on Feb. 2, 2005.

(51) Int. Cl.

| | |
|---|---|
| ***G01N 33/574*** | (2006.01) |
| ***C07K 16/28*** | (2006.01) |
| ***C07K 16/40*** | (2006.01) |
| ***G01N 33/68*** | (2006.01) |
| ***C12Q 1/68*** | (2006.01) |
| *C07K 14/715* | (2006.01) |
| *A61K 39/00* | (2006.01) |

(52) U.S. Cl.

CPC ............ *C07K 16/40* (2013.01); *C12Q 1/6886* (2013.01); *G01N 33/574* (2013.01); *G01N 33/6863* (2013.01); *A61K 2039/505* (2013.01); *C07K 2317/34* (2013.01); *G01N 2333/70578* (2013.01); *G01N 2333/7151* (2013.01); *G01N 2333/914* (2013.01); *G01N 2500/02* (2013.01); *G01N 2800/44* (2013.01)

(56) References Cited

U.S. PATENT DOCUMENTS

| | | | |
|---|---|---|---|
| 6,342,369 | B1 | 1/2002 | Ashkenazi |
| 6,433,147 | B1 | 8/2002 | Ni et al. |
| 6,461,823 | B1 | 10/2002 | Ni et al. |
| 6,482,938 | B1 | 11/2002 | Hayashizaki et al. |
| 6,534,061 | B1 | 3/2003 | Goddard et al. |
| 6,635,482 | B1 | 10/2003 | Yu et al. |
| 6,872,568 | B1 | 3/2005 | Ni et al. |
| 7,105,640 | B2 | 9/2006 | Desnoyers et al. |
| 2002/0072091 | A1 | 6/2002 | Ni et al. |
| 2002/0098550 | A1 | 7/2002 | Ni et al. |
| 2003/0133932 | A1 | 7/2003 | Zhou et al. |
| 2003/0198637 | A1 | 10/2003 | Zhou et al. |
| 2003/0228309 | A1 | 12/2003 | Salcedo et al. |

FOREIGN PATENT DOCUMENTS

| | | |
|---|---|---|
| WO | WO9846643 | 10/1998 |
| WO | WO9851793 | 11/1998 |
| WO | WO9902544 | 1/1999 |
| WO | WO9902653 | 1/1999 |
| WO | WO9903992 | 1/1999 |
| WO | WO9909165 | 2/1999 |
| WO | WO9911791 | 3/1999 |
| WO | WO9912963 | 3/1999 |
| WO | WO9937684 | 7/1999 |
| WO | 99/40102 | 8/1999 |
| WO | WO0066156 | 11/2000 |
| WO | WO0067793 | 11/2000 |
| WO | WO0073349 | 12/2000 |
| WO | WO0075191 | 12/2000 |
| WO | WO0119861 | 3/2001 |
| WO | WO0177342 | 10/2001 |
| WO | WO0183560 | 11/2001 |
| WO | WO02079377 | 10/2002 |
| WO | 03038043 | 5/2003 |
| WO | 03056340 | 7/2003 |

OTHER PUBLICATIONS

Constanzo et al., c-E10 is a caspase-recruiting domain-containing protein that interacts with components of death receptors signaling pathway and activates nuclear factor-kappaB. J. Biol. Chem. 274(29):20127-32, Jul. 16, 1999.*

Nam et al., Inhibition of both the extrinisic and intrinsic death pathways through nonhomotypic death-fold interactions, Mol. Cell, 16:901-912, Sep. 24, 2004.*

Pecot et al., RAN interference in the clinic:challenges and future directions, Nat. Rev. Cancer, 11(1):59-67, Jan. 2011.*

MacEwan, D.J., Review: TNF ligands and receptors—a matter of life and death, Brit. J. Pharmacol. 135:855-875, 2002.*

Green and Steinmetz, "Monitoring apoptosis in real time" Cancer J 8:82-92 (2002).

Green, "Apoptotic pathways: the roads to ruin" Cell 94:695-698 (1998).

Green, "Apoptotic pathways: paper wraps stone blunts scissors" Cell 102:1-4 (2000).

Griffith et al. "Functional Analysis of TRAIL Receptors Using Monoclonal Antibodies," J. Immunol. 162: 2597-2605 (1999).

Grimm et al., "RIP and FADD: two 'death domain' containing proteins can induce apoptosis by convergent, but dissociable, pathways" Proc. Natl. Acad. Sci. USA 93:10923-10927 (1996).

Hashimoto et al., "Co-overexpression of DEAD box protein rck/p54 and c-myc protein in human colorectal adenomas and the relevance of their expression in cultured cell lines" Carcinogenesis 22:1965-1970 (2001).

Heim, "RIG-I: an essential regulator of virus-induced interferon production." J. Hepato. 142, 431-433 (2005).

Heinlein, "Dead box for the living" J. Pathol. 184:345-7 (1998).

Hernandez et al., "Sensitization of human colon cancer cells to TRAIL-mediated apoptosis" J Gastrointest Surg 5:56-65 (2001).

Hinz et al., "Bcl-XL protects pancreatic adenocarcinoma cells against CD95- and TRAIL-receptor-mediated apoptosis" Oncogene 19: 54775486 (2000).

Ichijo, "[Molecular mechanisms for cell life and cell death]" Kokubyo Gakkai Zasshi 65:155-163 (1998) (Abstract Only).

Ichijo et al., "Induction of apoptosis by ASKI, a mammalian MAPKKK that activates SAPK/JNK and p38 signaling pathways" Science 275:90-94 (1997).

Ichikawa et al. "Tumoricidal activity of a novel anti-human DR5 monoclonal antibody without hepatocyte cytotoxicity," Nature Med. 7(8): 954-960 (2001).

Ichikawa et al., "TRAIL-R2 (DR5) mediates apoptosis of synovial fibroblasts in rheumatoid arthritis" J. Immunol. 25 171 :1061-1069 (2003).

Ip and Davis, "Signal transduction by the c-Jun N-terminal kinase (JNK)—from inflammation to development" Curr. Opin. Cell Biol. I0:205-219 (1998).

Irmier et al., "Inhibition of death receptor signals by cellular FLIP" Nature 388:190-195 (1997).

Japanese Office Action, App. No. 2007-554179; Issued Jul. 12, 2011.

Jeremias et al., "TRAIL induces apoptosis and activation of NF-kappaB" Eur. Cytokine Netw. 9:687-8 (1998).

Jo et al., "Apoptosis induced in normal human hepatocytes by tumor necrosis factor-related apoptosis-inducing ligand" Nat. Med. 6:564-7 (2000).

Jonsson et al., "cIAP-2 block apoptotic events in bladder cancer cells," Anticancer Research 23(4):3311-6 (2003).

Jonsson et al., "High level of cFLIP correlates with resistance to death receptor-induced apoptosis in bladder carcinoma cells," Anticancer Research 23(2B):1213-8 (2003).

Kang et al., "Expression analysis and genomic characterization of human melanoma differentiation associated gene-5, mda-5: a novel type I interferon-responsive apoptosis-inducing gene" Oncogene 23:1789-1800 (2004).

Kang et al., mda-5: An interferon-inducible putative RNA helicase with double-stranded RNA-dependent ATPase activity and melanoma growth-suppressive properties. Proc Natl Acad Sci USA 99:637-642 (2002).

Kasof and Gomes, "Livin, a novel inhibitor of apoptosis protein family member" J Biol Chem 276:3238-3246 (2001).

Kawai et al., "IPS-I, an adaptor triggering RIG-1- and Mda5-mediated type I interferon induction" Nat Immunol 6, 981-988 (2005).

Keane et al. "Chemotherapy Augments TRAIL-induced Apoptosis in Breast Cell Lines" Cancer Res. 59:734-741 (1999).

(56) References Cited

OTHER PUBLICATIONS

Kischkel et al., "Apo2L/TRAIL-dependent recruitment of endogenous FADD and caspase-8 to death receptors 4 and 5" Immunity 12:611-20 (2000).
Kischkel et al., "Death receptor recruitment of endogenous caspase-10 and apoptosis initiation in the absence ofcaspase-8" J Biol Chem 276:46639-46646 (2001).
Krammer, "CD95's deadly mission in the immune system" Nature 407:789795 (2000).
Krueger et al., "Cellular FLICE-inhibitory protein splice variants inhibit different steps of caspase-8 activation at the CD95 death-inducing signaling complex" J Biol Chem 276:20633-20640 (2001).
Krueger et al., "FLICE-inhibitory proteins: regulators of death receptor-mediated apoptosis" Mol Cell Biol 21 :82478254 (2001).
Kuang et al., "FADD is required for DR4- and DR5-mediated apoptosis: lack of trail-induced apoptosis in FADD-deficient mouse embryonic fibroblasts" J. Biol. Chem. 275:25065-8 (2000).
Lassus et al., "Requirement for caspase-2 in stress-induced apoptosis before mitochondrial permeabilization" Science 297:1352-1354 (2002).
Lawrence et al., "Differential hepatocyte toxicity of recombinant Ap02L/TRAIL versions" Nat Med 7:383-385 (2001).
LeBlanc et al., "Tumor-cell resistance to death receptor-induced apoptosis through mutational inactivation of the proapoptotic Bc1-2 homolog Bax" Nat Med 2002; 8: 274-281 (2002).
Li et al., "A small molecule Smac mimic potentiates TRAIL- and TNFalpha-mediated cell death" Science 305, 1471-1474 (2004).
Li et al., "Inducible resistance of tumor cells to tumor necrosis factor-related apoptosis-inducing ligand receptor 2-mediated apoptosis by generation of a blockade at the death domain function" Cancer Res. 66(17):8520-8 (2006).
Li et al., "The IAP family: endogenous caspase inhibitors with multiple biological activities" Cell Res 10, 169-177 (2000).
Lin et al., "The death domain kinase RIP is essential for TRAIL (Ap02L)-induced activation of IkappaB kinase and c-Jun N-terminal kinase" Mol Cell Biol 20:6638-6645 (2000).
MacFarlane et al., "Identification and molecular cloning of two novel receptors for the cytotoxic ligand TRAIL" J Biol Chem 272:25417-25420 (1997).
Marsters et al., "A novel receptor for Apo2L1TRAIL contains a truncated death domain" Curr Biol 7:1003-1 006 (1997).
Matsuzaki et al., "Combination of tumor necrosis factor-related apoptosis-inducing ligand (TRAIL) and actinomycin D induces apoptosis even in TRAIL-resistant human pancreatic cancer cells" Clin Cancer Res 7: 407-414 (2001).
McCarthy et al., "RIP2 is a novel NF-kappaB-activating and cell death-inducing kinase" J. Biol. Chem. 273:16968-75 (1998).
Meng et al., "Induction of cell death in breast cancer cells by anti-TRAIL R2/DR5 antibody alone and in combination with TRAIL," American Association for Cancer Research, 91st Annual Meeting, Apr. 1-5, 2000, Abstract LB-27.
Mitsiades et al., "TRAIL/AP02L ligand selectively induces apoptosis and overcomes drug resistance in multiple myeloma: therapeutic applications" Blood 98:795-804 (2001).
Mitsiades et al., "Intracellular regulation of tumor necrosis factor-related apoptosis-inducing ligand induced apoptosis in human multiple myeloma cells" Blood 99:2162-2171 (2002).
Mizutani et al., "Synergistic Cytotoxicity and Apoptosis by Apo-2 Ligand and Adriamycin against Bladder Cancer Cells" Clin. Cancer Res. 5:2605-12 (1999).
Muzio et al., "FLICE, a novel FADD-homologous ICE/CED-3-like protease, is recruited to the CD95 (Fas/APO-I) death-inducing signaling complex" Cell 85:817-827 (1996).
Nagata, "Apoptosis by death factor" Cell 88:355-65 (1997).
Ng and Bonavida, "X-linked inhibitor of apoptosis (XIAP) blocks Apo2 ligand/tumor necrosis factor-related apoptosis-inducing ligand-mediated apoptosis of prostate cancer cells in the presence of mitochondrial activation: sensitization by overexpression of second mitochondria-derived activator of caspase/direct IAP binding protein with low pl (Smac/DIABLO)" Mol Cancer Ther 1: 1051-1058 (2002).
Nicholson, "From bench to clinic with apoptosis-based therapeutic agents" Nature 407,810-816 (2000).
Nishitoh et al., "ASK1 is essential for JNK/SAPK activation by TRAF2" Mol Cell 2:389-395 (1998).
Ohtsuka and Zhou, "Bisindolylmaleimide Vln enhances DR5-mediated apoptosis through the MKK4/JNK/p38 kinase and the mitochondrial pathways" J Biol Chem 277:29294-29303 (2002).
Ohtsuka et al., "Synergistic induction of tumor cell apoptosis by death receptor antibody and chemotherapy agent through JNKIp38 and mitochondrial death pathway" Oncogene 22:2034-2044 (2003).
Owsianka and Patel, "Hepatitis C virus core protein interacts with a human DEAD box protein DDX3" Virology 257:330-340 (1999).
Pan et al., "An antagonist decoy receptor and a death domain-containing receptor for TRAIL" Science 277:815-818 (1997).
Pan et al., "The receptor for the cytotoxic ligand TRAIL" Science 276, 111-113. (1997).
Pan et al., "Caspase-9, Bcl-XL, and Apaf-1 form a ternary complex" The Journal of Biological Chemistry 273:5841-5 (1998).
Park et al., "IFN-gamma inhibition of TRAIL-induced IAP-2 upregulation, a possible mechanism of IFN-gamma-enhanced TRAIL-induced apoptosis" Biochem Biophys Res Commun 2002; 291: 233-236 (2002).
Payan and Luo, "Identification of RIP3, a RIP-like kinase that activates apoptosis and NFkappaB" Curr Biol 9:539-542 (1999).
Pitti et al., "Induction of apoptosis by Apo-2 ligand, a new member of the tumor necrosis factor cytokine family" J Biol Chem 271, 12687-12690 (1996).
Roa et al., "X-linked inhibitor regulating TRAIL-induced apoptosis in chemoresistant human primary glioblastoma cells" Clin Invest Med 2003; 26: 231-242.
Rokhlin et al., "Bc1-2 oncoprotein protects the human prostatic carcinoma cell line PC3 from TRAIL-mediated apoptosis" Oncogene 20:2836-2843 (2001).
Sachsenmaier, "Targeting protein kinases for tumor therapy" Onkologie 24:346-55 (2001).
Saleh et al., "Cytochrome c and dATP-mediated oligomerization of Apaf-I is a prerequisite for procaspase-9 activation" J Biol Chem 274:17941-17945 (1999).
Satyamoorthy et al., "No longer a molecular black box new clues to apoptosis and drug resistance in melanoma" Trends in Molecular Medicine 7(5):191-4 (2001).
Scaffidi et al., "Two CD95 (APO-I/Fas) signaling pathways" EMBO J 17:1675-1687 (1998).
Schneider et al., "Characterization of two receptors for TRAIL" FEBS Lett 416:329-334 (1997).
Schneider et al., "TRAIL receptors 1 (DR4) and 2 (DR5) signal FADD-dependent apoptosis and activate NF-kappaB" Immunity 7:831-836 (1997).
Schroder, "Human DEAD-box protein 3 has multiple function sin gene regulation and cell cycle control and is a prime target for viral manipulation," Biochem. Pharm. 79:297-306 (2010).
Sheridan et al., "Control of TRAIL-induced apoptosis by a family of signaling and decoy receptors" Science 277:818-821 (1997).
Siegmund et al., "Selective inhibition of flice-like inhibitory protein (FLIP) expression with small interfering RNA oligonucleotides (siRNAs) is sufficient to sensitize tumor cells for TRAIL-induced apoptosis," Mol. Med. 8(11):725-32 (2002).
Sinicrope et al., "Tumor necrosis factor-related apoptosis-inducing ligand-induced apoptosis is inhibited by Bc1-2 but restored by the small molecule Bc1-2 inhibitor, HA 14-1, in human colon cancer cells" Clin Cancer Res 10: 8284-8292 (2004).
Song et al. "Tumor necrosis factor-related apoptosis inducing ligand (TRAIL) is an inhibitor of autoimmune inflammation and cell cycle progression" J. Exp. Med. 191(7):1095-1103 (2000).
Sprick et al., "FADD/MORTI and caspase-8 are recruited to TRAIL receptors 1 and 2 and are essential for apoptosis mediated by TRAIL receptor 2" Immunity 12:599-609 (2000).
Srivastava "TRAIL/Apo-2L:Mechanisms and clinical applications in cancer" Neoplasia 3(6):535-546 (2001).

(56) References Cited

OTHER PUBLICATIONS

Stanger et al., "RIP: a novel protein containing a death domain that interacts with Fas/APO-1(CD95) in yeast and causes cell death" Cell 81 :513-523 (1995).
Straughn et al., "Anti-tumor activity of TRA-8 anti-death receptor 5 (DR5) monoclonal antibody in combination with chemotherapy and radiation therapy in a cervical cancer model" Gynecologic Oncology 101(1):46-54 (2006).
Sun et al., "Augmentation of tumor necrosis factor-related apoptosis-inducing ligand (TRAIL)-induced apoptosis by the synthetic retinoid 6-[3-(1-adamantyl)-4-hydroxyphenyl]-2-naphthalene carboxylic acid (CD437) through up-regulation of TRAIL receptors in human lung cancer cells" Cancer Res 2000; 60: 7149-7155 (2000).
Sun et al., "Identification of an antiapoptotic protein complex at death receptors," Cell Death Diff. 15(12):1887-1900 (2008).
Suzuki et al., "X-linked inhibitor of apoptosis protein (XIAP) inhibits caspase-3 and -7 in distinct modes" J Biol Chem 276:27058-27063 (2001).
Thomas et al., "TNF-related apoptosis-inducing ligand (TRAIL) induces apoptosis in fas ligand resistant melanoma cells and mediates CD4 T-cell killing of target cells" Journal of Immunology 161:2195-2220 (1998).
Ting et al., "RIP mediates tumor necrosis factor receptor 1 activation of NF-kappaB but not Fas/APO-I-initiated apoptosis" EMBO J 15:6189-6196 (1996).
Tournier et al., "Requirement of JNK for stress-induced activation of the cytochrome c-mediated death pathway" Science 288:870-874 (2000).
Vucic et al., "ML-IAP, a novel inhibitor of apoptosis that is preferentially expressed in human melanomas" Curr Biol 10:1359-1366 (2000).
Wagner et al., "Caspase-2 can function upstream of bid 30 cleavage in the TRAIL apoptosis pathway" J Biol Chem 279: 35047-35052 (2004).
Walczak et al., "Tumoricidal activity of tumor necrosis factor-related apoptosis-inducing ligand in vivo," Nat Med 5:157-163. (1999).
Walczak et al., "TRAIL-R2: a novel apoptosis-mediating receptor for TRAIL," EMBO J 16:5386-5397 (1997).
Wang et al., "NF-kappaB induces expression of the Bcl-2 homologue A1/Bfl-1 to preferentially suppress chemotherapy-induced apoptosis," Mol Cell Biol 19:5923-5929 (1999).
Wen et al., "Antileukemic drugs increase death receptor 5 levels and enhance Apo-2L induced apoptosis of human leukemia cells" Blood 96:3900-6 (2000).
Wieland et al., "Molecular characterization of the DICE1 (DDX26) tumor suppressor gene in lung carcinoma cells" Oncol Res 12,491-500 (2000).
Wiley et al., "Identification and characterization of a new member of the TNF family that induces apoptosis" Immunity 3:673-682 (1995).
Yamanaka et al., "Chemotherapeutic agents augment TRAIL-induced apoptosis in human hepatocellular carcinoma cell lines" Hepatology 32:482-490 (2000).
Yang et al., Daxx, a novel Fas-binding protein that activates JNK and apoptosis. Cell 89:1067-1076 (1997).
Yedavalli et al., Requirement ofDDX3 DEAD box RNA helicase for HN-1 Rev-RRE export function. Cell 119, 381-392 (2004).
Yoneyama et al., "The RNA helicase RIG-I has an essential function in double-stranded RNA-induced innate antiviral responses" Nature Immunology 5(7):730-7 (2004).
Yoneyama et al., "Functions of the DExD/H-Box Helicases RIG-I, MDA5, and LGP2 in Antiviral Innate Immunity" J Immunol175, 2851-2858 (2005).
Yoneyama and Fujita, "[RIG-I: critical regulator for virus-induced innate immunity]" Tanpakushitsu Kakusan Koso 49, 2571-2578 (2004) (Japanese original with certified English translation).
Zamai et al., "Natural killer (NK) cell-mediated cytotoxicity: differential use of TRAIL and Fas ligand by immature and mature primary human NK cells" J. Exp. Med. 188(12):2375-80 (1998).
Zhou et al., "Immunobiology of tumor necrosis factor receptor superfamily" Immunol Res 26:323-336 (2002).
Kawasaki et al., "VI. Manipulation of Gene Manifestation, In vitro Dicing and Optimized Expression Vectors for siRNA in Mammalian Cells", Proteins, Nucleic Acids and Enzymes, vol. 48, No. 11, 2003, 1638-1645.
Sumimoto et al., "Inhibition of Growth and Invasive Ability of Melanoma by Inactivation of Mutated BRAF with Lentivirus-mediated RNA interference", Oncogene, 23, 2004, 6031-6039.
Yokota, "Gene Therapy of Virus Replication with RNAi", Virus, vol. 55, No. 1, 2005,1-8.
Office Action for CA Application No. 2,595,440 mailed Oct. 3, 2014 (2 pages).
Reexamination Notice for Chinese Patent Application No. 200680010114.8 mailed Jun. 30, 2014 along with an English translation (15 pages).
Office Action for Japanese Patent Application No. 2011-284044 mailed Sep. 2, 2014 including English translation.
Akao et al., "A tumour-associated DEAD-box protein, rck/p54 exhibits RNA unwinding ac-tivity toward c-myc RNAs in vitro" Genes to Cells 8, 671-676 (2003).
Alnemri et al., "Human ICE/CED-3 protease nomenclature" Cell 87:171 (1996).
Andrejeva et al., "The V proteins ofparamyxoviruses bind the IFN-inducible RNA helicase, mda-5, and inhibit its activation ofthe IFN-beta promoter" Proc Natl Acad Sci USA 101, 17264-17269 (2004).
Ashhab et al., "Two splicing variants of a new inhibitor of apoptosis gene with different biological properties and tissue distribution pattern" FEBS Lett 495:56-60 (2001).
Ashkenzai et al., "Safety and antitumor activity of recombinant soluble Apo2 ligand" J. Clin. Invest. 104:155-62 (1999).
Baldwin, "Control of oncogenesis and cancer therapy resistance by the transcription factor NF-kappaB" J Clin Invest 107:241-246 (2001).
Baldwin, "The NF-kappa B and I kappa B proteins: new discoveries and insights" Annu Rev Immunol. 14:649-683 (1996).
Belka, et al., "Sensitization of resistant lymphoma cells to irradiation-induced apoptosis by the death ligand TRAIL" Oncogene 20:2190-2196 (2001).
Bendele et al., "Effects of PEGylated soluble tumor necrosis factor receptor type I (PEG sTNF-RI) alone and in combination with methotrexate in adjuvant arthritic rats" Clin Exp. Rheumatol. 17(5):553-560 (1999).
Bockbrader et al., "A small molecule Smac-mimic compound induces apoptosis and sensitizes TRAIL- and etoposide-induced apoptosis in breast cancer cells" Oncogene 24(49):7381-8 (2005).
Bodmer et al., "TRAIL receptor-2 signals apoptosis through FADD and caspase-8" Nat. Cell Biol. 2:241-3 (2000).
Boldin et al., "A novel protein that interacts with the death domain ofFas/APOI contains a sequence motif related to the death domain" J Biol Chern 270:7795-7798 (1995).
Boldin et al., "Involvement of MACH, a novel MORTI/FADD-interacting protease, in Fas/APO-l- and TNF receptor-induced cell death" Cell 85:803-815 (1996).
Bonavida et al., "Selectivity of TRAIL-mediated apoptosis of cancer cells and synergy with drugs: The trail to non-toxic cancer therapeutics (Review)" Int. J. Oncol. 15:793-802 (1999).
Buchsbaum et al., "Treatment of human breast cancer xenografts with monoclonal antibody against DR5 with or without chemotherapy inhibits tumor growth in nude mice" Proceedings of the Annual Meeting of the American Association for Cancer Research 43:1005-6 (Mar. 2002) (Abstract).
Buchsbaum et al., "Antitumor efficacy ofTRA-8 anti-DR5 monoelonal antibody alone or in combination with chemotherapy and/or radiation therapy in a human breast cancer model" Clin Cancer Res 9,3731-3741 (2003).
Budihardjo et al., "Biochemical pathways of caspase activation during apoptosis" Annu Rev Cell Dev Biol 15:269-290 (1999).
Carthy et al., "Bcl-2 35 and Bcl-xL overexpression inhibits cytochrome c release, activation of multiple caspases, and virus release following coxsackievirus B3 infection" Virology 313: 147-157 (2003).

(56) References Cited

OTHER PUBLICATIONS

Causevic et al., "Overexpression and poly-ubiquitylation of the DEAD-box RNA helicase p68 in colorectal tumours" Oncogene 20:7734-7743 (2001).
Chang et al., "Activation of apoptosis signal-regulating kinase 1 (ASK1) by the adapter protein Daxx" Science 281 :1860-186 (1998).
Chaudhary et al., "Death receptor 5, a new member of the TNFR family, and DR4 induce FADD-dependent apoptosis and activate the NFkB pathway" Immunity 7(6):821-30 (1997).
Chawla-Sarkar et al., "Downregulation of Bcl-2, FLIP or IAPs (XIAP and survivin) by siRNAs sensitizes resistant melanoma cells to AP02L/TRAIL-induced apoptosis" Cell Death Differ 11: 915-923 (2004).
Chen et al., "The Rel/NF-kappaB family directly activates expression of the apoptosis inhibitor Bcl-x(L)" Mol Cell Biol 20:2687-2695 (2000).
Chinnaiyan et al., "FADD, a novel death domain-containing protein, interacts with the death domain of Fas and initiates apoptosis" Ce11 81:505-512 (1995).
Chinnaiyan et al., "Combined effect of tumor necrosis-factor related apoptosis-inducing ligand and ionizing radiation in breast cancer therapy" PNAS 97(4):1754-9 (2000).
Chuntharapai et al., "Isotype-Dependent Inhibition of Tumor Growth in vivo by Monoclonal Antibodies to Death Receptor 4" J. Immunol. 166:4891-4898 (2001).
Cohen and Goedert, "GSK3 inhibitors: development and therapeutic potential" Nature Reviews 3:479-87 (2004).
Crook et al., "An apoptosis-inhibiting baculovirus gene with a zinc finger-like motif" J Virol. 67:2168-2174 (1993).
Cuello et al., "Synergistic induction of apoptosis by the combination of trail and chemotherapy in chemoresistant ovarian cancer cells" Gynecol Oncol. 81: 380-390 (2001).
Cummins et al., "X-linked inhibitor of apoptosis protein (XIAP) is a non-redundant modulator of tumor necrosis factor-related apoptosis-inducing ligand (TRAIL)-mediated apoptosis in human cancer cells" Cancer Res 64: 3006-3008 (2004).
Czuczman et al., "Treatment of patients with low-grade B-cell lymphoma with the combination of chimeric anti-CD20 monoclonal antibody and CHOP chemotherapy" J. Clin. Oncol. 17(1):268-76 (1999).
Damiano and Reed, "CARD proteins as therapeutic targets in cancer" Curr. Drug Targets 5:367-374 (2004).
Degli-Esposti et al., "The novel receptor TRAIL-R4 induces NF-kappaB and protects against TRAIL-mediated apoptosis, yet retains an incomplete death domain" Immunity 7:813-820 (1997).
Desagher and Martinou, "Mitochondria as the central control point of apoptosis" Trends Cell Biol. 10:369-377 (2000).
DeRosier et al., "Treatment with gemcitabine and TRA-8 anti-death-receptor-5 mAb reduces pancreatic adenocarcinoma cell viability in vitro and growth in vivo" Journal of Gastrointestinal Surgery 10(9):1291-1300 (2006).
Deveraux et al., "IAPs block apoptotic events induced by caspase-8 and cytochrome c by direct inhibition of distinct caspases" EMBO J 17, 2215-2223 (1998).
Deveraux and Reed, "IAP family proteins—suppressors of apoptosis" Genes Dev 13:239-252 (1999).
Deverauz et al., "X-linked IAP is a direct inhibitor of cell-death proteases" Nature 388:300-304 (1997).
Dubey et al., "The immunodominant antigen of an ultraviolet-induced regressor tumor is generated by a somatic point mutation in the DEAD box helicase p68" J Exp Med 185,695-705 (1997).
Emery et al., "Osteoprotegerin is a receptor for the cytotoxic ligand TRAIL" J Biol Chem. 273: 14363-14367 (1998).
Fanger et al., "Human Dendritic Cells Mediate Cellular Apoptosis via Tumor Necrosis Factor-related Apoptosis-inducing Ligand (TRAIL)" J. Exp. Med. 190(8):1155-64 (1999).
Fesik, "Insights into programmed cell death through structural biology" Cell 103:273-282 (2000).
Fu et al., "Molecular cloning and characterization of human DDX36 and mouse Ddx36 genes, new members of the DEADIH box superfamily." Acta Biochimica Et Biophysica Sinica 34:655-661 (2002).
Fujisawa et al., "Therapeutic Effect of the Anti-Fas Antibody on Arthritis in HTLV-I tax Transgenic Mice" J. Clin. Invest. 98(2): 271-278 (1996).
Fulda et al., "Inhibition of TRAIL-induced apoptosis by Bcl-2 overexpression" Oncogene 21:2283-2294 (2002).
GenBank Database online, Accession # NM_024005, "Human DEAC (Asp-Glu-Ala-Asp) box polypeptide 3, X-linked (DDX3X), transcript variant 1, mRNA," Oct. 17, 2005, Accessed Nov. 15, 2010.
George et al., "Investigation of co-amplification of the candidate genes ornithine decarboxylase, ribonucleotide reductase, syndecan-I and a DEAD box gene, DDXI, with N-myc in neuroblastoma. United Kingdom Children's Cancer Study Group." Oncogene 12:1583-1587 (1996).
Gibson, et al., "Increased expression of death receptors 4 and 5 synergizes the apoptosis response to combined treatment with etoposide and TRAIL" Molecular and Cellular Biology 20(1):205-212 (2000).
Gliniak and Le, "Tumor necrosis factor-related apoptosis-inducing ligand's antitumor activity in vivo is enhanced by the chemotherapeutic agent CPT-11" Cancer Res 59:6153-6158 (1999).
Godbout et al., "Overexpression of a DEAD box protein (DDXI) in neuroblastoma and retinoblastoma cell lines" J Biol Chem 273:2116121168 (1998).
Zhou et al., "Bisindolylmaleimide VIII facilitates Fas-mediated apoptosis and inhibits T cell-mediated autoimmune diseases" Nat Med 5:42-48 (1999).
Zhou et al., "Targeted radiotherapy potentiates the cytotoxicity of a novel anti-human DR5 monoclonal antibody in prostate cancer" International Journal of Radiation Oncology Biology Physics 54(2, Suppl.):224 (2002).
Zhu et al., "Hepatitis C virus core protein enhances FADD-mediated apoptosis and suppresses TRADD signaling oftumor necrosis factor receptor" Virology 283, 178-187 (2001).
Zong et al., "The prosurvival Bcl-2 homolog Bfl-l/A1 is a direct transcriptional target of NF-kappaB that blocks TNFalpha-induced apoptosis" Genes Dev 13:382-387 (1999).
Zou et al., "An APAF-1.cytochrome c multimeric complex is a functional apoptosome that activates procaspase-9" J Biol Chem 274:11549-11556 (1999).
Dillon et al., AZFz gene DBY (DDX3Y) is widely transcribed but the protein is limited to the male germ cells by translational control, Human Mol. Genet. 13(9):2333-41 (2004).
Genbank Accession No. AAC34298.1, DEAD box RNA helicase DDX3, *Homo sapiens*, Jun. 28, 1999.
Izeradjene et al., Casein kinase II (CK2) enhances death-inducing signaling complex (DISC) activity in TRAIL-induced apoptosis in human colon carcinoma cell lines, Oncogene 24(12):2050-8 (2005).
Liao et al., Glycogen synthase kinase-3 beta suppression eliminates tumor necrosis factor-related apoptosis-inducing ligand resistance in prostate cancer, Molecular Cancer Therapeutics 2:1215-1222 (2003).
Martelli et al., A new selective AKT pharmacological inhibitor reduces resistance to chemotherapeutic drugs, Trail, all-trans-retinoic acid, and ionizing radiation of human leukemia cells, Leukemia 17:1794-1805 (2003).
Mitsiades et al., Apoptotic signaling induced by immunomodulatory thalidomide analogs in human multiple myeloma cells: therapeutic implications, Blood 99:4525-4530 (2002).
Mitsiades et al., Molecular profile of the anti-myeloma activity of histone deacetylase (HDCA) inhibitors: Biological and therapeutic implications, Blood 102(11):189a (2003).
Pennarun et al., Playing DISC: turning on TRAIL death receptor-mediated apoptosis in cancer, Biochim. Biophys. Acta 1805:123-140 (2010).
UnitProtKB/Swiss-Prot Database, Accession No. O00571, DDX3X_Human, version 148, last modified Nov. 28, 2012, accessed Nov. 29, 2012.

(56) References Cited

OTHER PUBLICATIONS

UniProtKB/Swiss-Prot Database, Accession No. O15523, DDX3Y_Human, version 122, last modified Nov. 28, 2012, accessed Nov. 29, 2012.

* cited by examiner

B
TRA-8
2E12
MDA231P
MDA231R
MDA231P
MDA231R
0 1 2 4 0 1 2 4 0 1 2 4 0 1 2 4 (hrs)
p-JNK
p-p38

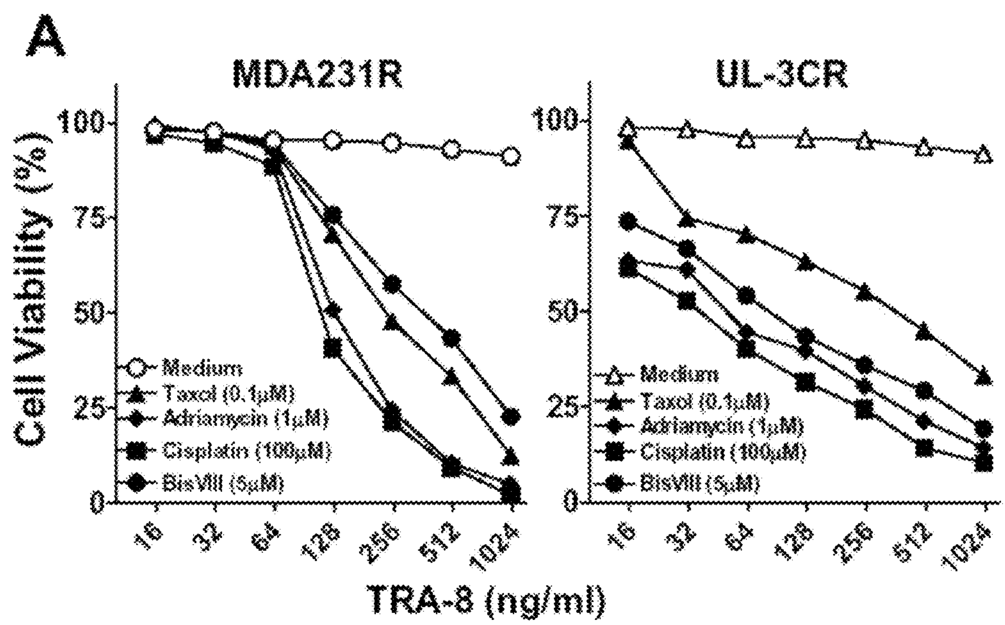
FIG. 6A
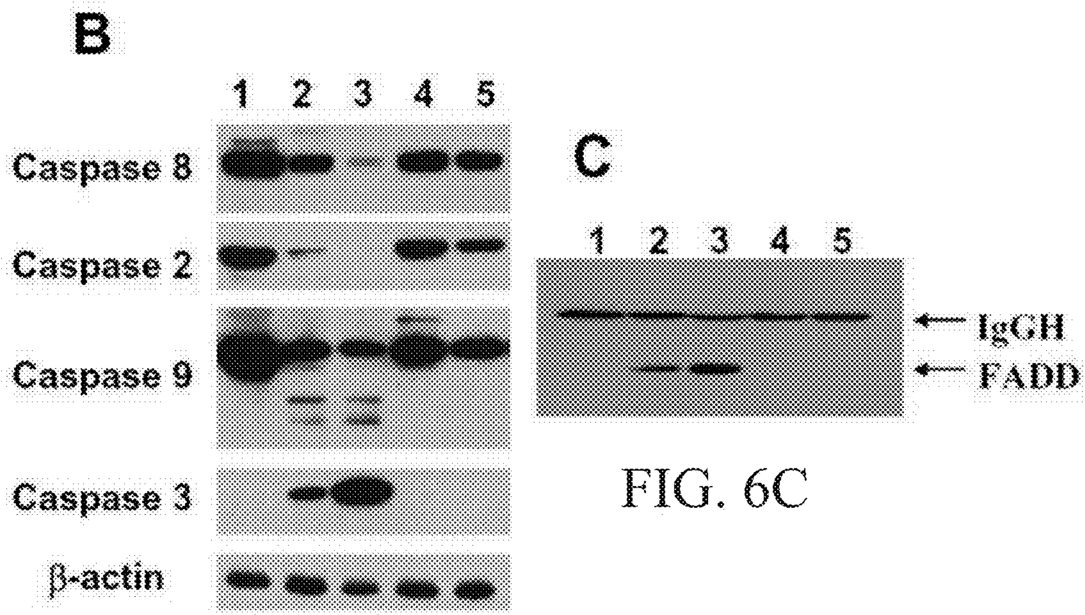
FIG. 6C
FIG. 6B

| | Binding to DR5 |
|---|---|
| FL DDX3: 1-662 aa | + |
| ND1 DDX3: 50-662 aa | + |
| ND2 DDX3: 100-662 aa | + |
| ND3 DDX3: 150-662 aa | + |
| ND4 DDX3: 200-662 aa | + |
| ND5 DDX3: 250-662 aa | − |
| ND6DDX3: 300-662 aa | − |
| CD1 DDX3: 1-550 aa | + |
| CD2DDX3: 1-500 aa | + |
| CD3 DDX3: 1-450 aa | + |
| CD4 DDX3: 1-400 aa | + |
| CD5 DDX3: 1-350 aa | − |
| CD6 DDX3: 1-300 aa | − |

```
 DR5:   4 SPGESEHLLEPAEAERSQRRRLLVPAN   30                 (SEQ ID NO:43)
          SP E + LLE AEAE QRRRLLVP N
DcR2: 709 SPEEPQRLLEQAEAEGCQRRRLLVPVN   735 20/27 (74%)    (SEQ ID NO:44)
          SPGE++ LL PAEAE SQRRRLLVPAN
 DR4: 330 SPGEAQCLLGPAEAEGSQRRRLLVPAN   356 24/27 (88%)    (SEQ ID NO:45)
```

SGIHSGATTTAPS (SEQ ID NO:18) B-Catenin

SVPPSPSGSQASSPQSS (SEQ ID NO:19) glycogen synthase

SSFGSRSDSRGKSSFFSDRGS (SEQ ID NO:20) DDX3

| TRA-8 | 0 | 1 | 1 | 0.1 | 0.1 | (μg/ml) |
|---|---|---|---|---|---|---|
| Lithium | 0 | 0 | + | 0 | + | |

AGENTS AND METHODS RELATED TO SCREENING FOR RESISTANCE TO DR5 AND REDUCING RESISTANCE TO DR5 AGONISTS

CROSS-REFERENCE TO RELATED APPLICATIONS

This application is a divisional application of and claims priority to U.S. Ser. No. 13/356,739, filed Jan. 24, 2012, which is a divisional application of U.S. Ser. No. 11/814,551, filed Mar. 19, 2008, which is a §371 of International Application No. PCT/US2006/03503 filed Jan. 31, 2006. International Application No. PCT/US2006/03503 claims priority to U.S. Provisional Application No. 60/649,437, filed Feb. 2, 2005. The applications which the present application claims priority to are herein incorporated by reference in their entireties.

STATEMENT REGARDING FEDERALLY SPONSORED RESEARCH

This invention was made with government support under Grant Nos. P50CA83591, P50CA89019, and U19AI056542 awarded by the National Institutes of Health. The government has certain rights in the invention.

FIELD OF THE INVENTION

The disclosed invention relates generally to agents that inhibit resistance to apoptosis-inducing agonists of death receptors and the use of such agents and agonists and biomarkers in the treatment of cancer and autoimmune or inflammatory diseases.

BACKGROUND OF THE INVENTION

TNF-related apoptosis-inducing ligand (TRAIL), a member of the TNF superfamily, has a strong apoptosis-inducing activity against cancer cells (Wiley, S. R., et al. 1995. Immunity 3:673-682). Unlike other death-inducing ligands of the TNF superfamily such as TNF-α and Fas ligand, TRAIL has been of particular interest in the development of cancer therapeutics as it preferentially induces apoptosis of tumor cells, having little or no effect on normal cells (Walczak, H., et al. 1999. Nat Med 5:157-163). At least five receptors for TRAIL have been identified, two of which, DR4 (TRAIL-R1) and DR5 (TRAIL-R2), are capable of transducing the apoptosis signal (Walczak, H., et al. 1997. Embo J 16:5386-5397; Pan, G., et al. 1997. Science 276:111-113; Chaudhary, P. M., et al. 1997. Immunity 7:821-830) whereas the other three (TRAIL-R3, -R4 and OPG) serve as decoy receptors to block TRAIL-mediated apoptosis (Pan, G., et al. 1997. Science 277:815-818; Marsters, S. A., et al. 1997. Curr Biol 7:1003-1006; Emery, J. G., et al. 1998. J Biol Chem 273:14363-14367). Like Fas and TNFR1, the intracellular segments of both DR4 and DR5 contain a death domain and transduce an apoptosis signal through a FADD- and caspase 8-dependent pathway (Walczak, H., et al. 1997. Embo J 16:5386-5397; Chaudhary, P. M., et al. 1997. Immunity 7:821-830; Kuang, A. A., et al. 2000. J Biol Chem 275:25065-25068). Administration of the recombinant soluble form of TRAIL in experimental animals, including mice and primates, induces significant tumor regression without systemic toxicity (Walczak, H., et al. 1999. Nat Med 5:157-163). However, as TRAIL has been shown to elicit side effects such as liver toxicity in humans, other agonists of TRAIL receptors have been developed.

Selective targeting of DR5 with a unique agonistic monoclonal anti-DR5 antibody, TRA-8, and its humanized or human versions thereof can effectively and selectively induce apoptosis of tumor cells. All TRAIL-sensitive cancer cells have been found to be susceptible to TRA-8-mediated apoptosis. Chemotherapeutic agents can synergistically enhance TRAIL-mediated apoptosis of tumor cells both in vitro and in vivo. For example, the combination therapy of TRA-8 with Adriamycin resulted in a significantly higher complete tumor regression rate than either agent alone (Buchsbaum, D. J., et al. 2003. Clin Cancer Res 9:3731-3741). These results suggest that chemotherapeutic agents might regulate the signal transduction of DR5 or the threshold of signaling required to induce apoptosis. TRA-8 has been selected as a candidate for development as a cancer therapy based on its efficacy and safety. Pre-clinical studies indicate that TRA-8 has a very strong anti-cancer efficacy in xenograft models of human cancer, particularly in combination with chemotherapy (Buchsbaum, D. J., et al. 2003. Clin Cancer Res 9:3731-3741). There is further indication that monkeys tolerate systemic administration of TRA-8 well. The binding of TRA-8 to monkey DR5 is similar to that of human DR5, and the monkeys tolerated doses as high as 48 mg/kg dose.

The expression of a death receptor by a target cell, however, is not necessarily sufficient to make the cell susceptible to the induction of apoptois by a ligand for the receptor. As an example, although most cancer cells express high levels of DR5, they are not necessarily susceptible to apoptosis induced by TRA-8, which is specific for DR5 and does not react with the decoy receptors. Furthermore, target cells such as cancer cells can show resistance to TRA-8 or other agents that induce apoptosis through death receptors (e.g., DR4 or DR5). Needed in the art is a biomarker to predict resistance and a means of reducing resistance of target cells to agonists of death receptors such as TRA-8.

BRIEF SUMMARY OF THE INVENTION

In accordance with the purpose(s) of this invention, as embodied and broadly described herein, this invention, in one aspect, relates to a method of reversing or preventing a target cell's resistance to a death receptor agonist comprising contacting the target cell with a modulator of one or more activities of a CARD containing protein, wherein the modulation reverses or prevents resistance to the agonist.

Provided herein is a method of screening a cell for a biomarker of resistance to a death receptor agonist comprising assaying the cell for total DDX3, or a homologue thereof, wherein high levels signify resistance to the agonist.

Provided herein is a method of screening a cell for a biomarker of resistance to a death receptor agonist comprising assaying the association of the death receptor and a CARD containing protein, wherein high levels of association signify resistance to the agonist.

Provided herein is a method of screening a cell for a biomarker of resistance to a death receptor agonist comprising a) contacting the cell with the death receptor agonist, b) monitoring the fractional association of the death receptor and a CARD containing protein, wherein association signifies resistance to the agonist.

Further provided is a method of screening a cell for a biomarker of resistance to a death receptor agonist comprising monitoring the association of a caspase or modulator of caspases (eg, cIAP1, cIAP2, XIAP, survivin) with the CARD containing protein and comparing the level of association with a sample from known resistant and non-resistant control cells, wherein the association of IAPs with the CARD containing protein at levels similar to that of resistant cells signifies resistance to the agonist. Optionally, the cell to be screened is pre-contacted with a death receptor agonist (e.g. agonistic antibody).

Provided herein is a method of monitoring resistance to a death receptor agonist in a subject, comprising (a) acquiring a biological sample from the subject and (b) detecting association of a CARD containing protein with a death receptor in the sample, the association indicating resistance.

Further provided is a method of monitoring resistance to a death receptor agonist in a subject, comprising (a) acquiring a biological sample from the subject and (b) detecting association of a caspase or modulator of caspase with a CARD containing protein in the sample, the association indicating resistance.

Also provided is a method of selectively inducing apoptosis in a target cell expressing a death receptor, comprising the steps of (a) contacting the target cell with a therapeutic amount of a death receptor agonist that specifically binds the death receptor and (b) administering to the target cell a therapeutic amount of a modulator of one or more activities of a CARD containing protein.

Provided is a method of treating a subject with cancer, comprising administering to the subject a therapeutic amount of (a) a death receptor agonist and (b) a modulator of one or more activities of a CARD containing protein, wherein the modulator reduces resistance to the death receptor agonist.

Also provided is a method of treating a subject with an inflammatory or autoimmune disease, comprising administered to the subject a therapeutic amount of (a) a death receptor agonist and (b) an agent that modulates one or more activities of a CARD containing protein, wherein the modulator reduces resistance to the death receptor agonist.

Provided herein is a composition comprising (a) a death receptor agonist and (b) an agent that modulates one or more activities of a CARD containing protein, wherein the modulator reduces resistance to the death receptor agonist.

Further provided is an isolated nucleic acid comprising an shRNA, wherein the shRNA inhibits the expression of a CARD containing protein.

Also provided is an isolated polypeptide encoding the CARD containing protein binding region of a death receptor, wherein the polypeptide comprises fewer than 25 amino acid residues.

Further provided is an isolated polypeptide comprising the death receptor binding domain of a CARD containing protein.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIG. 1A shows flow cytometry analysis of cell surface expression of TRAIL-R1 and TRAIL-R2. Human breast cancer cell line, MDA-231 and human ovarian cancer cell lines, UL-3C were stained with CyChrome-conjugated anti-TRAIL-R1 (2E12) and PE-conjugated anti-TRAIL-R2 (2B4), and analyzed by FACScan flow cytometer. FIG. 1B shows susceptibility of MDA-231 and UL-3C cells to TRA-8, 2E12 or TRAIL-mediated apoptosis. Cells were cultured in 96-well plate with 1,000 cells per well in triplicates and incubated with indicated concentrations of each apoptosis-inducing agent. For 2E12-induced apoptosis, 2 μg/ml goat anti-mouse IgG1 was added, and for TRAIL-induced apoptosis, anti-Flag antibody was added as the crosslinker. Cell viability was determined after overnight culture by ATPLITE assay. Cell viability was determined by the percentage of the counts of the treated wells over that of medium control. Each point represents an average of triplicates, and is representative for at least three independent experiments. FIG. 1C shows susceptibility of tumor cells to TRA-8-mediated apoptosis during induction of TRA-8 resistance. Induction of TRA-8 resistance was initiated by the treatment of cells with 1 ng/ml of TRA-8 for two days. The TRA-8 doses were doubled every two days until 2,000 ng/ml. At each cycle of the doses, cell viability of non-induced and induced cells under the treatment with each correspondent dose was determined by ATPLITE assay. Data are presented as an average of the triplicate culture.

FIG. 2A shows TRAIL-R2-induced apoptosis in MDA-231 and UL-3C cells. Both parental and resistant MDA231 and UL-3C cells were treated with indicated concentrations of TRA-8. FIG. 2B shows TRAIL-R1-induced apoptosis in MDA-231 and UL-3C cells. Both parental and resistant MDA231 and UL-3C cells were treated with indicated concentrations of 2E12. FIG. 2C shows TRAIL-induced apoptosis in MDA-231 and UL-3C cells. Both parental and resistant MDA231 and UL-3C cells were treated with indicated concentrations of recombinant soluble TRAIL. Cell viability was determined after overnight culture by ATPLITE assay as described above. FIG. 2D shows maintenance of TRA-8 resistance. After induction of TRA-8 resistance, TRA-8 was withdrawn. The maintenance of TRA-8 resistance was determined every week after withdraw of TRA-8. Cells were treated with 1,000 ng/ml TRA-8 overnight, and cell viability was determined by ATPLITE assay.

FIG. 3A shows Western blot analysis of protein expression. Total cell lysates were separated in SDS-PAGE and Western blotted. The blots were probed with 1 μg/ml primary antibody overnight and followed by HRP-conjugated secondary antibody. The proteins were revealed by ECL chemiluminescence. FIG. 3B shows cDNA array analysis of MDA231 parental and resistant cells. The membrane cDNA arrays for a panel of human apoptosis (upper panel) and cell signaling associated genes (lower panel) were purchased from SuperArray, Inc. The $^{32}P$ labeled cDNA probes were prepared from total RNA of MDA231 parental and resistant cells and hybridized with the cDNA array on the blot. The gene expression profiles were analyzed with CyClone PhosphorImager.

FIG. 4A shows TRAIL-R1 and -R2-triggered caspase activation. MDA231 parental and resistant cells were treated with 1,000 ng/ml TRA-8 (left panel) or 2E12 (right panel) for indicated time. Western blot of total cell lysates were probed with polyclonal anti-caspase 8 (upper panel), anti-caspase 3 (middle panel) or anti-PARP (lower panel). The arrows indicate the full-length and cleaved proteins. FIG. 4B shows activation of JUK/p38 kinase pathway. Cells were treated in the same way as described above. Western blots of total cell lysates were probed with polyclonal anti-phosphorylated JNK (upper panel) or anti-phosphorylated p38 (lower panel). The arrows indicate the phosphorylated proteins.

FIG. 5A shows co-immunoprecipitation assay of DISC formation. MDA231 parental and resistant cells were treated with 1,000 ng/ml TRA-8 (left panel) or 2E12 (right panel) for indicated time. TRAIL-R1 and TRAIL-R2 were immunoprecipitated with 2E12 or 2B4-conjugated Sepharose 4B. Western blots of the co-immunoprecipitated proteins and total cell proteins were probed with polyclonal anti-FADD (upper panel) or anti-caspase 8 antibody (middle panel) or anti-cFLIP antibody (lower panel). FIGS. 5B, 5C, 5D, and 5E show two dimension proteomic profile of TRAIL-R2-associated proteins of TRA-8 resistant cells. MDA231 parental and resistant cells were treated with 1,000 ng/ml TRA-8 for four hours or remained untreated as control. After TRAIL-R2 immunoprecipitation with 2B4-conjugated Sepharose 4B, the eluted proteins were separated by two dimension electrophoresis and stained with the SYPRO Ruby staining buffer. The differentially expressed protein spots as circled were identified by the PDQuest software. The experiments were repeated at least three times for a reproducible result.

FIGS. 6A, 6B, and 6C show reversal of TRA-8 resistance by chemotherapeutic agents. FIG. 6A shows susceptibility of TRA-8 resistant cells to TRA-8-induce apoptosis in the presence of chemotherapeutic agents. MDA231 and UL-3C resistant cells were treated with variable doses of TRA-8 in the absence or presence of 0.1 μM taxol, 1 μM Adriamycin, 100 μM cisplatin or 5 μM BisVIII. Cell viability was determined after overnight culture by ATPLITE assay. FIG. 6B shows activation of caspase cascade in TRA-8 resistant cells by Adriamycin. MDA231 resistant cells were culture in medium control (lane) or treated with 1,000 ng/ml TRA-8 and 1 μM Adriamycin for one hour (lane 2) or four hours (lane 3), or 1 μM Adriamycin alone or 1,000 ng/ml TRA-8 alone (lane 5). Western blots of total cell lysates were probed with monoclonal anti-human caspase antibodies. FIG. 6C shows TRAIL-R2 recruitment of FADD in TRA-8 resistant cells. TRAIL-R2 from differently treated MDA231 resistant cells as indicated above was immunoprecipitated with 2B4 sepharose 4B. Co-immunoprecipitation of FADD with TRAIL-R2 was determined by Western blot probed with anti-FADD antibody.

FIG. 8A shows constructs of deleted DDX3. The cDNAs encoding the full-length and deleted DDX3 as indicated were cloned into pcDNA3.1-HisA expression vector. 293 cells were transfected with the N-terminal, C-terminal deleted DDX3, and wild-type DDX3. 48 hours after transfection, the recombinant DDX3 expressions were detected by Western blot using anti-His antibody (FIG. 8B, upper panel). TRAIL-R2-co-immunoprecipitated recombinant DDX3 were determined by Western blot analysis using anti-His monoclonal antibody (FIG. 8B, middle panel). TRAIL-R2 were determined by Western Blot with anti-TRAIL-R2 polyclonal antibody (FIG. 8B, lower panel). Lane 1: non-transfection. Lane 2-5: Δ2-5 of N-terminal DDX3. Lane 6-9: Δ3-6 of C-terminal DDX3. Lane 10: the full-length DDX3. FIGS. 8C and 8D show the interaction of DDX3 with TRAIL-R2 is independent on death domain. The cDNAs encoding the full-length and deleted TRAIL-R2 as indicated were cloned into a shuttle-CMV vector (FIG. 8C). Murine 3T3 cells were co-transfected with either wild-type or mutant TRAIL-R2 and DDX3. 24 hours later, cell surface expression was examined by flow cytometry analysis using TRA-8 and PE-conjugated anti-mIgG1. 48 hours after co-transfection, cell lysates were immunoprecipitated with TRA-8. Total DDX3 (FIG. 8D, upper panel) and TRAIL-R2 associated DDX3 (FIG. 8D, middle panel) were examined by Western blot using anti-H is antibody. Lane 1: non-transfection; Lane 2: DDX3 alone; lane 3: wild-type TRAIL-R2 and DDX3; lane 4-9: Δ1-6 of TRAIL-R2 and DDX3. TRAIL-R2 were determined by Western Blot with anti-TRAIL-R2 polyclonal antibody (FIG. 8D, lower panel). FIGS. 8E and 8F show the cDNAs encoding the full-length and truncated TRAIL-R2 as indicated in FIG. 8E were cloned into a dual-promoter expression vector with GFP as a reporter protein. Murine 3T3 cells were co-transfected with either wild-type or mutant TRAIL-R2 and DDX3. 24 hours later, cell surface expression was examined by flow cytometry analysis using TRA-8 and PE-conjugated anti-mIgG1. 48 hours after co-transfection, cell lysates were immunoprecipitated with TRA-8. TRAIL-R2 were determined by Western Blot with anti-TRAIL-R2 polyclonal antibody (FIG. 8F, upper panel). Total DDX3 (FIG. 8F, lower panel) and TRAIL-R2 associated DDX3 (FIG. 8F, middle panel) were examined by Western blot using anti-His antibody. Lane 1: DDX3 alone; lane 2: ΔTRAIL-R2-300-330 and DDX3; lane 3: ΔD330 and DDX3; lane 4: ΔD340 and DDX3; lane 5: wild-type TRAIL-R2 and DDX3. FIG. 8G shows amino acid alignment of the DDX3 binding region of TRAIL-R2 with DcR2 and DR4. FIG. 8H shows DDX3 serves as the link between TRAIL-R2 and cIAP1. MDA231 parental cells and MDA231-resistant cells were treated with 500 ng/ml TRA-8 for the indicated time. TRAIL-R2 was immunoprecipitated with 2B4-conjugated Sepharose 4B. DDX3 was immunoprecipitated with 3E4-conjugated Sepharose 4B. Western blots of the total DDX3, cIAP1 (upper panel), TRAIL-R2 co-immunoprecipitated DDX3, cIAP1 (middle panel), DDX3 co-immunoprecipitated DDX3, cIAP1 (lower panel) were probed with 3E4, monoclonal anti-DDX3 antibody, and 1C12, monoclonal anti-cIAP1 antibody. TRAIL-R2 was determined by Western Blot using anti-TRAIL-R2 polyclonal antibody (middle panel).

FIGS. 9A and 9B show selected effective sRNAi-DDX3. MDA231 parental cells were transfected with U6-Entry vector encoding targets sRNAi-DDX3. 48 hours after transfection, DDX3 expression was determined by Western blot analysis using anti-DDX3 antibody. β-actin was used as the loading control. FIG. 9C shows MDA231-resistant cells were co-transfected with GFP expression vector and sRNAi-DDX3. 24 hours after transfection, GFP-positive cells were sorted by cytometry and cultured with various concentrations of TRA-8 overnight. DDX3 expressions were detected by Western blot using anti-DDX3 antibody (upper panel). TRAIL-R2 was immunoprecipitated with 2B4-conjugated Sepharose 4B. TRAIL-R2 associated DDX3 were probed with 3E4, monoclonal anti-DDX3 antibody (middle panel). 24 hours after transfection, the cells were treated with various concentrations of TRA-8 overnight. The susceptibility of transfected cells to TRA-8-induced apoptosis was determined by ATPLite assay (FIG. 9D). FIG. 9E shows the transfected cells undergoing apoptosis were determined by TUNEL staining FIG. 9F shows the panels of cancer cells were transfected with control or DDX3 sRNAi oligo. 48 hours after transfection, reduced expression of DDX3 was detected by Western blot using anti-DDX3 antibody. β-actin was used as the loading control. FIG. 9G shows 24 hours after transfection, cells were treated with various concentrations of TRA-8 overnight. The susceptibility of transfected cells to TRA-8-induced apoptosis was determined by ATPLite assay.

Figures 10A, 10B, 10C:
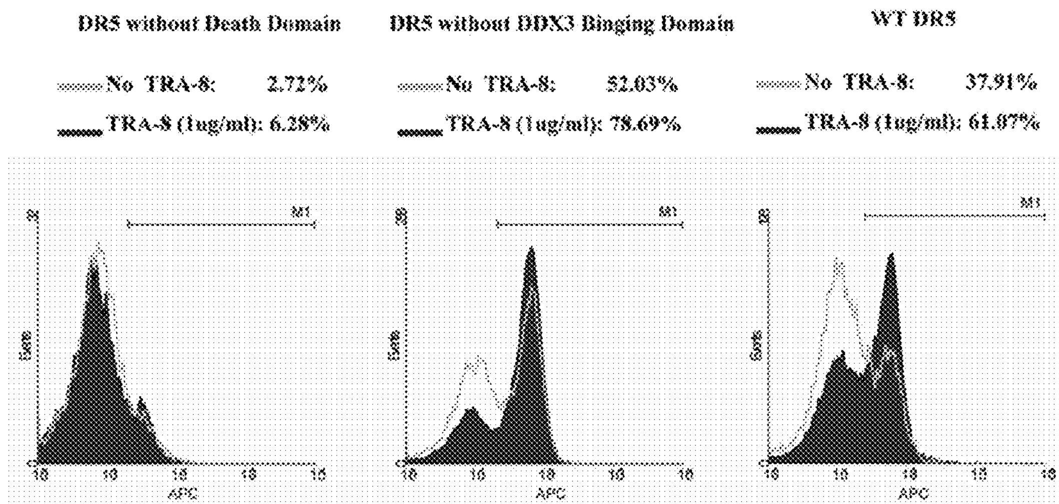
FIGS. 10A, 10B, 10C, 10D show TRAIL-R2 lacking DDX3 binding motif is pro-apoptotic.
Figure 10D:
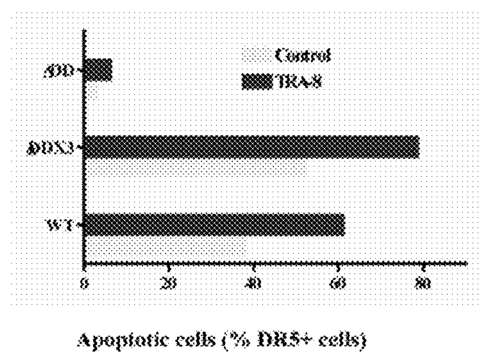

Murine 3T3 cells were co-transfected with ΔD340-TRAIL-R2 and DDX3, wild-type TRAIL-R2 and DDX3, ΔT300-330-TRAIL-R2 and DDX3. 24 hours after transfection, cells were treated with 500 ng/ml TRA-8 overnight. Apoptotic cells were determined by PE-conjugated anti-TRAIL-R2 antibody, biotin-conjugated annexin V in GFP-positive cells using flow cytometry analysis (FIGS. 10A, 10B, 10C, and 10D. Apoptotic cells were shown by the column bar graph (FIG. 10D).

Figure 11A:
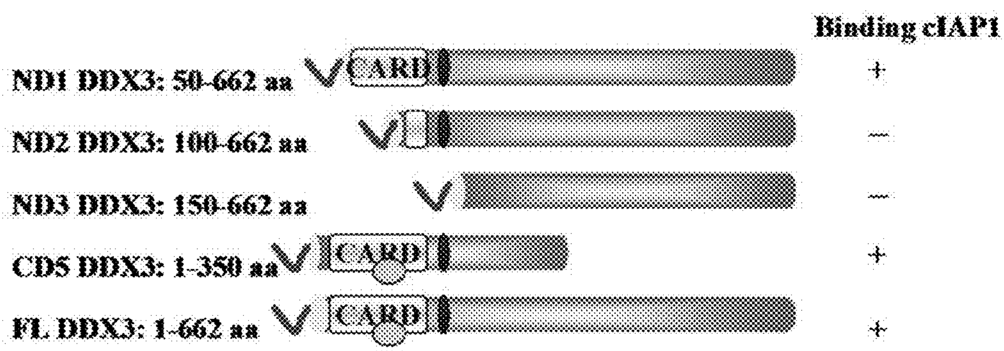
Figure 11B:
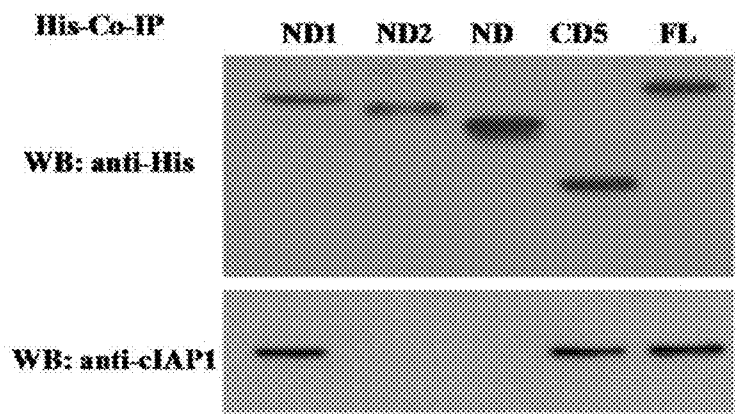
Figure 11C:
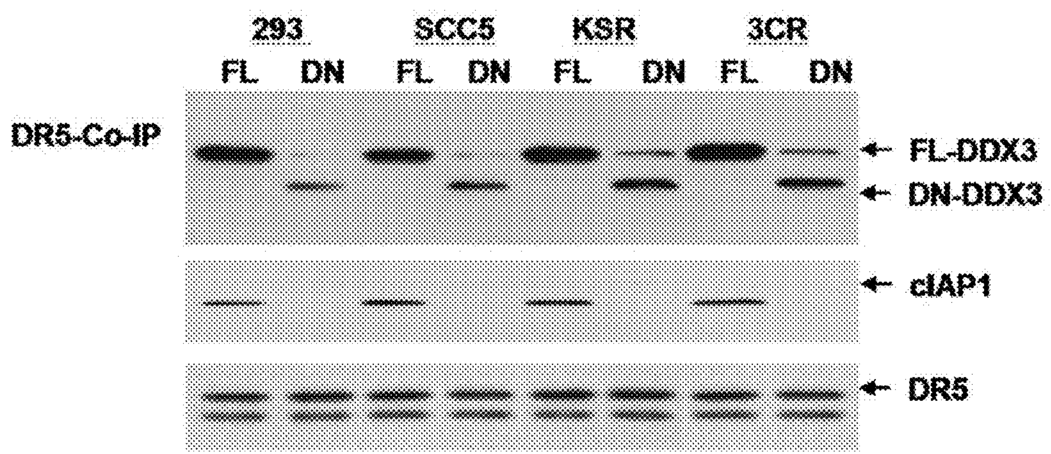

FIGS. 11A, 11B, and 11C show DDX3 serves as adaptor protein linking cIAP1 to TRAIL-R2. FIGS. 11A and B show mapping of cIAP1 binding CARD of DDX3. 293 cells were transfected with a series of deleted DDX3 as indicated (FIG. 1A), the N-terminal aa 1-aa 50 deleted (FIG. 11B, lane 1), the N-terminal aa 1-aa 100 deleted (FIG. 11B, lane 2), the N-terminal aa 1-aa 150 deleted (FIG. 11B, lane 3) and C-terminal aa 350-aa 662 deleted DDX3 (FIG. 11B, lane 4) and the full-length (FIG. 11B, lane 5). 48 hours after transfection, the recombinant DDX3 was immunoprecipitated with the nickel beads. Total cIAP1 (FIG. 11B, middle panel) and co-immunoprecipitated cIAP1 were determined by Western blot analysis using anti-cIAP1 monoclonal antibody (FIG. 11B, lower panel). FIG. 11C shows DDX3 lacking CARD reverses TRA-8 resistance. Four lines of TRA-8-resistant tumor cells were transfected with the adenoviral vector encoding the full-length DDX3 (DDX3-FL) or the CARD-truncated DDX3 (ΔCARD-DDX3). 48 hours after transfection, cell lysates were immunoprecipitated with TRA-8 and followed Western blot analysis of co-immunoprecipitated DDX3 (FIG. 11C, upper panel), and cIAP1 (FIG. 11C, middle panel). TRAIL-R2 were determined by Western Blot using anti-TRAIL-R2 polyclonal antibody (FIG. 11C, lower panel).

Figure 11D:
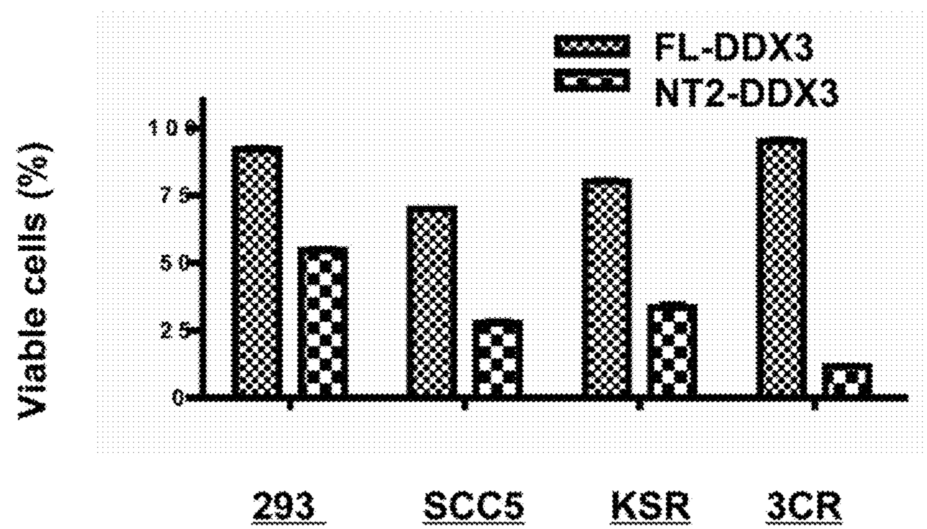

FIG. 11D shows cell viability determined by ATPLite assay. The transfected cells were incubated with 500 ng/ml TRA-8 overnight.

Figures 12A, 12B, 12C:
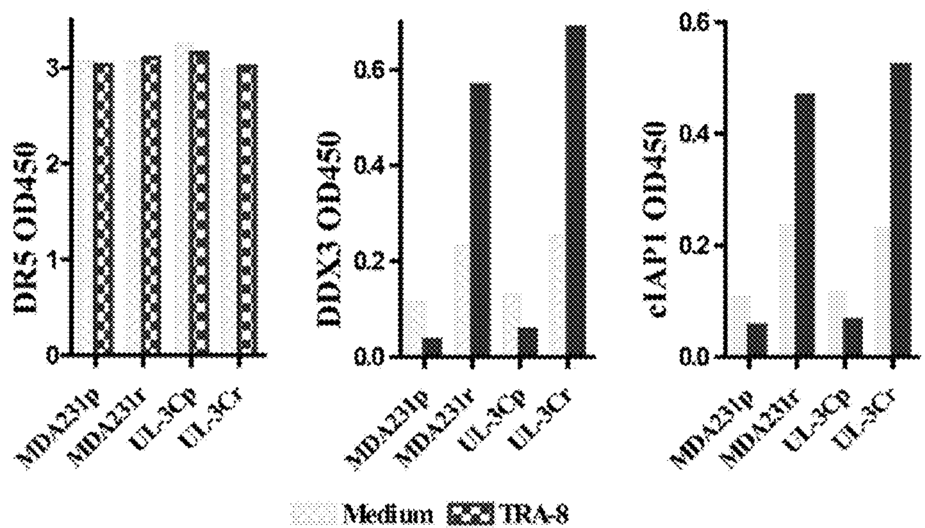
Figure 12D:
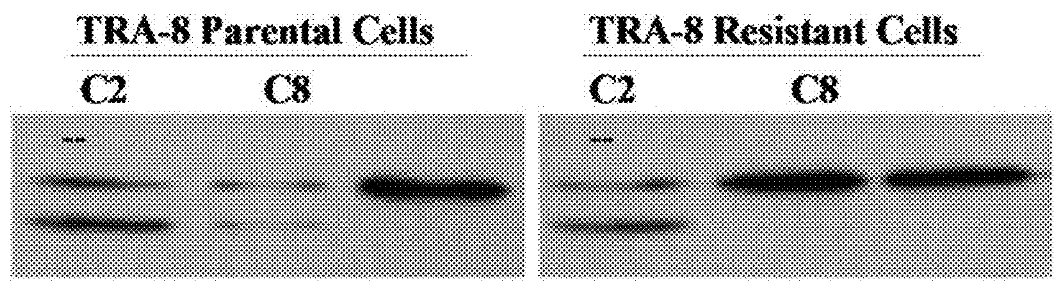
Figure 12E:
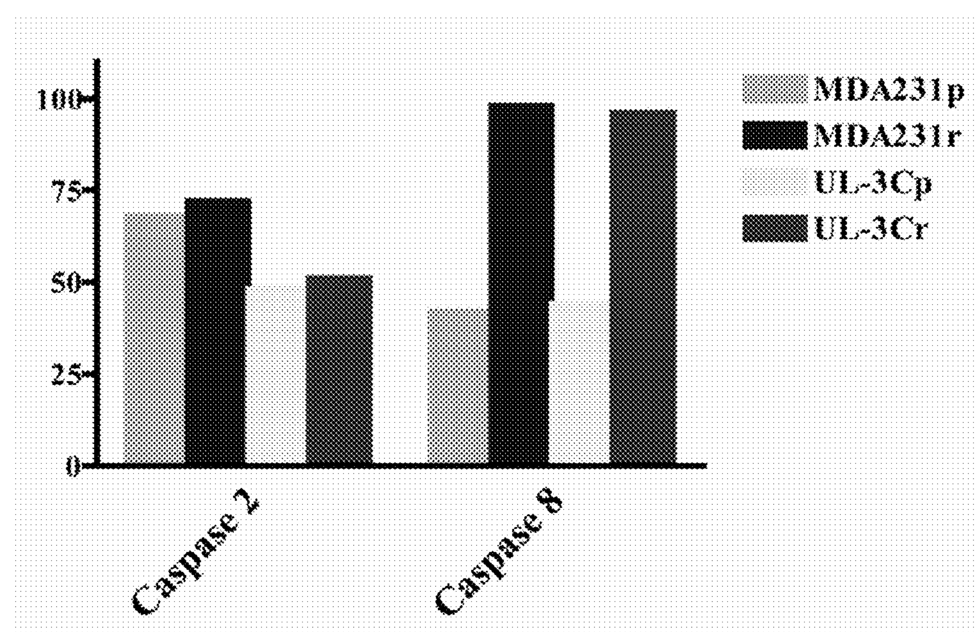
Figure 12F:
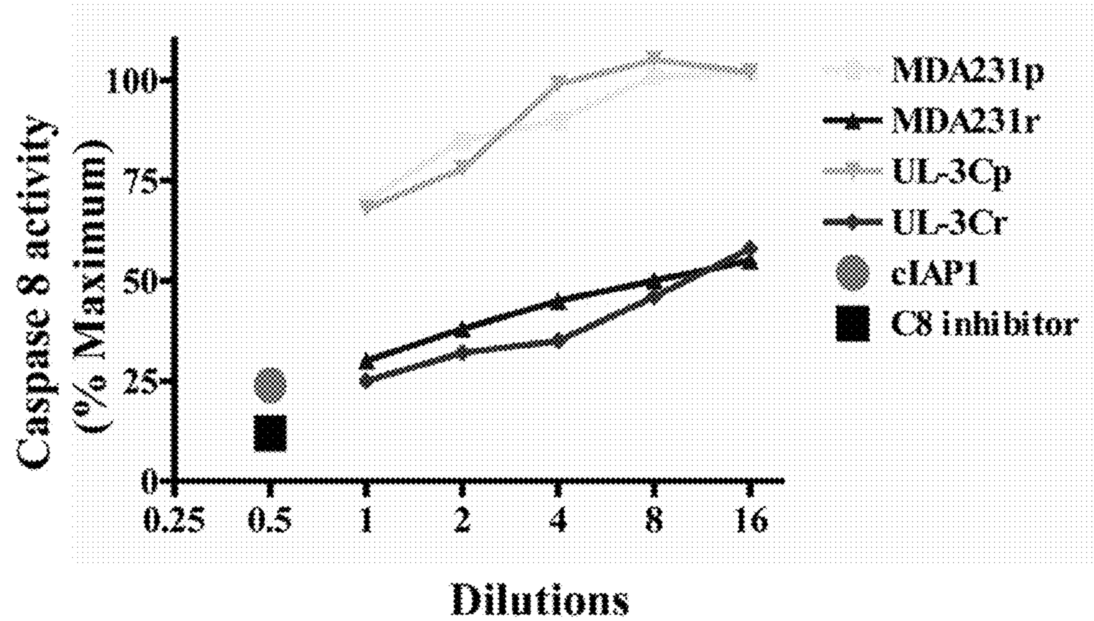

FIGS. 12A, 12B, 12C, 12D, 12E, and 12F show TRAIL-R2/DDX3/cIAP1 protein complexes block caspase-8 activation and DDX3 cleavage in TRA-8-resistant cells. FIG. 12 A shows TRAIL-R2/DDX3/cIAP1 protein complexes in TRA-8-sensitive and -resistant cells. MDA231 parental (MDA231p) and induced resistant (MDA231r) cells, UL-3C parental (UL-3 Cp) and induced resistant (UL-3Cr) cells were treated with 500 ng/ml TRA-8 for eight hours. Total cell lysates were immunoprecipitated with 2B4 anti-TRAIL-R2 antibody-conjugated sepharose 4B and eluted with glycine-HCl pH2.0 and immediately neutralized with 1M Tris buffer. ELISA plates were coated with 2B4 anti-TRAIL-R2 antibody and blocked with 3% BSA PBS. After incubation with the protein complex from the TRAIL-R2 co-IP, TRAIL-R2 was detected by biotin-conjugated polyclonal anti-TRAIL-R2 antibody, followed by HRP-conjugated streptavidin. FIG. 12B shows DDX3 was detected by biotin-conjugated 3E2, anti-DDX3 antibody, followed by HRP-conjugated streptavidin. FIG. 12C shows cIAP1 was detected by biotin-conjugated 1C12, anti-cIAP1 antibody, followed by HRP-conjugated streptavidin. FIG. 12D shows differential susceptibility of DDX3 to caspase-mediated cleavage. DDX3 was isolated from indicated cells by immunoprecipitation with 2B4 anti-TRAIL-R2 antibody-conjugated sepharose 4B, and incubated with indicated caspase-2 or caspase-8 at 37° C. from 4 hours. FIG. 12E shows the amount of DDX3 was measured by sandwich ELISA using 5A6 as capture and 3E2 as detection antibody. The results are presented as percentage of DDX3 after cleavage over non-cleaved controls. FIG. 12F shows effect of DDX3/cIAP1 complex on caspase 8 activity. DDX3 was isolated from the indicated cells by immunoprecipitation with 2B4 anti-TRAIL-R2 antibody-conjugated sepharose 4B, and incubated with recombinant active human caspase-8 in the presence of a fluorescent substrate of caspase-8, Ac-IETD-AMC, for 2 hours. The inhibition of caspase 8 was measured by decreased fluorescence intensity. The results are presented as percentage of maximum activity in control wells.

Figures 13A, 13B, 13C:
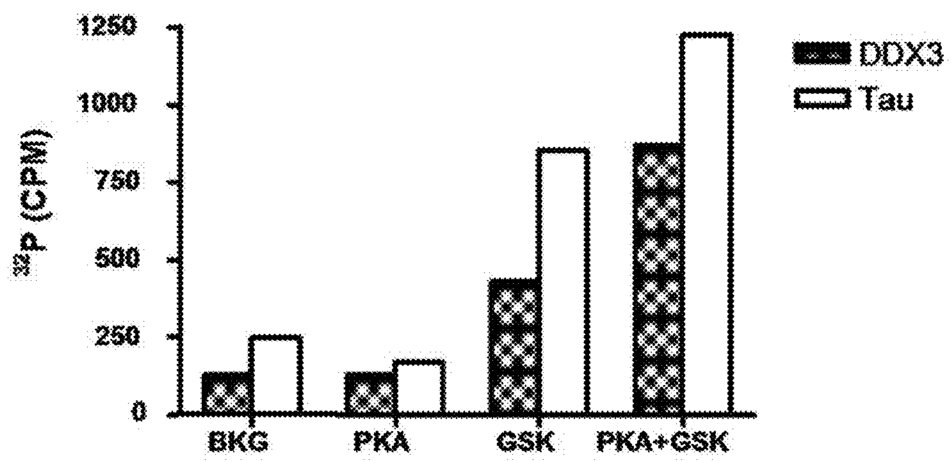
Figure 13D:
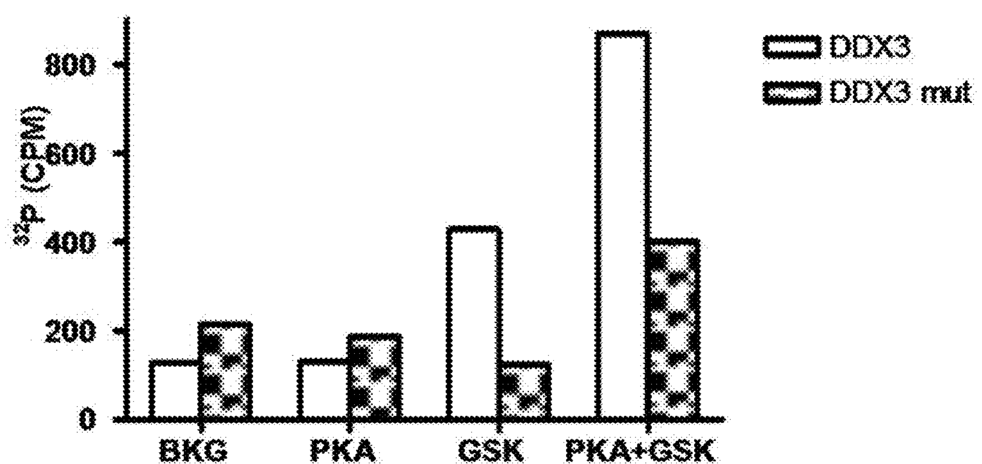
Figure 13E:
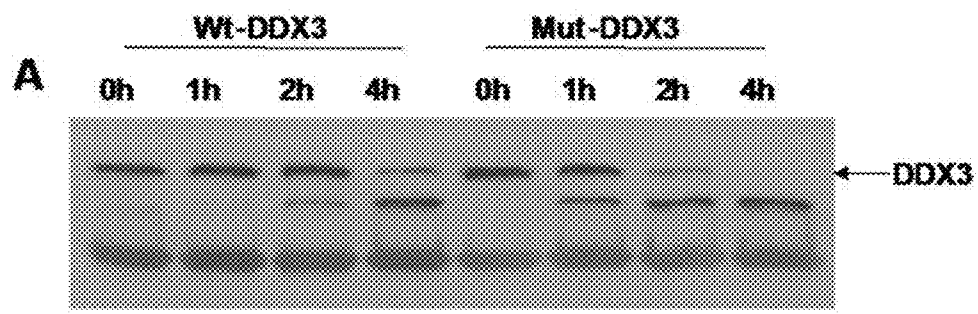
Figure 13F:
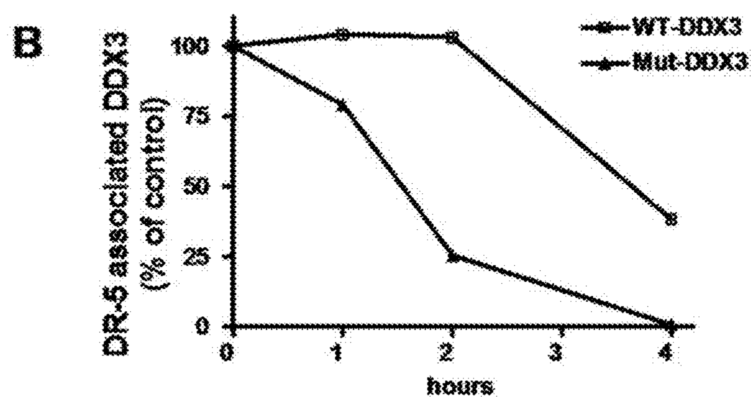

FIGS. 13A, 13B, 13C, 13D, 13E, and 13F show the role of the serine-rich domain of DDX3 in regulation of the association and cleavage. FIG. 13A shows a conserved domain for GSK3 substrate. FIG. 13B shows DDX3 co-immunoprecipitated by GSK3α. TRA-8 sensitive MDA231 cells were treated with TRA-8 with or without lithium for two hours. Total cell lysate was immunoprecipitated with anti-GSK3α beads. The proteins with GSK3α were analyzed by Western blot using anti-DDX3 antibody. GSK3 phosphorylates DDX3 (FIG. 13C). The recombinant DDX3 and tau were used as the substrates incubated with GSK with or without PKA for one hour. The incorporated 32P was counted and presented as cpm. FIG. 13D shows GSK3 fails to phosphorylate Ser90 mutant DDX3. FIG. 13E shows analysis of MDA231 cells transfected with wild-type DDX3 and Ser90 mutant DDX3. After TRA-8 treatment, the dissociation of DDX3 from DR5 and cleavage of DDX3 were determined (FIG. 13F).

DETAILED DESCRIPTION OF THE INVENTION

The disclosed method and compositions may be understood more readily by reference to the following detailed description of particular embodiments and the Example included therein and to the Figures and their previous and following description.

The induction of death receptor-mediated apoptosis of tumor cells is an extremely promising approach for cancer therapy. As in most, if not all, therapies, some target cells are resistant. As an example, TRA-8, a unique agonistic monoclonal anti-DR5 antibody, induces apoptosis of human cancer cells without hepatocyte cytotoxicity (Ichikawa, K., et al. 2001. Nat Med 7:954-960), exhibits strong anti-cancer efficacy in animal models (Buchsbaum, D. J., et al. 2003. Clin Cancer Res 9:3731-3741), and has demonstrated safety in toxicity studies in non-human primates. Thus, TRA-8 is used as an example herein but other agents that induce apoptosis through death receptor (e.g., DR4 or DR5) activation can be used in the methods taught herein. While TRA-8 and its humanized and human versions are under clinical development as an anti-cancer therapy, some tumor cell lines are resistant to TRA-8-mediated apoptosis despite reasonable levels of DR5 expression. These observations suggest that the resistance is not related to receptor expression but rather to DR5-initiated signaling mechanisms. Certainly DR5-mediated apoptosis can be enhanced significantly by common chemotherapeutic agents (Ohtsuka, T., and T. Zhou. 2002. J Biol Chem 277:29294-29303; Ohtsuka, T., D. et al. 2003. Oncogene 22:2034-2044). Disclosed are compositions and methods to inhibit resistance to death receptor agonists by targeting a family of CARD containing proteins that bind death receptors and inhibit caspase activation.

It is to be understood that the disclosed methods and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a vector is disclosed and discussed and a number of vector components including the promoters are discussed, each and every combination and permutation of promoters and other vector components and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

A variety of sequences are provided herein and these and others can be found in Genbank, at 'www.pubmed.gov'. Those of skill in the art understand how to resolve sequence discrepancies and differences and to adjust the compositions and methods relating to a particular sequence to other related sequences. Primers and/or probes can be designed for any sequence given the information disclosed herein and known in the art.

Provided is a method of reversing or preventing a target cell's resistance to a death receptor agonist comprising contacting the target cell with a modulator of one or more activities of a CARD containing proteins, wherein the modulation reverses or prevents resistance to the agonist. The method has utility for apoptosis signaling research and therapeutic treatment of diseases such as cancer and autoimmune and inflammatory disorders. Thus, the contacting step of the method can be performed in vivo or in vitro.

As used throughout, "reverse" or "reversing" means to change to the opposite position, direction, or course, such as in to change the course of a disease from that of getting worse to that of getting better. For example, in the case of death receptor resistance, to reverse a target cell's resistance to a death receptor agonist is to make the cell less resistant to said agonist. Thus, for example, reversing the resistance of a target cell that is 100% resistant can result in said target cell being 90% to 0% resistant to the death receptor agonist, including 90%, 85%, 80%, 75%, 70%, 65%, 60%, 55%, 50%, 45%, 40%, 35%, 30%, 25%, 20%, 15%, 10%, 5%, and 0% resistant.

As used throughout, "preventing" means to preclude, avert, obviate, forestall, stop, or hinder something from happening, especially by advance planning or action. For example, in the case of death receptor resistance, to prevent a target cell's resistance to a death receptor agonist is to make the cell less capable of becoming resistant to said agonist. Thus, for example, preventing 100% resistance in a target cell can result in said target cell being only 0% to 90% resistant to the death receptor agonist, including 0%, 5%, 10%, 15%, 20%, 25%, 30%, 35%, 40%, 45%, 50%, 55%, 60%, 65%, 70%, 75%, 80%, 85%, and 90% resistant.

"Reversing" or "preventing" refers to a change in magnitude or a delay in any change in magnitude. Thus, in the case of death receptor resistance, "reversing" or "preventing" includes reducing the course of increasing resistance or delaying an increase in resistance.

It must be noted that as used herein and in the appended claims, the singular forms "a", "an", and "the" include plural reference unless the context clearly dictates otherwise. Thus, for example, reference to "a polypeptide" includes a plurality of such polypeptides, reference to "the polypeptide" is a reference to one or more polypeptides and equivalents thereof known to those skilled in the art, and so forth.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

As used throughout, "target cell" means a cell bearing the targeted death receptor, including, for example, a cell that expresses DR5 or DR4 and illustratively includes abnormally growing cells and tumor cells such as papillomas and warts; breast cancer, colon cancer, hepatomas, leukemias, lung cancer, melanoma, myelomas, osteosarcomas, ovarian cancer, pancreatic cancer, prostate cancer, cancer of the head and neck, thyroid cancer, uterine cancer, tumors of the brain such as astrocytomas, activated immune cells (e.g., activated lymphocytes, lymphoid and myeloid cells), inflammatory cells, rheumatoid arthritis synovial cells, and virally infected cells. In vivo, the target cell is a cell of an individual with a pathological condition, including those in which cell proliferation is abnormal or dysregulated such as cancer and rheumatoid arthritis. Target cells include human, non-human primate, cats, dogs, rat, mouse, guinea pig, rabbit, goat, sheep, cow, horse, chicken, pig, marmoset and ferret cells, or cells of cells of various cell lines (e.g., Jurkat cells).

By "death receptor" is meant a receptor that induces cellular apoptosis once bound by a ligand. Death receptors include, for example, tumor necrosis factor (TNF) receptor superfamily members having death domains (e.g., TNFRI, Fas, DR3, 4, 5, 6) and TNF receptor superfamily members without death domains LTbetaR, CD40, CD27, HVEM.

Signal transduction through, for example, DR5 is a key mechanism in the control of DR5-mediated apoptosis. A common feature of the death receptors of the TNFR superfamily is that they all have a conserved "death domain" in their cytoplasm tail (Zhou, T., et al. 2002. Immunol Res 26:323-336). It is well established that DR5-mediated apoptosis is initiated at the death domain. Crosslinking of DR5 at cell surface by TRAIL or agonistic anti-DR5 antibody leads to oligomerization of DR5, which is immediately followed by the recruitment of FADD to the death domain of DR5 (Bodmer, J. L., et al. 2000. Nat Cell Biol 2:241-243; Chaudhary, P. M., et al. 1997. Immunity 7:821-830; Kuang, A. A., et al. 2000. J Biol Chem 275:25065-25068; Schneider, P., et al. 1997. Immunity 7:831-836; Sprick, M. R., et al. 2000 Immunity 12:599-609). The death-domain engaged FADD further recruits the initiator procaspase 8 and/or procaspase 10 to form a DISC through homophilic DD interactions (Krammer, P. H. 2000. Nature 407:789-795). The activated caspase 8 and 10 may activate caspase 3 directly, or cleave the BH3-containing protein Bid to activate a mitochondria-dependent apoptosis pathway through release of cytochrome C and caspase 9 activation (Desagher, S., and J. C. Martinou. 2000. Trends Cell Biol 10:369-377; Scaffidi, C., et al. 1998. Embo J 17:1675-1687). Following the formation of the death domain complex, several signal transduction pathways are activated such as caspase, NF-κB, and JNK/p38. Activation of these signaling pathways leads to regulation of death receptor-mediated apoptosis through the Bcl-2 and IAP family of proteins.

By "agonist" is meant a substance (molecule, drug, protein, etc.) that is capable of combining with a receptor (e.g. death receptor) on a cell and initiating the same reaction or activity typically produced by the binding of the endogenous ligand (e.g., apoptosis). The agonist of the present method can be a death receptor ligand. Thus, the agonist can be TNF, Fas Ligand, or TRAIL. The agonist can further be a fragment of these ligands comprising the death receptor binding domain such that the fragment is capable of binding and activating the death receptor. The agonist can further be a fusion protein comprising the death receptor binding domain such that the fusion protein is capable of binding and activating the death receptor. The agonist can further be a fusion protein comprising the death receptor binding domain such that the fusion protein is capable of binding and activating the death receptor. The agonist can further be a polypeptide having an amino acid sequence with at least 85% homology to TNF, Fas or TRAIL such that the homologue is capable of binding and activating the death receptor.

The agonist can further be an apoptosis-inducing antibody that binds the death receptor. The "antibody" can be monoclonal, polyclonal, chimeric, single chain, humanized, fully human antibody, or any Fab or F(ab')2 fragments thereof. By "apoptosis-inducing antibody" is meant an antibody that causes programmed cell death either before or after activation using the methods provided herein. Thus, the agonist of the present method can be an antibody specific for a Fas, TNFR1 or TRAIL death receptor, such that the antibody activates the death receptor. The agonist can be an antibody specific for DR4 or DR5. The agonist can be a DR5 antibody having the same epitope specificity, or secreted by, a mouse-mouse hybridoma having ATCC Accession Number PTA-1428 (e.g., the TRA-8 antibody), ATCC Accession Number PTA-1741 (e.g., the TRA-1 antibody), ATCC Accession Number PTA-1742 (e.g., the TRA-10 antibody The agonist can be an antibody having the same epitope specificity, or secreted by, the hybridoma having ATCC Accession Number PTA-3798 (e.g., the 2E12 antibody).

The TRAIL receptor targeted by the antibody of the present method can be DR4 or DR5. Such receptors are described in published patent applications WO99/03992, WO98/35986, WO98/41629, WO98/32856, WO00/66156, WO98/46642, WO98/5173, WO99/02653, WO99/09165, WO99/11791, WO99/12963 and published U.S. Pat. No. 6,313,269, which are all incorporated herein by reference in their entirety for the receptors taught therein. Monoclonal antibodies specific for these receptors can be generated using methods known in the art. See, e.g., Kohler and Milstein, Nature, 256:495-497 (1975) and Eur. J. Immunol. 6:511-519 (1976), both of which are hereby incorporated by reference in their entirety for these methods. See also methods taught in published patent application WO01/83560, which is incorporated herein by reference in its entirety.

The antibody of the present method can be an antibody known in the art, including, for example, a DR5 antibody having the same epitope specificity, or secreted by, a mouse-mouse hybridoma having ATCC Accession Number PTA-1428 (e.g., the TRA-8 antibody), ATCC Accession Number PTA-1741 (e.g., the TRA-1 antibody), ATCC Accession Number PTA-1742 (e.g., the TRA-10 antibody). Other examples include an antibody having the same epitope specificity, or secreted by, the hybridoma having ATCC Accession Number PTA-3798 (e.g., the 2E12 antibody).

By "CARD containing protein" is meant a family of proteins that contain a caspase-associated recruitment domain (CARD) and are characterized by the ability to bind a death receptor, wherein binding is optionally outside of the death domain, and modulate the activation of apoptosis by the death domain of said death receptor. DDX3 is a representative member of this family. The CARD containing proteins include RNA helicases of the DEAD (SEQ ID NO:21) box protein family. The disclosed CARD containing protein can be, for example, DDX3 (SEQ ID NO:25, accession no. gi:13514816), mda-5 (accession no. gi:11344593), or RIG-1 (accession no. gi:6048564). The CARD containing protein can further be a polypeptide having an amino acid sequence with at least 85% homology to DDX3, mda-5, or RIG-1.

The RNA helicases of the DEAD-box protein family are highly conserved from bacteria to mammals, are involved in a variety of metabolic processes involving RNA, and are crucial for cell survival (Heinlein, U. A. 1998. J Pathol 184:345-347). All members of this family of proteins have an ATPase motif that is composed of the characteristic amino acid sequence D-E-A-D (Asp-Glu-Ala-Asp, SEQ ID NO: 21), giving the name to this family. It is generally believed that DEAD (SEQ ID NO:21) box proteins are RNA helicases, as ribonucleic acid binding proteins, required for translation initiation, RNA splicing, ribosomal assembly, RNA degradation, mRNA stability and RNA editing. While some of these RNA helicases play a crucial role in the translation of special transcriptional factors, the over-expression of some is related to carcinogenesis. DDX1 is co-amplified with N-myc in neuroblastomas (George, R. E., et al. 1996. Oncogene 12:1583-1587; Godbout, R., et al. 1998. J Biol Chem 273:21161-21168). The RNA helicase, p68, is consistently overexpressed in tumors as compared with matched normal tissue. The accumulated p68 appears to be poly-ubiquitinated, suggesting a possible defect in proteasome-mediated degradation in these tumors (Causevic, M., et al. 2001. Oncogene 20:7734-7743), suggesting that the dysregulation of p68 expression occurs early during tumor development. The rck/p54 of the DEAD (SEQ ID NO:21) box protein/RNA helicase family may contribute to cell proliferation and carcinogenesis in the development of human colorectal tumors at the translational level by increasing synthesis of c-myc protein (Hashimoto, K., et al. 2001. Carcinogenesis 22:1965-1970). DDX3 is a member of this family although the RNA helicase function of DDX3 is unknown (Fu, J. J., et al. 2002. Sheng Wu Hua Xue Yu Sheng Wu Wu Li Xue Bao (Shanghai) 34:655-661). It has been reported that DDX3 could interact with the HCV core protein and regulate the translation of the HCV viral proteins (Owsianka, A. M., and A. H. Patel. 1999. Virology 257:330-3400).

Some of the RNA helicases contain a conserved CARD (caspase recruitment domain; Yoneyama, M., et al. 2004. Nat Immunol 5:730-737; Kang, D. C., et al. 2004. Oncogene 23:1789-1800; Kang, D. C., et al. 2002. Proc Natl Acad Sci USA 99:637-642). Subtraction hybridization identified melanoma differentiation-associated gene-5 (mda-5) as a gene induced during differentiation, cancer reversion, and programmed cell death (apoptosis). This gene contains both a caspase recruitment domain and putative DExH group RNA helicase domains. Mda-5 may function as a mediator of IFN-induced growth inhibition and/or apoptosis (Kang, D. C., et al. 2002. Proc Natl Acad Sci USA 99:637-642). A more recent study indicates that the level of mda-5 mRNA is low in normal tissues, whereas expression is induced in a spectrum of normal and cancer cells by IFN-beta. Expression of mda-5 by means of a replication incompetent adenovirus, Ad.mda-5, induces apoptosis in HO-1 cells as confirmed by morphologic, biochemical and molecular assays (Kang, D. C., et al. 2004. Oncogene 23:1789-1800). The retinoic acid inducible gene I (RIG-I), which encodes a DExD/H box RNA helicase that contains a caspase recruitment domain, is an essential regulator of dsRNA-induced signaling, as assessed by functional screening and assays. A helicase domain with intact ATPase activity was responsible for the dsRNA-mediated signaling. The caspase recruitment domain transmitted 'downstream' signals, resulting in the activation of transcription factors NF-κB and IRF-3. Subsequent gene activation by these factors induced antiviral functions, including type I interferon production (Yoneyama, M., et al. 2004. Nat Immunol 5:730-737).

Proteins containing a caspase-associated recruitment domain (CARD) have been established as key regulators of cell death. CARD is composed of a conserved alpha-helical bundle found in the N-terminal of pro-domains of certain caspases. CARDs can also be found in a variety of other proteins. Like the death domain proteins, CARDs function as homotypic protein interaction motifs that allow the communications of proteins via CARD/CARD interactions. The proteins with a CARD can be either pro-apoptotic or anti-apoptotic. The pro-apoptotic CARD proteins include certain caspases such as caspase 2, 4, and 9, and Apaf1, which play important roles in the initiation of apoptosis. The representative anti-apoptotic CARD proteins include cIAP1 and cIAP2, which interact with the CARD of caspases, and inhibit caspase activation via their BIR domain. Many aspects of the function of this family of proteins point to their potential utility as novel drug targets in the treatment of cancer. Several CARD containing proteins are critical components of the conserved cell death machinery which, when dysregulated, promotes oncogenesis and contributes prominently to tumor resistance to chemotherapy. The pro-apoptotic protein Apaf1, which is inactivated in some cancers, is a CARD protein that is indispensable for mitochondria-induced apoptosis. Other anti-apoptotic CARD proteins, such as the proteins of the TAP family, have been shown to protect tumors from cell death stimuli and to be over-expressed in certain forms of cancer. Therapeutics that activate or inhibit CARD proteins can therefore be utilized as chemo-sensitizing agents or as modulators of apoptosis when used in conjunction with conventional chemotherapy.

Resistance to death receptor agonists can be attributed to the activity of the disclosed CARD containing proteins. The present method therefore provides a composition that modulates one or more activities of the CARD containing protein to prevent said resistance. By "modulates" is meant the upregulation, downregulation, activation, antagonism, or otherwise alteration in form or function. "Activities" of a protein include, for example, transcription, translation, intracellular translocation, secretion, phosphorylation by kinases, cleavage by proteases, homophilic and heterophilic binding to other proteins, ubiquitination. As the activity of the CARD containing protein is due in part to phosphorylation at or near the death receptor binding amino acids, the provided modulator can be an inhibitor of CARD containing protein phosphorylation. Thus, the modulator can be an inhibitor of a kinase or phosphatase. As an example, the modulator can be an inhibitor of glycogen synthase kinase-3 (GSK-3) activity.

GSK-3 is a protein kinase found in a variety of organisms, including mammals. Two nearly identical forms of GSK-3 exist: GSK-3a and GSK-3β. The inhibitor can be any known or newly discovered GSK-3 inhibitor. Optimally, the GSK-3 inhibitor of the provided method inhibits at least GSK-3β. The amino acid sequence for human GSK-3β can be accessed at Genbank accession number P49841, and the corresponding nucleotide sequence at accession number NM_002093. For experimental and screening purposes, it may be desirable to use an animal model. For example, the rat GSK-3β sequence may be accessed at Genbank accession number P18266, and the mouse at Genbank accession number AAD39258.

GSK-3 inhibitors, as used herein, are compounds that directly or indirectly reduce the level of GSK-3 activity in a cell, by competitive or non-competitive enzyme inhibition; by decreasing protein levels, e.g. by a targeted genetic disruption, reducing transcription of the GSK-3 gene, increasing protein instability, etc Inhibitors may be small organic or inorganic molecules, anti-sense nucleic acids, antibodies or fragments derived therefrom, etc. Other inhibitors of GSK-3 can be found through screening combinatorial or other chemical libraries for the inhibition of GSK-3 activity.

Examples of direct inhibitors of GSK-3 protein include lithium ($Li^+$) (Klein et al. 1996), which potently inhibits GSK-3β activity ($K_i$=2 mM), but is not a general inhibitor of other protein kinases. Beryllium ions ($Be^{2+}$) are stronger inhibitors of GSK-3, inhibiting in the micromolar range. However, this inhibitory effect is not as selective as lithium because it will also inhibit CDK1 at low doses.

GSK-3 inhibitors also include aloisine, aloisine A, kenpaullone. Aloisine (7-n-Butyl-6-(4-methoxyphenyl)[5H]pyrrolo[2,3-b]pyrazine) is a potent, selective, cell-permeable and ATP-competitive inhibitor of Cdk1/B (IC50=700 nM), Cdk5/p35 (IC50=1.5 uM) and GSK-3 (IC50=920 nM) (Mettey Y, et al. (2003) J Med. Chem. 46(2):222-36), incorporated herein by reference in its entirety for teachings related to this molecule. Aloisine A (7-n-Butyl-6-(4-hydroxyphenyl)[5H]pyrrolo[2,3-b]pyrazine) is a cell-permeable compound that acts as a potent, selective, reversible, and ATP-competitive inhibitor of cyclin dependent kinases, c-Jun N-terminal kinase (JNK), and glycogen synthase kinase-3 (GSK-3) (GSK-3 alpha, IC50=500 nM) (GSK-3 beta, IC50=1.5 uM) (Mettey Y, et al. (2003) J Med. Chem. 46(2):222-36), incorporated herein by reference in its entirety for teachings related to this molecule. Kenpaullone (9-Bromo-7,12-dihydroindolo[3,2-d][1]benzazepin-6(5H)-one) is a potent, cell-permeable inhibitor of glycogen synthase kinase-3b (GSK3b, IC50=230 nM), Lck and cyclin-dependent kinases (Cdks) (Schultz C, et al. (1999) J. Med. Chem. 42(15):2909-19; Zaharevitz D W, et al (1999) Cancer Res. 59(11):2566-9; Kunick C, et al. (2004) J. Med. Chem. 47(1):22-36), which are all incorporated herein by reference in their entirety for teachings related to this molecule.

A number of other compounds have been found to inhibit GSK-3. The majority inhibit kinase activity through interaction with the ATP-binding site. They include Bisindole- and Anilino maleimides, Aldisine alkaloids, Paullones, Indirubins and Pyraloquinoxalines. For example, Paullones and their use in GSK-3 inhibition is described, for example, in Kunick C, et al. J Med. Chem. 2004 Jan. 1; 47(1):22-36, which is hereby incorporated by reference herein in its entirety for its teaching of Paullones. Such compounds are effective at nanomolar concentrations in vitro and low micromolar in vivo. Again, whilst many have been shown to be potent, they are not very specific to GSK-3 and commonly inhibit the related CDKs at similar levels. However, two structurally distinct maleimides (SB216763 and SB415286) have been shown to be potent and to have high specificity for GSK-3. They can effectively substitute for lithium as GSK-3 inhibitors in cell studies. Members of the class of compounds termed granulatimides or didemnimides have also been found to act as GSK-3 inhibitors (International patent application WO 99/47522, which is hereby incorporated herein for its teaching of these compounds).

Some indirect inhibitors of GSK-3 include wortmannin, which activates protein kinase B, resulting in the phosphorylation and inhibition of GSK-3. Isoproterenol, acting primarily through beta3-adrenoreceptors, decreases GSK-3 activity to a similar extent (approximately 50%) as insulin (Moule et al. 1997). p70 S6 kinase and p90rsk-1 also phosphorylate GSK-3β, resulting in its inhibition.

GSK-3 can also be selectively targeted using GSK-3-specific peptides. For example, frequently rearranged in advanced T-cell lymphomas 1 (FRAT1) is a mammalian homologue of a GSK3-binding protein (GBP). FRATtide (a peptide corresponding to residues 188-226 of FRAT1) binds to GSK3 and blocks the GSK3-catalysed phosphorylation of Axin and beta-catenin (Thomas G M, et al. FEBS Lett. 1999 Sep. 17; 458(2):247-51).

The GSK-3 inhibitor of the provided method can also be a functional nucleic acid. Functional nucleic acids are nucleic acid molecules that have a specific function, such as binding a target molecule or catalyzing a specific reaction. Functional nucleic acid molecules can be divided into the following categories, which are not meant to be limiting. For example, functional nucleic acids include antisense molecules, aptamers, ribozymes, triplex forming molecules, RNAi, and external guide sequences. The functional nucleic acid molecules can act as affectors, inhibitors, modulators, and stimulators of a specific activity possessed by a target molecule, or the functional nucleic acid molecules can possess a de novo activity independent of any other molecules.

Figure 9A:
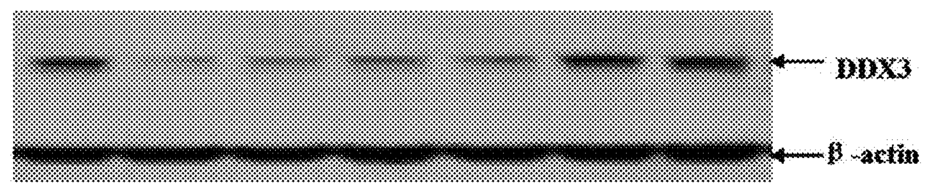
FIGS. 9A, 9B, 9C, 9D, 9E, 9F, and 9G show Down-regulation of DDX3 reverses resistance to TRA-8-induced apoptosis.
Figure 9B:
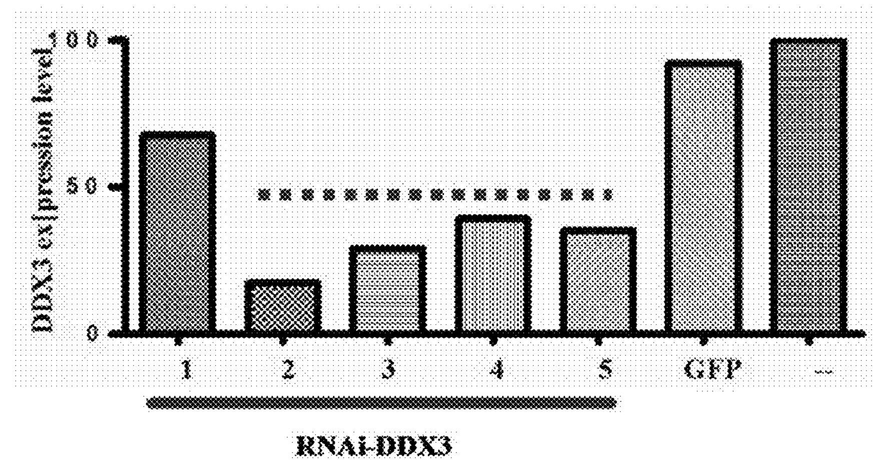
Figure 9C:
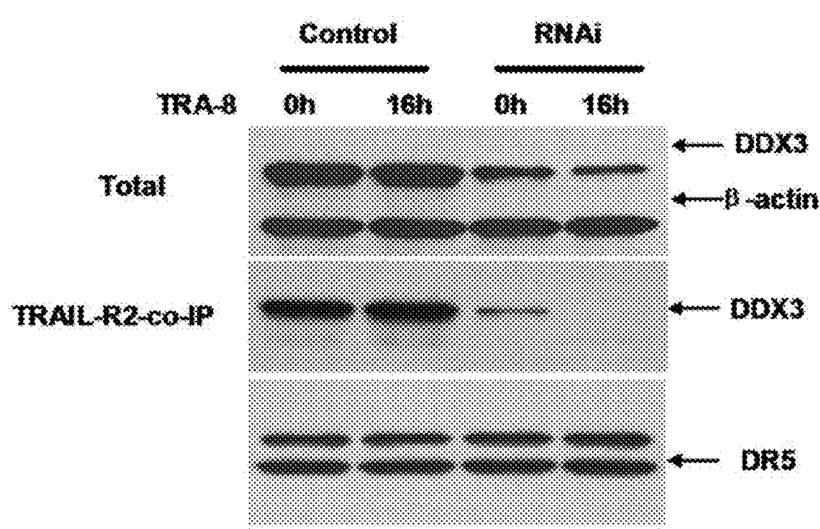
Figure 9D:
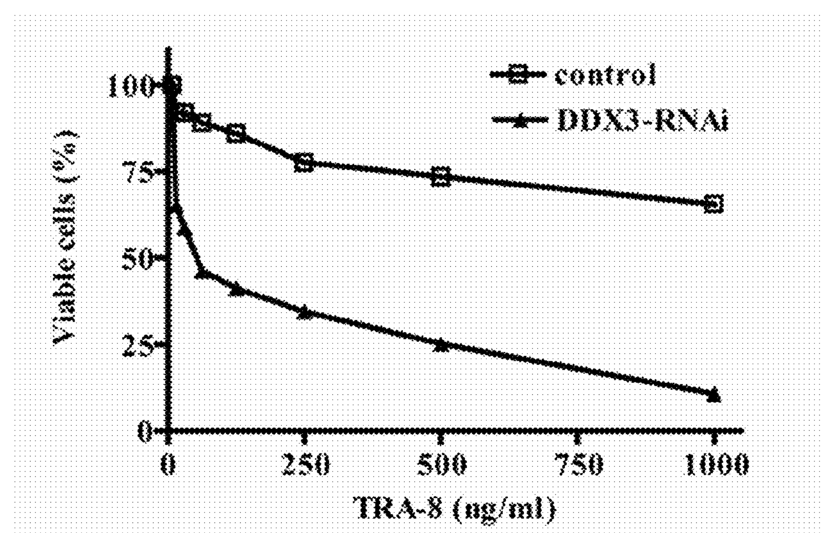
Figure 9E:
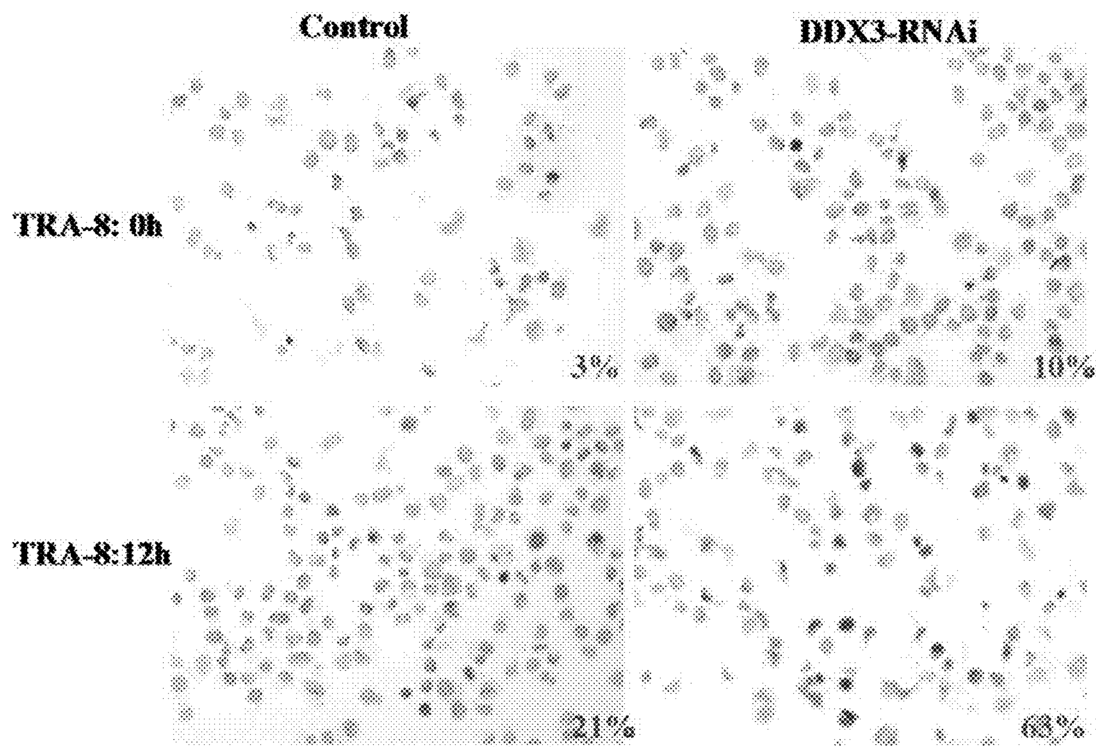

As CARD containing proteins can be cleaved during death receptor-induced apoptosis, the modulator of the present method can act by promoting cleavage of the CARD containing protein. As an example, DDX3 is disassociated from DR5 and cleaved during TRA-8-induced apoptosis (FIGS. 9A and C) in parallel with the recruitment of FADD (FIG. 9E). One of the cleavage sites for DDX3 is a relatively conserved DEDD (SEQ ID NO:7) motif between amino acid residues 132-135, which can be cleaved by caspases 2, 3, 7 or 10. Thus, the modulator can be a caspase or a derivative of a caspase that cleaves a CARD containing protein (e.g. DDX3).

As the activity of the CARD containing protein is dependent upon its binding to the death receptor, the modulator of the present method can be an inhibitor of the interaction between the CARD containing protein and the death receptor. In one instance, the modulator is a substance (drug, molecule, polypeptide, etc.) that binds a CARD containing protein at the death receptor-binding site. Thus, the modulator can be a polypeptide comprising the amino acids of the death receptor corresponding to the binding site of the CARD containing protein. For example, the modulator can be a polypeptide comprising amino acids 250-340 of DR5 (SEQ ID NO:22, accession no. gi:3721878). Thus, the modulator can comprise the amino acid sequence SEQ ID NO:23. The modulator can further be a polypeptide comprising a fragment of amino acid sequence SEQ ID NO:23, such that the fragment is capable of binding DDX3. As an example, the modulator can be a polypeptide comprising amino acids 280-310 of DR5 (SEQ ID NO:22, accession no. gi:3721878). Thus, the modulator can comprise the amino acid sequence SEQ ID NO:24. As another example, the modulator can be a polypeptide comprising amino acids 300-330 of DR5 (SEQ ID NO:22, accession no. gi:3721878). Thus, the modulator can comprise the amino acid sequence SEQ ID NO:36.

Alternatively, the modulator can be a substance (drug, molecule, polypeptide, etc.) that binds the CARD containing protein binding site of the death receptor without inhibiting apoptosis. The modulator can be a polypeptide comprising the amino acids corresponding to the death receptor-binding site of the CARD containing protein.

The modulator of the present method can affect the ability of a CARD containing protein to prevent the activation of capase-dependent apoptosis. The CARD domain of CARD containing proteins is involved in the recruitment of inhibitors of apoptosis (IAP), which suppress apoptosis in host cells during viral infection (Crook, N. E., et al. 1993. J Virol 67:2168-2174). The IAP family antagonizes cell death by interacting with and inhibiting the enzymatic activity of mature caspases. Eight distinct mammalian IAPs have been identified, including XIAP, c-IAP1, c-IAP2, and ML-IAP/Livin (see, for example, Ashhab, Y., et al. 2001. FEBS Lett 495:56-60; Kasof, G. M., and B. C. Gomes. 2001. J Biol Chem 276:3238-3246; Vucic, D., et al. 2000. Curr Biol 10:1359-1366, which are all incorporated herein by references in their entirety as related to these IAP molecules). All IAPs contain one to three baculovirus IAP repeat (BIR) domains and have homologous sequence (CX2CX16HX6C). Through the BIR domain, IAP molecules bind and directly inhibit caspases (Deveraux, Q. L., and J. C. Reed. 1999. Genes Dev 13:239-252; Deveraux, Q. L., et al. 1997. Nature 388:300-304; Deveraux, Q. L., and J. C. Reed. 1999. Genes Dev 13:239-252, which are all incorporated herein by references in their entirety as related to the interaction of IAPs and caspases). The mitochondrial proteins Smac/DIABLO could bind to and antagonize IAPs (Suzuki, Y., et al. 2001. J Biol Chem 276:27058-27063) to suppress IAP function (Wieland, I., et al. 2000. Oncol Res 12:491-500) (The cited references are all incorporated herein by references in their entirety as related to the inhibition of IAPs). Thus, the modulator of the present method can be an inhibitor of CARD-dependent binding. The modulator can affect the ability of a CARD containing protein to recruit a caspase or modulator of caspase such as IAP. The modulator can be a substance (drug, molecule, polypeptide, fusion protein, antibody, antibody fragment, etc.) that binds a CARD containing protein such that the CARD containing protein has reduced binding and recruitment of IAPs. The modulator can be a CARD containing protein-binding fragment of, for example, caspase-1, caspase-2, caspase-4 or caspase-5, cIAP1, cIAP2, XIAP, or survivin.

The modulator can further be an inhibitor of IAP or CARD containing protein gene expression in the target cell. There are various known methods of inhibiting the expression of a protein in a cell, including triplex forming molecules, ribozymes, external guide sequences, antisense molecules, and RNAi molecules.

Antisense molecules are designed to interact with a target nucleic acid molecule through either canonical or non-canonical base pairing. The interaction of the antisense molecule and the target molecule is designed to promote the destruction of the target molecule through, for example, RNAseH mediated RNA-DNA hybrid degradation. Alternatively the antisense molecule is designed to interrupt a processing function that normally would take place on the target molecule, such as transcription or replication. Antisense molecules can be designed based on the sequence of the target molecule. Numerous methods for optimization of antisense efficiency by finding the most accessible regions of the target molecule exist. Exemplary methods would be in vitro selection experiments and DNA modification studies using DMS and DEPC. It is preferred that antisense molecules bind the target molecule with a dissociation constant ($K_d$) less than or equal to 10-6, 10-8, 10-10, or 10-12. A representative sample of methods and techniques which aid in the design and use of antisense molecules can be found in U.S. Pat. Nos. 5,135,917, 5,294,533, 5,627,158, 5,641,754, 5,691,317, 5,780,607, 5,786,138, 5,849,903, 5,856,103, 5,919,772, 5,955,590, 5,990,088, 5,994,320, 5,998,602, 6,005,095, 6,007,995, 6,013,522, 6,017,898, 6,018,042, 6,025,198, 6,033,910, 6,040,296, 6,046,004, 6,046,319, and 6,057,437, which are herein incorporated by reference in their entirety for methods and techniques regarding antisense molecules.

Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules, such as ATP (U.S. Pat. No. 5,631,146) and theophiline (U.S. Pat. No. 5,580,737), as well as large molecules, such as reverse transcriptase (U.S. Pat. No. 5,786,462) and thrombin (U.S. Pat. No. 5,543,293). Aptamers can bind very tightly with $K_d$s from the target molecule of less than $10^{-12}$ M. It is preferred that the aptamers bind the target molecule with a $K_d$ less than $10^{-6}$, $10^{-8}$, $10^{-10}$, or $10^{-12}$. Aptamers can bind the target molecule with a very high degree of specificity. For example, aptamers have been isolated that have greater than a 10,000 fold difference in binding affinities between the target molecule and another molecule that differ at only a single position on the molecule (U.S. Pat. No. 5,543,293). It is preferred that the aptamer have a $K_d$ with the target molecule at least 10, 100, 1000, 10,000, or 100,000 fold lower than the $K_d$ with a background binding molecule. It is preferred when doing the comparison for a polypeptide for example, that the background molecule be a different polypeptide. Representative examples of how to make and use aptamers to bind a variety of different target molecules can be found in U.S. Pat. Nos. 5,476,766, 5,503,978, 5,631,146, 5,731,424, 5,780,228, 5,792,613, 5,795,721, 5,846,713, 5,858,660, 5,861,254, 5,864,026, 5,869,641, 5,958,691, 6,001,988, 6,011,020, 6,013,443, 6,020,130, 6,028,186, 6,030,776, and 6,051,698, which are herein incorporated by reference in their entirety for methods and techniques regarding aptamers.

Ribozymes are nucleic acid molecules that are capable of catalyzing a chemical reaction, either intramolecularly or intermolecularly. Ribozymes are thus catalytic nucleic acid. It is preferred that the ribozymes catalyze intermolecular reactions. There are a number of different types of ribozymes that catalyze nuclease or nucleic acid polymerase type reactions which are based on ribozymes found in natural systems, such as hammerhead ribozymes, (U.S. Pat. Nos. 5,334,711, 5,436,330, 5,616,466, 5,633,133, 5,646,020, 5,652,094, 5,712,384, 5,770,715, 5,856,463, 5,861,288, 5,891,683, 5,891,684, 5,985,621, 5,989,908, 5,998,193, 5,998,203; International Patent Application Nos. WO 9858058 by Ludwig and Sproat, WO 9858057 by Ludwig and Sproat, and WO 9718312 by Ludwig and Sproat) hairpin ribozymes (for example, U.S. Pat. Nos. 5,631,115, 5,646,031, 5,683,902, 5,712,384, 5,856,188, 5,866,701, 5,869,339, and 6,022,962), and tetrahymena ribozymes (for example, U.S. Pat. Nos. 5,595,873 and 5,652,107). There are also a number of ribozymes that are not found in natural systems, but which have been engineered to catalyze specific reactions de novo (for example, U.S. Pat. Nos. 5,580, 967, 5,688,670, 5,807,718, and 5,910,408). Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence. Representative examples of how to make and use ribozymes to catalyze a variety of different reactions can be found in U.S. Pat. Nos. 5,646,042, 5,693,535, 5,731,295, 5,811,300, 5,837,855, 5,869,253, 5,877,021, 5,877,022, 5,972,699, 5,972,704, 5,989,906, and 6,017,756.

Triplex forming functional nucleic acid molecules are molecules that can interact with either double-stranded or single-stranded nucleic acid. When triplex molecules interact with a target region, a structure called a triplex is formed, in which there are three strands of DNA forming a complex dependant on both Watson-Crick and Hoogsteen base-pairing. Triplex molecules are preferred because they can bind target regions with high affinity and specificity. It is preferred that the triplex forming molecules bind the target molecule with a $K_d$ less than 10-6, 10-8, 10-10, or 10-12. Representative examples of how to make and use triplex forming molecules to bind a variety of different target molecules can be found in U.S. Pat. Nos. 5,176,996, 5,645, 985, 5,650,316, 5,683,874, 5,693,773, 5,834,185, 5,869,246, 5,874,566, and 5,962,426.

External guide sequences (EGSs) are molecules that bind a target nucleic acid molecule forming a complex, and this complex is recognized by RNase P, which cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. (WO 92/03566 by Yale, and Forster and Altman, Science 238:407-409 (1990)).

Similarly, eukaryotic EGS/RNAse P-directed cleavage of RNA can be utilized to cleave desired targets within eukarotic cells. (Yuan et al., Proc. Natl. Acad. Sci. USA 89:8006-8010 (1992); WO 93/22434 by Yale; WO 95/24489 by Yale; Yuan and Altman, EMBO J. 14:159-168 (1995), and Carrara et al., Proc. Natl. Acad. Sci. (USA) 92:2627-2631 (1995)). Representative examples of how to make and use EGS molecules to facilitate cleavage of a variety of different target molecules be found in U.S. Pat. Nos. 5,168,053, 5,624,824, 5,683,873, 5,728,521, 5,869,248, and 5,877,162.

Gene expression can also be effectively silenced in a highly specific manner through RNA interference (RNAi). This silencing was originally observed with the addition of double stranded RNA (dsRNA) (Fire, A., et al. (1998) Nature, 391:806-11; Napoli, C., et al. (1990) Plant Cell 2:279-89; Hannon, G. J. (2002) Nature, 418:244-51). Once dsRNA enters a cell, it is cleaved by an RNase III-like enzyme, Dicer, into double stranded small interfering RNAs (siRNA) 21-23 nucleotides in length that contains 2 nucleotide overhangs on the 3' ends (Elbashir, S. M., et al. (2001) Genes Dev., 15:188-200; Bernstein, E., et al. (2001) Nature, 409:363-6; Hammond, S. M., et al. (2000) Nature, 404:293-6). In an ATP dependent step, the siRNAs become integrated into a multi-subunit protein complex, commonly known as the RNAi induced silencing complex (RISC), which guides the siRNAs to the target RNA sequence (Nykanen, A., et al. (2001) Cell, 107:309-21). At some point the siRNA duplex unwinds, and it appears that the antisense strand remains bound to RISC and directs degradation of the complementary mRNA sequence by a combination of endo and exonucleases (Martinez, J., et al. (2002) Cell, 110:563-74). However, the effect of iRNA or siRNA or their use is not limited to any type of mechanism.

Short Interfering RNA (siRNA) is a double-stranded RNA that can induce sequence-specific post-transcriptional gene silencing, thereby decreasing or even inhibiting gene expression. In one example, an siRNA triggers the specific degradation of homologous RNA molecules, such as mRNAs, within the region of sequence identity between both the siRNA and the target RNA. For example, WO 02/44321 discloses siRNAs capable of sequence-specific degradation of target mRNAs when base-paired with 3' overhanging ends, herein incorporated by reference for the method of making these siRNAs. Sequence specific gene silencing can be achieved in mammalian cells using synthetic, short double-stranded RNAs that mimic the siRNAs produced by the enzyme dicer (Elbashir, S. M., et al. (2001) Nature, 411:494 498) (Ui-Tei, K., et al. (2000) FEBS Lett 479:79-82). siRNA can be chemically or in vitro-synthesized or can be the result of short double-stranded hairpin-like RNAs (shRNAs) that are processed into siRNAs inside the cell. Synthetic siRNAs are generally designed using algorithms and a conventional DNA/RNA synthesizer. Suppliers include Ambion (Austin, Tex.), ChemGenes (Ashland, Mass.), Dharmacon (Lafayette, Colo.), Glen Research (Sterling, Va.), MWB Biotech (Esbersberg, Germany), Proligo (Boulder, Colo.), and Qiagen (Vento, The Netherlands). siRNA can also be synthesized in vitro using kits such as Ambion's SILENCER® siRNA Construction Kit. Disclosed herein are any siRNA designed as described above based on the sequences for c-Kit or SCF. For example, siRNAs for silencing gene expression of c-Kit is commercially available (SURESILENCING™ Human c-Kit siRNA; Zymed Laboratories, San Francisco, Calif.).

The production of siRNA from a vector is more commonly done through the transcription of a short hairpin RNAs (shRNAs). Kits for the production of vectors comprising shRNA are available, such as, for example, Imgenex's GENESUPPRESSOR™ Construction Kits and Invitrogen's BLOCK-IT™ inducible RNAi plasmid and lentivirus vectors. Disclosed herein are any shRNA designed as described above based on the sequences for the herein disclosed inflammatory mediators.

Thus, the modulator of the present method can comprise siRNA or shRNA. The modulator can be an inhibitor of cIAP1 (accession no. gi:41349435, cIAP2 (accession no. gi:33946283, XIAP (accession no gi:1184319), survivin (accession no gi:2315862), DDX3 (SEQ ID NO:25, accession no. gi:13514816), mda-5 (accession no. gi:11344593), or RIG-1 (accession no. gi:6048564) gene expression. Thus, the modulator can comprise a shRNA derived from the nucleic acid sequence of DDX3 (SEQ ID NO:25, accession no. gi:13514816). As an example, the modulator can comprise a shRNA encoded by the nucleic acid sequence SEQ ID NO:10, 12, 14, or 16.

There are several transfection reagents that can be used for the delivery of siRNA to a cell, such as, for example, Invitrogen's Lipofectamine 2000, Mirus' TransIT-TKO, and Novagen's RiboJuice siRNA Transfection Reagent. However, transfection reagents generally do not work in vivo. Naked siRNA can be delivered directly into the vasculature of a subject, which has the advantage that no other proteins are delivered or expressed, which is critical as nucleic acids are not immunogenic. There are also methods of delivering nucleic acids across epithelial barriers such as the skin using some form of energy to disrupt the epithelium, e.g. sonophoresis (U.S. Pat. No. 5,421,816, U.S. Pat. No. 5,618,275, U.S. Pat. No. 6,712,805 and U.S. Pat. No. 6,487,447, which are all incorporated herein by reference for their teaching of ultrasound mediated delivery of compounds through the skin).

Provided is a method of screening a cell for a biomarker of resistance to a death receptor agonist comprising assaying the cell for total DDX3, or a homologue thereof. Also, provided is a method of screening a cell for a biomarker of resistance to a death receptor agonist comprising assaying the association of the death receptor and a CARD containing protein, wherein high levels of association signify resistance to the agonist. Association between the death receptor and CARD containing protein indicates resistance to the agonist. Optionally, the cell to be screened is pre-contacted with a death receptor agonist (e.g. agonistic antibody). Thus, provided is a method of screening a cell for a biomarker of resistance to a death receptor agonist comprising contacting the cell with the death receptor agonist and monitoring the fractional association of the death receptor and a CARD containing protein, wherein association signifies resistance to the agonist. Optionally, in the various methods involving detecting association, one could measure dissociation and substract the dissociated amount from the total to calculate the associated amount.

The contacting step of the present method can be done either in vivo or in vitro. Monitoring of the association between the death receptor and CARD containing protein can involve the isolation of a protein fragment (e.g. death receptor) from the cell(s) using specific antibodies (e.g. by immunoprecipitation). This method can further involve the analysis of the protein fragment for associated proteins (e.g. DDX3) by standard immunodetection methods, such as Western blot, radioimmunoassay (RIA), or ELISA. These antibody-based methods are well known in the art and are easily tailored to each death receptor, CARD containing protein, caspase and modulator of caspase of interest. As an illustration, the present method can comprise treating a cell from a subject with TRA-8 antibody, isolating the protein from the cell lysate, immunoprecipitating DR5 protein, separating DR5 by SDS-polyacrylamide gel electrophoresis (SDS-PAGE) (reducing or non-reducing conditions), transferring the separated protein to a nitrocellulose membrane, and using standard Western blot techniques to detect DDX3 associated with DR5, wherein the association is evidence of TRA-8 resistance in that cell.

Also provided is a method of screening a cell for a biomarker of resistance to a death receptor agonist comprising monitoring the association of a caspase or modulator of caspases (eg, cIAP1, cIAP2, XIAP, survivin) with the CARD containing protein and comparing the level of association with a sample from known resistant and non-resistant control cells. The association of IAPs with the CARD containing protein at levels similar to that of resistant cells signifies resistance to the agonist. Optionally, the cell to be screened is pre-contacted with a death receptor agonist (e.g. agonistic antibody).

As an illustration, the present method can comprise treating a cell from a subject with TRA-8 antibody, isolating the protein from the cell lysate, immunoprecipitating DDX3 protein, separating DDX3 by SDS-polyacrylamide gel electrophoresis (SDS-PAGE) (reducing or non-reducing conditions), transferring the separated protein to a nitrocellulose membrane, and using standard Western techniques to detect caspases (e.g. caspase-1, caspase-2, caspase-4, caspase-5) and IAPs (e.g. cIAP1, cIAP2, XIAP, survivin) associated with DDX3, wherein the detection of IAPs with DDX3 is evidence of TRA-8 resistance in that cell. The level of association can be compared to a control level. The control level can be based on non-resistant cells. If the test level is higher than that of non-resistant control cells, then resistance is indicated. The control level can be based on resistant cells such that a similarity between the test levels and control levels indicates resistance.

Also provided is a method of screening for a modulator of a CARD containing protein. In particular, provided herein is such a screening method wherein the modulator reverses or prevents a target cell's resistance to a death receptor agonist. The steps of the screening method comprise contacting the CARD containing protein with a candidate agent and detecting a change (e.g. decrease) in one or more activities of the CARD containing protein in the presence of the candidate agent as compared to the absence of the candidate agent, wherein the activity or activities correlate with the target cell's resistance to the death receptor agonist. A decrease in the activity or activities of the CARD containing protein indicates the candidate agent modulates the CARD containing protein. This method could be modified to utilize a modified CARD containing protein, including for example, naturally occurring modifications or non-naturally occurring modifications. Such modifications can include truncations, mutations, chimeric proteins, etc. For example, the nucleic acid sequence for DDX3 is set forth in SEQ ID NO:25. Examples of DDX3 mutations include adenosine to guanosine substitutions at positions 1842 and 2493 in SEQ ID NO:25.

Any number of activities of the CARD containing protein can be assessed in the screening methods described herein. For example, the activity of the CARD containing protein can be phosphorylation, including for example, phosphorylation at or near the death receptor binding amino acids. Thus, the present method can comprise detecting phosphorylation of the CARD containing protein. Cell-based and cell-free assays for detecting phosphorylation of proteins are well known in the art and include the use of antibodies, including, for example, anti-Phosphoserine (Chemicon® AB1603) (Chemicon, Temecula, Calif.), anti-Phosphothreonine (Chemicon® AB1607), and anti-Phosphotyrosine (Chemicon® AB1599). Site-specific antibodies can also be generated specific for the phosphorylated form of DDX-3. The methods of generating and using said antibodies are well known in the art.

Another CARD containing protein activity that can be assessed in the screening methods described herein is binding activity. For example, the activity of the CARD containing protein can be binding to the death receptor. Thus, the present method can comprise detecting the interaction between the CARD containing protein and the death receptor. The activity of the CARD containing protein can be CARD-dependent binding. Thus, the present method can comprise detecting CARD-dependent binding to, for example, cIAP1, cIAP2, XIAP, or survivin. Methods for the detection of protein binding are well known in the art and include, for example, co-immunoprecipitation combined with enzyme linked immunosorbent assays (ELISAs) or Western blotting. In another example, a sandwich assay can be used wherein a first antibody captures the death receptor and wherein a second antibody detects the CARD containing protein. In another example, a sandwich assay can be used wherein a first antibody captures the CARD containing protein and wherein a second antibody detects the death receptor.

Further provided herein are the screening assays wherein the assessed activity of the CARD containing protein is cleavage, including for example, cleavage that occurs during death receptor-induced apoptosis. Thus, the screening method can comprise detecting cleavage of the CARD containing protein. Methods for the detection of protein cleavage are well known in the art and include, for example, Western blotting.

The contacting step of the screening method can be done either in vivo or in vitro. The screening method can be either cell-based or cell-free. Thus, in one aspect, the CARD containing protein is in a target cell. The CARD containing protein can be naturally occurring in the cell or the cell can be genetically engineered to produce the CARD containing protein. In a cell free method, the CARD containing protein can be modified to be attached to a substrate or to form a chimeric protein.

Optionally, the screening method can further comprise contacting the target cell, or a non-cellular system comprising a death receptor, one or more times with a death receptor agonist and detecting the level of resistance to the death receptor agonist. The level of resistance to the death receptor agonist can be detected, for example, by measuring apoptosis, a decline in apoptosis upon repeated exposure to the death receptor agonist indicating an increase in resistance. Methods for the detection of apoptosis are well known in the art and include, for example, reagents for detecting terminal dUTP nick-end labeling (TUNEL), active-caspase 3, cell surface phospholipid phosphatidylserine (PS) by Annexin V. Reagents for these and other methods for detecting apoptosis are commercially available.

In general, candidate agents can be identified from large libraries of natural products or synthetic (or semi-synthetic) extracts or chemical libraries according to methods known in the art. Those skilled in the field of drug discovery and development will understand that the precise source of test extracts or compounds is not critical to the screening procedure(s) of the invention. Accordingly, virtually any number of peptides, chemical extracts or compounds can be screened using the exemplary methods described herein. Examples of such peptides, extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, polypeptide- and nucleic acid-based compounds. Synthetic compound libraries are commercially available, e.g., from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods. In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their effect on an activity of the CARD containing protein should be employed whenever possible.

When a crude extract is found to have a desired activity, further fractionation of the positive lead extract is necessary to isolate chemical constituents responsible for the observed effect. Thus, the goal of the extraction, fractionation, and purification process is the careful characterization and identification of a chemical entity within the crude extract having an activity that stimulates or inhibits an activity of the CARD containing protein. The same assays described herein for the detection of activities in mixtures of compounds can be used to purify the active component and to test derivatives thereof. Methods of fractionation and purification of such heterogenous extracts are known in the art. If desired, compounds shown to be useful agents for treatment are chemically modified according to methods known in the art. Compounds identified as being of therapeutic value may be subsequently analyzed using animal models for diseases or conditions in which it is desirable to regulate or mimic an activity of the CARD containing protein.

Provided is a method of monitoring resistance to a death receptor agonist in a subject, comprising acquiring a biological sample from the subject and detecting association of a CARD containing protein with a death receptor in the sample, the association indicating resistance. As described above, the level of association can be compared to a control level.

As an illustration, the present method can comprise isolating from a subject a biological sample, wherein the subject has been treated with a therapeutic anti-DR5 antibody (e.g. TRA-8), isolating the protein from the biological sample, immunoprecipitating DR5 protein, separating DR5 by SDS-polyacrylamide gel electrophoresis (SDS-PAGE) (reducing or non-reducing conditions), transferring the separated protein to a nitrocellulose membrane, and using antibodies to DDX3 and standard Western blot techniques to detect DDX3 associated with DR5, wherein association is evidence of TRA-8 resistance in that cell.

Provided is a method of monitoring resistance to a death receptor agonist in a subject, comprising acquiring a biological sample from the subject and detecting association of a caspase or modulator of caspase with a CARD containing protein in the sample, the association indicating resistance.

As an illustration, the present method can comprise isolating from a subject a biological sample being treated with a therapeutic anti-DR5 antibody (e.g. TRA-8), isolating the protein from the biological sample, immunoprecipitating DDX-3 protein, separating DDX-3 by SDS-polyacrylamide gel electrophoresis (SDS-PAGE) (reducing or non-reducing conditions), transferring the separated protein to a nitrocellulose membrane, and using standard Western techniques to detect caspases (e.g., caspase-1, caspase-2, caspase-4, caspase-5) and IAPs (e.g., cIAP1, cIAP2, XIAP, survivin) associated with DDX3, wherein the detection of cIAP1 with DDX3, for example, is evidence of TRA-8 resistance in that cell.

Provided is a method of monitoring resistance to a death receptor agonist in a subject, comprising acquiring a biological sample from the subject and detecting phosphorylation of DDX3. Methods for detecting phosphorylation of proteins are well known in the art and include the use of antibodies, including, for example, anti-Phosphoserine (Chemicon® AB1603), anti-Phosphothreonine (Chemicon® AB1607), and anti-Phosphotyrosine (Chemicon® AB1599).

Site-specific antibodies can also be generated specific for the phosphorylated form of DDX-3. The methods of generating and using said antibodies are well known in the art.

Provided is a method of selectively inducing apoptosis in a target cell expressing a death receptor, comprising the steps of contacting the target cell with a therapeutic amount of a death receptor agonist that specifically binds the death receptor and administering to the target cell a therapeutic amount of a modulator of one or more activities of a CARD containing protein.

The ability of an agonist and CARD containing protein modulator to induce apoptosis can be confirmed by culturing cells such as the human leukemia cell line Jurkat (American Type Culture No. TIB-152) and astrocytoma cell line 1321N1 in medium in which the test sample has been added. The survival rate can be determined by, for example, using an ATPLITE assay.

The methods and compositions provided herein can be used in the treatment of diseases associated with inappropriate survival or proliferation of cells, including those attributable to dysregulation of the apoptosis systems in cancer or in inflammatory and autoimmune diseases. Inflammatory and autoimmune diseases illustratively include systemic lupus erythematosus, Hashimoto's disease, rheumatoid arthritis, graft-versus-host disease, Sjögren's syndrome, pernicious anemia, Addison disease, scleroderma, Goodpasture's syndrome, Crohn's disease, autoimmune hemolytic anemia, sterility, myasthenia gravis, multiple sclerosis, Basedow's disease, thrombopenia purpura, insulin-dependent diabetes mellitus, allergy, asthma, atopic disease, arteriosclerosis, myocarditis, cardiomyopathy, glomerular nephritis, hypoplastic anemia, rejection after organ transplantation. Cancers include numerous malignancies of lung, prostate, liver, ovary, colon, cervix, lymphatic and breast tissues. Thus, the provided compositions and methods can further be used to target and selectively induce apoptosis in activated immune cells including activated lymphocytes, lymphoid cells, myeloid cells, and rheumatoid synovial cells (including inflammatory synoviocytes, macrophage-like synoviocytes, fibroblast-like synoviocytes) and in virally infected cells (including those infected with HIV, for example) so long as those targeted cells express or can be made to express the specific death receptors (i.e., DR4 or DR5).

Provided is a method of treating a subject with cancer or with an autoimmune or inflammatory disease, comprising administering to the subject a therapeutic amount of a death receptor agonist and a modulator of one or more activities of a CARD containing protein, wherein the modulator reduces resistance to the death receptor agonist.

As used throughout, a "therapeutic amount" of a death receptor agonist and/or modulator of CARD containing protein is the quantity sufficient to cause apoptosis in the target cell. As used herein, the terms "therapeutic amount" and "pharmaceutically effective amount" are synonymous. One of skill in the art could readily determine the proper therapeutic amount.

In the treatment of disease, e.g., cancer, autoimmune and inflammatory diseases, combinations of treatment can also be used. For example, the agonists and modulators of CARD containing protein of the provided methods and compositions can be administered in conjunction with other therapeutic agents. As used herein a "therapeutic agent" is a compound or composition effective in ameliorating a pathological condition. Radiotherapy can also be combined with or without other therapeutic agents. One skilled in the art would adapt the form of radiotherapy to the disease.

Examples of therapeutic agents include chemotherapeutic agents, anti-inflammatory agents, Disease Modifying Anti Rheumatic Drug (DMARDs), antibodies, members of TNF family, antiviral agents, anti-opportunistic agents, antibiotics, immunosuppresives, immunoglobulins, anti-malarial agents, anti-rheumatoid arthritis agents, cytokines, chemokines, growth factors, and anti-cancer compounds. An anti-cancer compound is a compound or composition effective in inhibiting or arresting the growth of an abnormally growing cell. Illustrative examples of anti-cancer compounds include: bleomycin, carboplatin, chlorambucil, cisplatin, colchicine, cyclophosphamide, daunorubicin, dactinomycin, diethylstilbestrol doxorubicin, etoposide, 5-fluorouracil, floxuridine, melphalan, methotrexate, mitomycin, 6-mercaptopurine, teniposide, 6-thioguanine, vincristine and vinblastine. Further examples of anti-cancer compounds and therapeutic agents are found in The Merck Manual of Diagnosis and Therapy, 15th Ed., Berkow et al., eds., 1987, Rahway, N. J. and Sladek et al. Metabolism and Action of Anti-Cancer Drugs, 1987, Powis et al. eds., Taylor and Francis, New York, N.Y.

The PKC inhibitor, bisindolymaleimide VIII (BisVIII), greatly facilitates Fas-mediated apoptosis (Zhou, T., et al. 1999. Nat Med 5:42-48). It has been shown that that synergistic activation of the JNK/p38 pathway plays an important role (Ohtsuka, T., and T. Zhou. 2002. J Biol Chem 277:29294-29303), and that the enhancement of DR5-mediated apoptosis by three common chemotherapeutic agents appears to occur through a similar mechanism (Ohtsuka, T., D. et al. 2003. Oncogene 22:2034-2044). Thus, the provided methods can further comprise the use of apoptosis-inducing compounds, such as bisindolylmaleimide VIII (BisVIII) or other sensitizing agents like SN-50 or LY294002. Thus, the agonists and modulators of CARD containing protein of the provided methods and compositions can be combined with BisVIII. The agonists and modulators of CARD containing protein of the provided methods and compositions can further be combined with a non-steroidal anti-inflammatory drug (NSAID) (e.g., sulindac sulfide or other COX-1 or COX-2 inhibitors).

Therapy using the agonists of the provided methods and compositions can also be combined with therapy using other agonists. For example, an antibody to DR5 can be administered to a subject in need thereof along with, prior to, or following administration of an antibody to DR4. Such combined antibody therapy can be further combined with administration of one or more of the modulators of CARD containing protein provided herein and can be further combined with other therapeutic agents.

Provided is a composition comprising a death receptor agonist and an agent that modulates one or more activities of a CARD containing protein, wherein the modulator reduces resistance to the death receptor agonist. The provided composition can further comprise a therapeutic agent selected from the group consisting of a chemotherapeutic agent, member of TNF family, antiviral agent, anti-inflammatory agent, anti-opportunistic agent, antibiotic, immunosuppresant, immunoglobulin, anti-malarial agent, anti-rheumatoid arthritis agent, cytokine, chemokine, and growth factor.

The term "protein," "peptide," "polypeptide," or "peptide portion" are used interchangeably herein and are used broadly herein to mean two or more amino acids linked by a peptide bond. The term "fragment" is used herein to refer to a portion of a full-length polypeptide or protein, such portion which can be produced by a proteolytic reaction on a polypeptide, i.e., a peptide produced upon cleavage of a peptide bond in the polypeptide. It should be recognized that the fragment need not necessarily be produced by a proteolytic reaction but can be produced using methods of chemical synthesis or methods of recombinant DNA technology, to produce a synthetic polypeptide. It should be recognized that the term "protein" and "polypeptide" are not used herein to suggest a particular size or number of amino acids comprising the molecule and that a peptide of the invention can contain up to several amino acid residues or more.

By "isolated" or "purified" is meant a composition (e.g., a polypeptide or nucleic acid) that is substantially free from other materials, including materials with which the composition is normally associated in nature. The polypeptides of the invention, or fragments thereof, can be obtained, for example, by extraction from a natural source (e.g., phage), by expression of a recombinant nucleic acid encoding the polypeptide (e.g., in a cell or in a cell-free translation system), or by chemically synthesizing the polypeptide. In addition, polypeptide fragments may be obtained by any of these methods, or by cleaving full length polypeptides. A fragment of a reference protein or polypeptide includes only contiguous amino acids of the reference protein/polypeptide, and is at least one amino acid shorter than the reference sequence.

When specific proteins are referred to herein, variants, derivatives, and fragments are contemplated. Protein variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. Typically, no more than about from 2 to 6 residues are deleted at any one site within the protein molecule but deletion can range from 1-30 residues. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known and include, for example, M13 primer mutagenesis and PCR mutagenesis Amino acid substitutions are typically of single residues, but can occur at a number of different locations at once; insertions usually will be on the order of about from 1 to 10 amino acid residues. Deletions or insertions preferably are made in adjacent pairs, i.e., a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure unless such a change in secondary structure of the mRNA is desired. Substitutional variants are those in which at least one residue has been removed and a different residue inserted in its place. Such substitutions generally are made in accordance with the following Tables 1 are referred to as conservative substitutions.

TABLE 1

| Amino Acid Substitutions | |
|---|---|
| Original Residue | Exemplary Substitutions |
| Ala | Ser |
| Arg | Lys |
| Asn | Gln |
| Asp | Glu |
| Cys | Ser |
| Gln | Asn |
| Glu | Asp |
| Gly | Pro |
| His | Gln |
| Ile | Leu; Val |
| Leu | Ile; Val |
| Lys | Arg; Gln |
| Met | Leu; Ile |
| Phe | Met; Leu; Tyr |
| Pro | Gly |
| Ser | Thr |
| Thr | Ser |
| Trp | Tyr |
| Tyr | Trp; Phe |
| Val | Ile; Leu |

Substantial changes in function or immunological identity are made by selecting substitutions that are less conservative than those in Table 1, i.e., selecting residues that differ more significantly in their effect on maintaining (a) the structure of the polypeptide backbone in the area of the substitution, for example, as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, and (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations shown in Table 1. Conservatively substituted variations of each explicitly disclosed sequence are included within the polypeptides provided herein.

Typically, conservative substitutions have little to no impact on the biological activity of a resulting polypeptide. In a particular example, a conservative substitution is an amino acid substitution in a peptide that does not substantially affect the biological function of the peptide. A peptide can include one or more amino acid substitutions, for example 2-10 conservative substitutions, 2-5 conservative substitutions, 4-9 conservative substitutions, such as 2, 5 or 10 conservative substitutions.

A polypeptide can be produced to contain one or more conservative substitutions by manipulating the nucleotide sequence that encodes that polypeptide using, for example, standard procedures such as site-directed mutagenesis or PCR. Alternatively, a polypeptide can be produced to contain one or more conservative substitutions by using standard peptide synthesis methods. An alanine scan can be used to identify which amino acid residues in a protein can tolerate an amino acid substitution. In one example, the biological activity of the protein is not decreased by more than 25%, for example not more than 20%, for example not more than 10%, when an alanine, or other conservative amino acid (such as those listed below), is substituted for one or more native amino acids.

Further information about conservative substitutions can be found in, among other locations, in Ben-Bassat et al., (J. Bacteriol. 169:751-7, 1987), O'Regan et al., (Gene 77:237-51, 1989), Sahin-Toth et al., (Protein Sci. 3:240-7, 1994), Hochuli et al., (Bio/Technology 6:1321-5, 1988) and in standard textbooks of genetics and molecular biology.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

It is understood that there are numerous amino acid and peptide analogs which can be incorporated into the disclosed compositions. For example, there are numerous D amino acids or amino acids which have a different functional substituent than the amino acids shown in Table 1. The opposite stereoisomers of naturally occurring peptides are disclosed, as well as the stereoisomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson et al., Methods in Molec. Biol. 77:43-73 (1991), Zoller, Current Opinion in Biotechnology, 3:348-354 (1992); Ibba, Biotechnology & Genetic Enginerring Reviews 13:197-216 (1995), Cahill et al., TIBS, 14(10):400-403 (1989); Benner, TIB Tech, 12:158-163 (1994); Ibba and Hennecke, Bio/technology, 12:678-682 (1994), all of which are herein incorporated by reference at least for material related to amino acid analogs).

Molecules can be produced that resemble polypeptides, but which are not connected via a natural peptide linkage. For example, linkages for amino acids or amino acid analogs can include $CH_2NH$—, —$CH_2S$—, —$CH_2$—$CH_2$— CH═CH—(cis and trans), —$COCH_2$—CH(OH)$CH_2$—, and —$CHH_2SO$— (These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., Int J Pept Prot Res 14:177-185 (1979) (—$CH_2NH$—, $CH_2CH_2$—); Spatola et al. Life Sci 38:1243-1249 (1986) (—CH $H_2$—S); Hann J. Chem. Soc Perkin Trans. I 307-314 (1982) (—CH—CH—, cis and trans); Almquist et al. J. Med. Chem. 23:1392-1398 (1980) (—$COCH_2$—); Jennings-White et al. Tetrahedron Lett 23:2533 (1982) (—$COCH_2$—); Szelke et al. European Appin, EP 45665 CA (1982): 97:39405 (1982) (—CH(OH) $CH_2$—); Holladay et al. Tetrahedron. Lett 24:4401-4404 (1983) (—C(OH)$CH_2$—); and Hruby Life Sci 31:189-199 (1982) (—$CH_2$—S—); each of which is incorporated herein by reference. A particularly preferred non-peptide linkage is —$CH_2NH$—. It is understood that peptide analogs can have more than one atom between the bond atoms, such as b-alanine, g-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch *Ann. Rev. Biochem.* 61:387 (1992), incorporated herein by reference).

It is understood that one way to define any variants, modifications, or derivatives of the disclosed genes and proteins herein is through defining the variants, modification, and derivatives in terms of homology to specific known sequences. Specifically disclosed are variants of the nucleic acids and polypeptides herein disclosed which have at 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent homology to the stated or known sequence. Those of skill in the art readily understand how to determine the homology of two proteins or nucleic acids. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection. These references are incorporated herein by reference in their entirety for the methods of calculating homology.

The same types of homology can be obtained for nucleic acids by, for example, the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment.

The provided compositions may be administered orally, rectally, intracisternally, intraventricular, intracranial, intrathecal, intra-articularly, intravaginally, parenterally (intravenously, intramuscularly, or subcutaneously), locally (powders, ointments, or drops), by intraperitoneal injection, transdermally, by inhalation or as a buccal or nasal spray. The exact amount of the antibody or therapeutic agent required will vary from subject to subject, depending on the age, weight and general condition of the subject, the severity of the disease that is being treated, the location and size of the tumor, the particular compounds used, the mode of administration, and the like. An appropriate amount may be determined by one of ordinary skill in the art using only routine experimentation given the teachings herein. Typical single dosages of antibody range from 0.1-10,000 micrograms, preferably between 1 and 100 micrograms. Typical antibody concentrations in a carrier range from 0.2 to 2000 nanograms per delivered milliliter. For injection into a joint, volumes of antibody and carrier will vary depending upon the joint, but approximately 0.5-10 ml, and preferably 1-5 ml, is injected into a human knee and approximately 0.1-5 ml, and preferably 1-2 ml into the human ankle.

The composition can further comprise a pharmaceutically acceptable carrier. By "pharmaceutically acceptable" is meant a material that is not biologically or otherwise undesirable, which can be administered to an individual along with the selected substrate without causing significant undesirable biological effects or interacting in a deleterious manner with any of the other components of the pharmaceutical composition in which it is contained.

Depending on the intended mode of administration, the antibody or therapeutic agent can be in pharmaceutical compositions in the form of solid, semi-solid or liquid dosage forms, such as, for example, tablets, suppositories, pills, capsules, powders, liquids, or suspensions, preferably in unit dosage form suitable for single administration of a precise dosage. The compositions will include an effective amount of the selected substrate in combination with a pharmaceutically acceptable carrier and, in addition, may include other medicinal agents, pharmaceutical agents, carriers, or diluents. Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, ointments, powders, and solutions are also contemplated as being within the scope of this invention.

The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate and laurylsulphonate salts, and the like. These may include cations based on the alkali and alkaline earth metals, such as sodium, lithium, potassium, calcium, magnesium, and the like, as well as non-toxic ammonium, quaternary ammonium and amine cations including, but not limited to ammonium, tetramethylammonium, tetraethylammonium, methylamine, dimethylamine, trimethylamine, triethylamine, ethylamine, and the like. (See, for example, S. M. Barge et al., "Pharmaceutical Salts," J. Pharm. Sci., 1977, 66:1-19 which is incorporated herein by reference).

Provided is an isolated nucleic acid comprising double-stranded RNA (dsRNA) for use in RNA interference (RNAi). The dsRNA can be short interfering RNA (siRNA) or short hairpin RNA (shRNA). Thus, provided is an isolated nucleic acid comprising an shRNA, wherein the shRNA inhibits the expression of a CARD containing protein. The shRNA can be encoded by the nucleic acid sequence SEQ ID NO:10, 12, 14, or 16.

The disclosed nucleic acids are made up of for example, nucleotides, nucleotide analogs, or nucleotide substitutes. Non-limiting examples of these and other molecules are discussed herein. It is understood that for example, when a vector is expressed in a cell, the expressed mRNA will typically be made up of A, C, G, and U. Likewise, it is understood that if, for example, an antisense molecule is introduced into a cell or cell environment through for example exogenous delivery, it is advantageous that the antisense molecule be made up of nucleotide analogs that reduce the degradation of the antisense molecule in the cellular environment.

By "isolated nucleic acid" or "purified nucleic acid" is meant DNA that is free of the genes that, in the naturally-occurring genome of the organism from which the DNA of the invention is derived, flank the gene. The term therefore includes, for example, a recombinant DNA which is incorporated into a vector, such as an autonomously replicating plasmid or virus; or incorporated into the genomic DNA of a prokaryote or eukaryote (e.g., a transgene); or which exists as a separate molecule (e.g., a cDNA or a genomic or cDNA fragment produced by PCR, restriction endonuclease digestion, or chemical or in vitro synthesis). It also includes a recombinant DNA which is part of a hybrid gene encoding additional polypeptide sequence. The term "isolated nucleic acid" also refers to RNA, e.g., an mRNA molecule that is encoded by an isolated DNA molecule, or that is chemically synthesized, or that is separated or substantially free from at least some cellular components, e.g., other types of RNA molecules or polypeptide molecules.

Provided herein is a vector comprising any of the nucleic acids provided herein, operably linked to an expression control sequence. Preferred promoters controlling transcription from vectors in mammalian host cells may be obtained from various sources, for example, the genomes of viruses such as: polyoma, Simian Virus 40 (SV40), adenovirus, retroviruses, hepatitis B virus and most preferably cytomegalovirus, or from heterologous mammalian promoters, e.g. beta actin promoter or EF1 promoter, or from hybrid or chimeric promoters (e.g., cytomegalovirus promoter fused to the beta actin promoter). The early and late promoters of the SV40 virus are conveniently obtained as an SV40 restriction fragment which also contains the SV40 viral origin of replication (Fiers et al., Nature, 273: 113 (1978)). The immediate early promoter of the human cytomegalovirus is conveniently obtained as a HindIII E restriction fragment (Greenway, P. J. et al., Gene 18: 355 360 (1982)). Of course, promoters from the host cell or related species also are useful herein.

"Enhancer" generally refers to a sequence of DNA that functions at no fixed distance from the transcription start site and can be either 5' (Laimins, L. et al., Proc. Natl. Acad. Sci. 78: 993 (1981)) or 3' (Lusky, M. L., et al., Mol. Cell. Bio. 3: 1108 (1983)) to the transcription unit. Furthermore, enhancers can be within an intron (Banerji, J. L. et al., Cell 33: 729 (1983)) as well as within the coding sequence itself (Osborne, T. F., et al., Mol. Cell. Bio. 4: 1293 (1984)). They are usually between 10 and 300 bp in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, fetoprotein and insulin), typically one will use an enhancer from a eukaryotic cell virus for general expression. Preferred examples are the SV40 enhancer on the late side of the replication origin (bp 100 270), the cytomegalovirus early promoter enhancer, the polyoma enhancer on the late side of the replication origin, and adenovirus enhancers.

The promoter and/or enhancer may be specifically activated either by light or specific chemical events which trigger their function. Systems can be regulated by reagents such as tetracycline and dexamethasone, synthetic transcription factors, directed RNA self-cleavage (Yen L. et al. 2004. Nature 431:471-476), and other approaches. There are also ways to enhance viral vector gene expression by exposure to irradiation, such as gamma irradiation, or alkylating chemotherapy drugs.

The promoter and/or enhancer region can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (plus a linked intron sequence), beta-actin, elongation factor-1 (EF-1) and retroviral vector LTR.

It has been shown that all specific regulatory elements can be cloned and used to construct expression vectors that are selectively expressed in specific cell types such as melanoma cells. The glial fibrillary acetic protein (GFAP) promoter has been used to selectively express genes in cells of glial (astrocytic) origin. The HLA-DR, CD11c, Fascin and CD68 promoters have all been used to selectively express genes in antigen-presenting cells, including macrophages and dendritic cells (Brocker, T., et al. 1997. J Exp Med 185:541-550; Gough P. J. and Raines, E. W. 2003. Blood 101:485-491; Cui, Y. et al. 2002. Blood 99:399-408; Sudowe, S. et al. 2003. Mol Ther 8:567-575), and promoter elements from dendritic cell-specific genes (such as CD83) may also prove useful in this regard (Berchtold S. et al. 2002. Immunobiology 205:231-246).

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contains a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases. It is also preferred that the transcribed units contain other standard sequences alone or in combination with the above sequences improve expression from, or stability of, the construct.

The viral vectors can include nucleic acid sequence encoding a marker product. This marker product is used to determine if the gene has been delivered to the cell and once delivered is being expressed. Preferred marker genes include the *E. coli* lacZ gene, which encodes β galactosidase, green fluorescent protein (GFP), and luciferase.

In some embodiments the marker may be a selectable marker. Examples of suitable selectable markers for mammalian cells are dihydrofolate reductase (DHFR), thymidine kinase, neomycin, neomycin analog G418, hygromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR cells and mouse LTK cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern P. and Berg, P., J. Molec. Appl. Genet. 1: 327 (1982)), mycophenolic acid, (Mulligan, R. C. and Berg, P. Science 209: 1422 (1980)) or hygromycin, (Sugden, B. et al., Mol. Cell. Biol. 5: 410 413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puromycin.

Provided is a cell comprising any of the herein provided vectors. The disclosed cell can be any cell used to clone or propagate the vectors provided herein. Thus, the cell can be from any primary cell culture or established cell line. The cell type can be selected by one skilled in the art based on the choice of vector and desired use.

Provided is an isolated polypeptide comprising the CARD containing protein binding region of a death receptor, wherein the polypeptide comprises fewer than 25 amino acid residues.

Thus, the provided polypeptide can be the CARD containing protein binding region of TFNR1 (accession no. gi:23312372). The provided polypeptide can be the CARD containing protein binding region of Fas Receptor (accession no. gi:119833). The provided polypeptide can be the CARD containing protein binding region of a TRAIL receptor. Thus, the provided polypeptide can be the CARD containing protein binding region of DR4 (accession no. gi:21264525). The provided polypeptide can be the CARD containing protein binding region of DR5 (accession no. gi:3721878). The provided polypeptide can be a fragment of the amino acid sequence SEQ ID NO:22, wherein the fragment binds a CARD containing protein disclosed herein. As an illustrative example, the provided polypeptide can comprise amino acids 250-340 of DR5. Thus, the polypeptide can comprise the amino acid sequence SEQ ID NO:23. The polypeptide can further comprise a fragment of amino acid sequence SEQ ID NO:23, such that the fragment is capable of binding DDX3. As an example, the modulator can be a polypeptide comprising amino acids 280-310 of DR5. Thus, the modulator can comprise the amino acid sequence SEQ ID NO:24. As another example, the modulator can be a polypeptide comprising amino acids 300-330 of DR5. Thus, the modulator can comprise the amino acid sequence SEQ ID NO:36.

By "binds" is meant that the polypeptide forms non-covalent bonds (e.g. hydrogen bonds) with a CARD containing protein protein with sufficient affinity that can be detected with standard biochemical methods. In one aspect, the provided polypeptide binds a CARD containing protein with an affinity equal to or greater than the death receptor from which it is derived.

The CARD containing protein binding region of the death receptor has utility as a soluble receptor for competitive inhibition of CARD containing protein binding. Thus, provided is a method of blocking CARD containing protein binding to a death receptor in a cell, comprising contacting the cell with a polypeptide encoding the survival region of a death receptor, as disclosed herein, or a fragment thereof that blocks the binding. Also provided is a method of reversing a cell's resistance to a death receptor agonist in a cell comprising contacting the cell with the polypeptide.

Provided is an isolated polypeptide comprising the death receptor binding domain of a CARD containing protein. The provided polypeptide can be the death receptor binding domain of DDX3 (SEQ ID NO:25, accession no. gi:13514816). The provided polypeptide can be a fragment of the amino acid sequence SEQ ID NO:25, wherein the fragment binds a death receptor disclosed herein. DDX3 binds DR5 at approximately amino acids 200 to 250 and 350 to 400. Thus, the modulator can be a polypeptide comprising amino acids 200 to 250 of DDX3, or fragments thereof. Thus, the modulator can comprise the amino acid sequence SEQ ID NO:37. Thus, the modulator can be a polypeptide comprising amino acids 350 to 400 of DDX3, or fragments thereof. Thus, the modulator can comprise the amino acid sequence SEQ ID NO:38. The provided polypeptide can be the death receptor binding domain of mda-5 (accession no. gi:11344593). The provided polypeptide can be the death receptor binding domain of RIG-1 (accession no. gi:6048564).

An isolated polypeptide comprising the death receptor binding domain of a CARD containing protein has utility as a dominant negative inhibitor of death receptor binding by CARD containing proteins if the polypeptide is unable to inhibit death receptor-induced apoptosis. Thus, in one aspect, the isolated polypeptide can not bind caspases or IAPs. The CARD motif responsible for binding IAPs of DDX3 is at approximately amino acids 50-100. Thus, the provided polypeptide can comprise the death receptor binding domain of DDX3 but not comprise amino acids 50-100 of DDX3. Thus, the modulator can be a polypeptide comprising amino acids 200 to 250 and/or amino acids 350 to 400 of DDX3, but not comprising amino acids 50-100 of DDX3. For example, provided is a polypeptide consisting of amino acids 151-662 of DDX3. Thus, the modulator can comprise a polypeptide consisting of the amino acid sequence SEQ ID NO:39.

In a further aspect, the polypeptide can block the association of endogenous CARD containing proteins with the death receptor. In a further aspect, the polypeptide can prevent the recruitment of IAPs to the death receptor. In another aspect, the polypeptide can not inhibit the recruitment of FADD to death receptor. Any combination of these aspects is contemplated.

The ability of CARD containing proteins such as DDX3 to inhibit death receptor-induced apoptosis is, at least in part, due to the recruitment of IAPs to the death receptor by the CARD domain of the CARD containing protein. Thus, provided is a method of blocking the association of IAPs with a death receptor, comprising contacting the cell with the disclosed polypeptide. Also provided is a method of reversing a cell's resistance to a death receptor agonist comprising contacting the cell with the disclosed polypeptide.

The compositions disclosed herein and the compositions necessary to perform the disclosed methods can be made using any method known to those of skill in the art for that particular reagent or compound unless otherwise specifically noted.

For example, the nucleic acids can be made using standard chemical synthesis methods or can be produced using enzymatic methods or any other known method. Such methods can range from standard enzymatic digestion followed by nucleotide fragment isolation (see for example, Sambrook et al., Molecular Cloning: A Laboratory Manual, 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., Ann. Rev. Biochem. 53:323-356 (1984), (phosphotriester and phosphite-triester methods), and Narang et al., Methods Enzymol., 65:610-620 (1980), (phosphotriester method). Protein nucleic acid molecules can be made using known methods such as those described by Nielsen et al., Bioconjug. Chem. 5:3-7 (1994).

One method of producing the disclosed polypeptides is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof (Grant G A (1992) Synthetic Peptides: A User Guide. W.H. Freeman and Co., N.Y. (1992); Bodansky M and Trost B., Ed. (1993) Principles of Peptide Synthesis. Springer-Verlag Inc., NY, which is herein incorporated by reference at least for material related to peptide synthesis). Alternatively, the peptide or polypeptide is independently synthesized in vivo as described herein. Once isolated, these independent peptides or polypeptides may be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) FEBS Lett. 307:97-101; Clark-Lewis I et al., J. Biol. Chem., 269:16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

The following examples are set forth below to illustrate the methods and results according to the present invention. These examples are not intended to be inclusive of all aspects of the present invention, but rather to illustrate representative methods and results. These examples are not intended to exclude equivalents and variations of the present invention which are apparent to one skilled in the art.

EXAMPLES

Example 1

Inducible Resistance of Tumor Cells to TRAIL-R2-Mediated Apoptosis by Generation of a Blockade at the Death Domain Function Materials and Methods Cell Lines, Antibodies, and Reagents:

Human breast cancer cell line, MDA-MB-231, was purchased from the American Tissue Culture Collection (ATCC) (Manassas, Va.). Human ovarian cancer cell line, UL-3C, was obtained. Cells were maintained in DMEM or RPMI1640 supplemented with 10% heat-inactivated FCS, 50 μg/ml streptomycin, and 50 U/mL penicillin (Cellgro, Mediatec, Inc., Herndon, Va.). Anti-human TRAIL-R1 (clone: 2E12) and anti-human TRAIL-R2 (clone: TRA-8) monoclonal antibodies were previously described (Ichikawa, et al. 2003; Ichikawa, et al. 2001). Anti-human TRAIL-R2 (clone: 2B4) for flow cytometry and immunoprecipitation assays was developed. Recombinant soluble TRAIL was purchased from Alexis Biochemicals (San Diego, Calif.). Polyclonal anti-caspase 3 and anti-caspase 8 antibodies were purchased from BD PharMingen (San Diego, Calif.). Monoclonal anti-human caspase 2, 3, 8, 9 and 10 antibodies, and monoclonal anti-human Bcl-2, Bcl-xL, Bax, cIAP-1, cIAP-2, XIAP and survivin antibodies were prepared. Polyclonal anti-phospho-SAPK/JNK ($Thr^{183}$/$Tyr^{185}$), anti-phospho-p38 MAPK ($Thr^{180}$/$Tyr^{182}$), anti-PARP antibodies were purchased from Cell Signaling Technology, Inc. (Beverly, Mass.). Anti-β-actin antibody was purchased from Sigma (St. Louis, Mo.). Anti-FADD was purchased from Transduction Laboratories (Lexington, Ky.). Anti-FLIP was purchased from ProSci Inc. (Poway, Calif.). All horseradish peroxidase (HRP)-conjugated secondary reagents were purchased from Southern Biotechnology Associates, Inc. (Birmingham, Ala.).

Flow Cytometry Analysis of Cell Surface Expression of TRAIL-R1 and -R2:

$10^6$ cells were incubated with 1 μg/ml biotinylated 2E12 and 1 μg/ml PE-conjugated 2B4 on ice for 30 minutes. After twice wash with FACS buffer (PBS with 5% FBS and 0.01% $NaN_3$), cells were incubated with Streptoavidin-Cychrome. 10,000 viable cells were analyzed by FACScan flow cytometer (BD, CA).

Cytotoxicity Analysis of Tumor Cell Susceptibility to TRA-8, 2E12 and TRAIL-Mediated Apoptosis:

Cells (1,000 cells per well) were seeded into 96-well plate in triplicate with eight concentrations (double serial dilutions from 1000 ng/ml) of TRA-8, 2E12, or TRAIL. Cell viability was determined after overnight culture using ATPLITE assay according to the manufacture's instructions (Packard Instruments, Meriden, Conn.). The results are presented as the precentage of viable cells in treated wells compared to medium control wells.

Induction of Tumor Cell Resistance to TRAIL-R2:

Cells ($5\times10^5$/ml) were incubated with a starting dose of 1 ng/ml TRA-8 for two days. Cells were split with fresh medium and incubated with a double dose of TRA-8 every two days until TRA-8 dose reached 2,000 ng/ml. At each treatment cycle, the cell viability of non-induced (parental) and induced cells treated with an inducing dose of TRA-8 was determined by ATPLITE assay.

Cloning and Sequencing of TRAIL-R2:

The full-length cDNA of TRAIL-R2 were obtained by polymerase chain reaction (PCR) using the platinum DNA proofreading polymerase (Invitrogen). The cDNAs were cloned into pCR2.1-TOPO vector (Invitrogen). At least five independent clones were selected for sequencing.

Western Blot Analysis of Apoptosis-Associated Proteins:

Tumor cells ($3\times10^6$) were washed twice with cold PBS and lysed with 300 μl lysis buffer containing 10 mM Tris-HCl (pH 7.6), 150 mM NaCl, 0.5 mM EDTA, 1 mM EGTA, 0.1% SDS, 1 mM sodium orthovanadate, and a mixture of protease inhibitors (1 mM phenylmethylsulfonyl fluoride, 1 μg/ml pepstatin A, 2 μg/ml aprotinin). Lysates were sonicated for 10 seconds, and centrifuged for 20 minutes at 12,000 g. The cell lysates with equal amount of total proteins were boiled for 5 minutes with SDS-PAGE sample buffer. Total cell lysates were separated in 8%, 10%, or 12% SDS-PAGE, and electrophoretically transferred to nitrocellulose membrane. The blots were blocked with 5% nonfat dry milk in TBST buffer (20 mM Tris-HCl (pH 7.4), 500 mM NaCl, and 0.1% Tween 20) and incubated with primary antibody in blocking buffer at 4° C. overnight. The blots were washed three times with TBST and probed with HRP-conjugated secondary antibodies for one hour at room temperature. After washing four times with TBST, the probed proteins were visualized using the ECL Western blotting detection system (Amersham Biosciences, Piscataway, N.J.) according to the manufacturer's instructions.

cDNA Array Analysis of Transcriptional Regulation of Apoptosis- and Cell Signaling-Associated Genes:

The Human Apoptosis Gene Array (HS-002) and the Human Signal Transduction PathwayFinder Gene Array (HS-008) were purchased from SuperArray, Inc (Frederick, Md.). Total RNA was extracted from cells using the TRIZOL® protocol (Invitrogen, Carlsbad, Calif.). The cDNA probes were synthesized with $^{32}P$-dCTP. The cDNAs on the membrane blots were hybridized with the $^{32}P$-dCTP labeled probes at 60° C. overnight. The gene expression profiles were analyzed using the CYCLONE PHOSPHORIMAGER™ (Packard Instruments, Meridien, Conn.).

Co-Immunoprecipitation of TRAIL-R1 and TRAIL-R2:

$10^7$ cells were washed with ice-cold PBS, and lysed for 15 min on ice with lysis buffer (1% Triton X-100, 150 mM NaCl, 10% glycerol, 20 mM Tris-HCl [pH 7.5], 2 mM EDTA, 0.57 mM PMSF, and a protease inhibitor cocktail). The lysates were then cleared twice by centrifugation at 16,000 g for 10 minutes at 4° C. The soluble fraction was incubated with 30 μl TRA-8 or 2B4 conjugated Sepharose 4B at 4° C. overnight. After seven washes with lysis buffer and three washes with 10 mM Tris, the bound proteins were eluted by boiling for 3 minutes in SDS-PAGE loading buffer and separated in SDS-PAGE. The presence of caspase 8 and FADD was determined by Western blot analysis.

Two-Dimensional Polyacrylamide Gel Electrophoresis:

After co-immunoprecipitation with 2B4-Sepharose 4B, the proteins were eluted and desalted with acetone, and reconstituted in the IEF sample buffer (Bio-Rad, Hercules, Calif.). 160 μg total proteins were loaded in the IPG strip (Bio-Rad) at room temperature overnight, and then separated in the PROTEAN IEF™ Cell (BioRad). The protein strips were equilibrated with the ReadyPrep Equilibration Buffers (Bio-Rad), and further separated in 10% SDS-PAGE gel. Upon completion, the gels were fixed with a buffer containing 10% methanol and 7% acetic acid, and stained with SYPRO™ Ruby Staining buffer (Bio-Rad). The gels were imaged using the VERSADOC™ Digital Imaging System (Bio-Rad) and analyzed with the PDQUEST™ software (Bio-Rad).

Results

Induction of Selective Resistance to TRAIL-R2-Mediated Apoptosis.

Figure 1A:
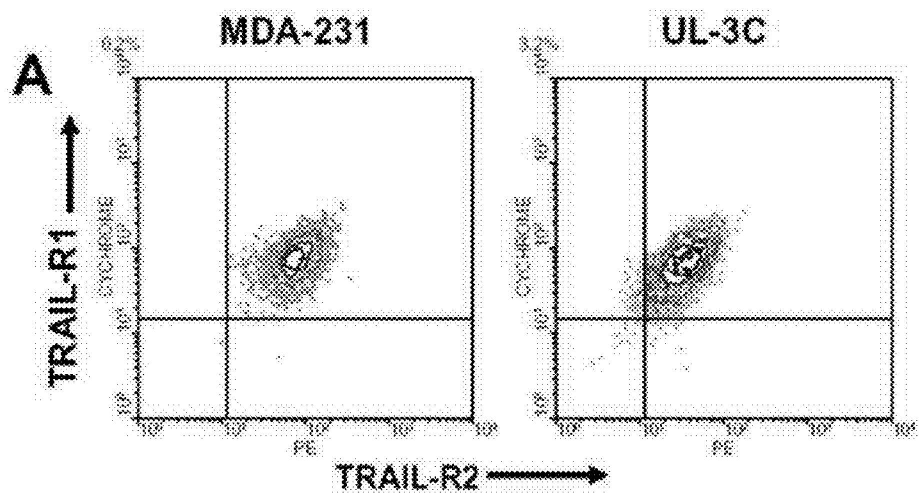
FIGS. 1A, 1B and 1C show induction of tumor cell resistance to TRA-8-mediated apoptosis.
Figure 1B:
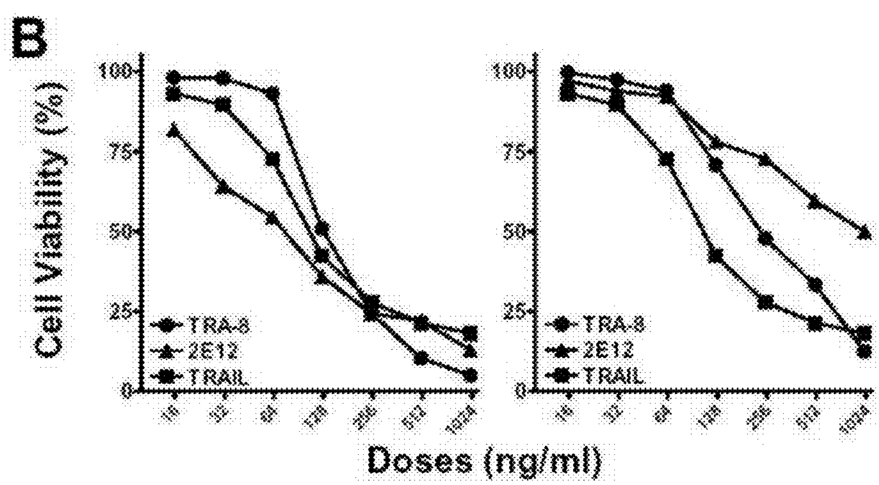
Figure 1C:
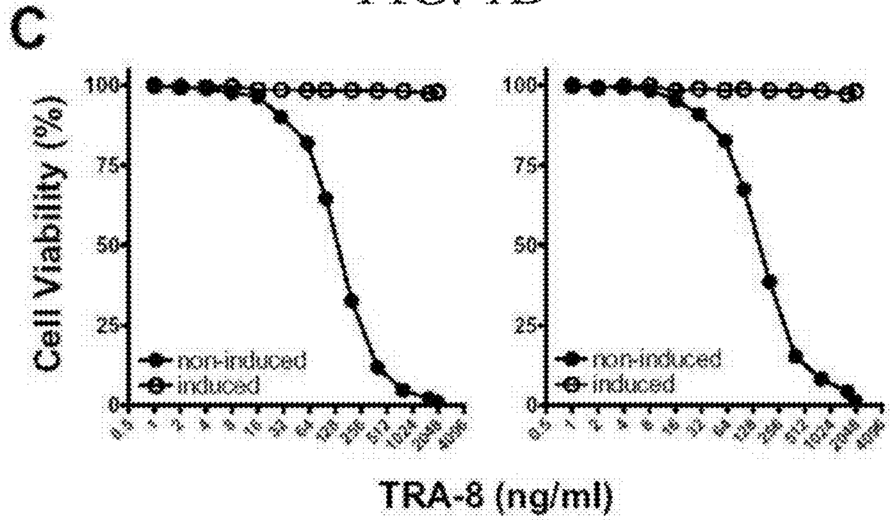

A human breast cancer cell line, MDA-231, and a human ovarian cancer cell line, UL-3C, were selected for induction of TRAIL-R2 resistance because they co-expressed high levels of cell surface TRAIL-R1 and -R2 as determined by two-color flow cytometry analysis using anti-TRAIL-R1 (2E12) and anti-TRAIL-R2 (2B4) antibodies (FIG. 1A). Two tumor cell lines were susceptible to apoptosis induced by agonistic anti-TRAIL receptors antibodies, 2E12 and TRA-8, as well as TRAIL as determined by in vitro cytotoxicity assay (FIG. 1B), indicating that both receptors for TRAIL are functional in two tumor cell lines. To determine whether these tumor cells develop apoptosis resistance to TRA-8 after treatment, cells were treated starting with a non-apoptosis dose (1 ng/ml) of TRA-8 for two days, and the doses were then doubled every two days until 2,000 ng/ml before withdraw of TRA-8. Cell viability was measured at each dose in both treated and non-treated cells. At TRA-8 doses lower than 10 ng/ml, there was no significant cell death in both treated and non-treated cells. When TRA-8 doses were increased to 50 ng/ml or higher, a TRA-8 dose-dependent reduction of cell viability was observed in non-treated cells. In contrast, there was no significant cell death in treated cells up to 2000 ng/ml (FIG. 1C). These results indicate that the repeated treatment of tumor cells with low, non-apoptosis-inducing doses of TRA-8 induces apoptosis resistance and that the induced resistance is not due to a selection process by removing apoptosis sensitive cells.

Figure 2A:
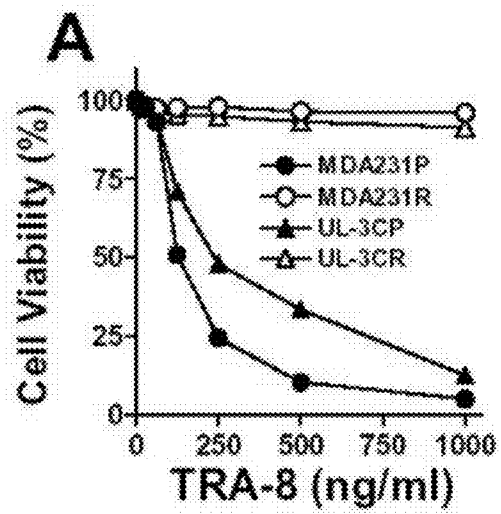
FIGS. 2A, 2B, 2C, and 2D show selectivity of induced TRA-8 resistance in MDA-231 and UL-3C cells.
Figure 2B:
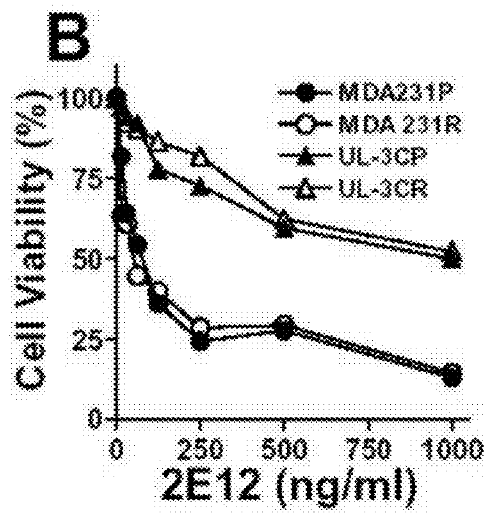
Figure 2C:
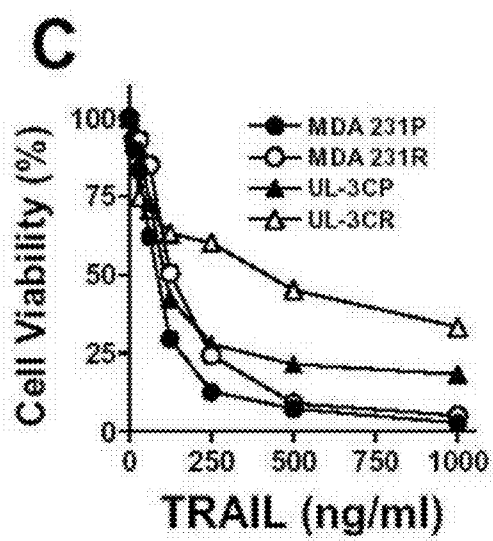
Figure 2D:
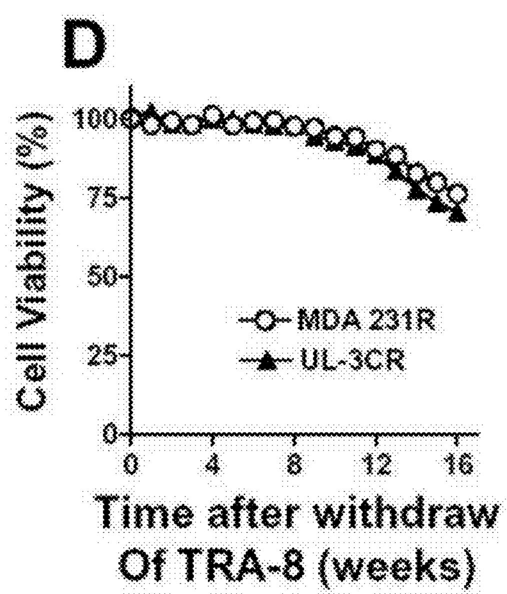

Four weeks after withdraw of TRA-8, both parental cells (MDA-231P, UL-3CP) and treated cells (MDA-231R, UL-3CR) were tested for their susceptibility to apoptosis induced by TRA-8, 2E12 or TRAIL. Compared to nearly 100% cell death of the parental cells after treatment with 1,000 ng/ml TRA-8, no significant cell death was induced in both MDA-231R and UL-3CR cells with a range of concentrations of TRA-8 (FIG. 2A), indicating that the cells become highly resistant to TRA-8-induced apoptosis. In contrast, the susceptibility of the TRA-8 resistant tumor cells to 2E12-induced apoptosis remained unchanged (FIG. 2B). Although the susceptibility was decreased, the induced TRA-8 resistant cells were still susceptible to TRAIL-mediated apoptosis (FIG. 2C). These results indicate that TRA-8-induced apoptosis resistance is selective for TRAIL-R2. After withdraw of TRA-8, the cells remained a TRA-8 resistant status for at least 3 months, and then the susceptibility was slowly restored to approximately 30% levels of the parental cells by four months (FIG. 2D), indicating that the induced resistance to TRA-8 was long lasting but partially reversible.

Induced TRAIL-R2 Resistance is not Due to Altered Cell Surface Expression or Mutation of TRAIL-R2 or an Intrinsic Apoptosis Defect.

Figure 3A:
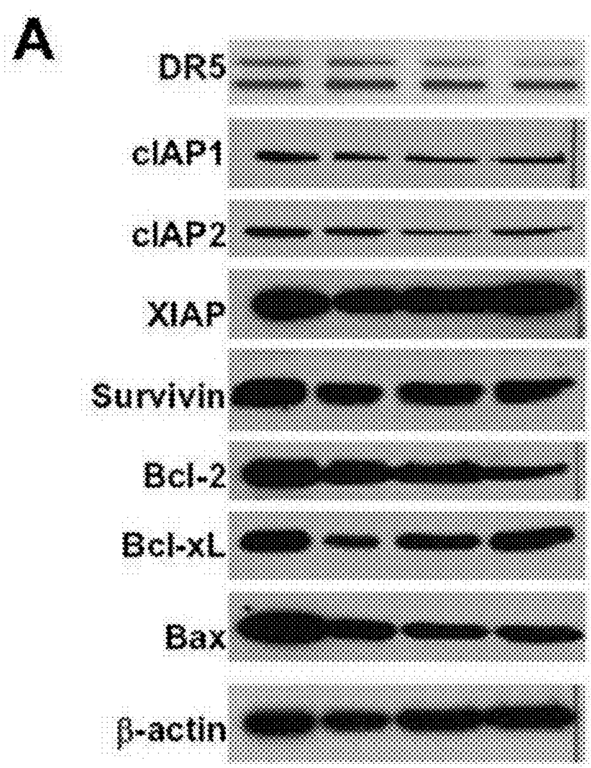
FIGS. 3A and 3B show TRAIL-R2 and associated apoptosis regulatory expression in TRA-8 resistant cells.

That TRA-8-induced apoptosis resistance was selective for TRAIL-R2 indicates that expression of TRAIL-R2 can be selectively reduced or a mutation of TRAIL-R2 can occur after induction of TRA-8 resistance. To rule out these possibilities, cell surface expression of TRAIL-R2 was examined, and it was determined that there was no alteration in expression levels of TRAIL-R2 in both TRA-8 resistant cells compared to their parental cells (FIG. 3A). This result was further confirmed by Western blot analysis showing that the two isoforms of TRAIL-R2 protein were equally expressed in parental and resistant cells (FIG. 3A). The full-length cDNA clones of TRAIL-R2 isolated from both TRA-8 resistant cell lines were sequenced, and no mutations were identified. These results indicated that the induced and selective resistance to TRAIL-R2 is not due to alterations of TRAIL-R2 itself.

Figure 3B:
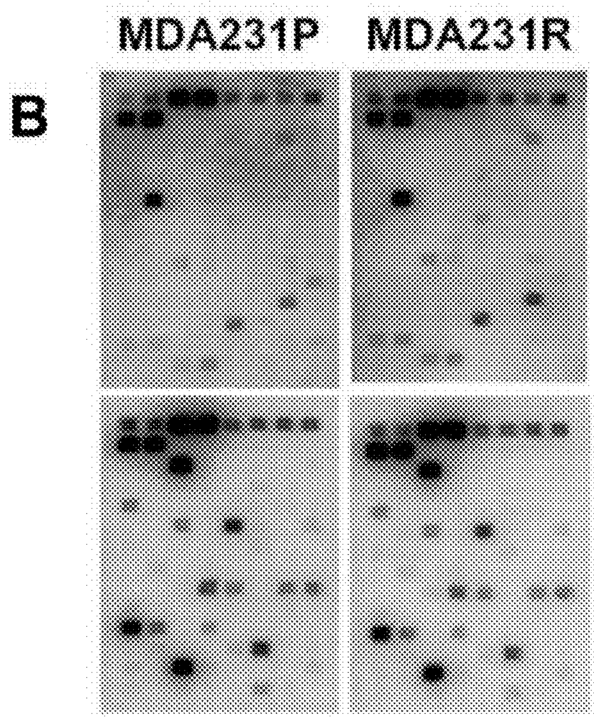

TRAIL-R2-mediated apoptosis can be regulated by a number of apoptosis regulatory proteins such as the inhibitor of apoptosis (IAP) family (Park, et al. 2002; Ng, et al. 2002; Roa, et al. 2003; Cummins, et al. 2004; Li, et al. 2004; Bockbrader, et al. 2005) and the Bcl-2 family (Hinz, et al. 2000; Rokhlin, et al. 2001; Fulda, et al. 2002; Carthy, et al. 2003; Chawla-Sarkar, et al. 2004; Sinicrope, et al. 2004). Using a panel of newly developed monoclonal antibodies, the protein levels of expression of cIAP1, cIAP2, XIAP, survivin, Bcl-2, Bcl-xL and Bax were examined by Western blot analysis. Although MDA231 and UL-3C expressed variable levels of these proteins, there was no significant difference between the parental and resistant cells (FIG. 3A), indicating that the expression levels of these proteins are unlikely involved in the induction of TRA-8. A more broad screening for potential transcriptional alterations among a panel of apoptosis- and cell signaling-associated genes was performed using membrane cDNA arrays (Superarray, Frederick, Md.), which included more than 200 well-known apoptosis-related genes (FIG. 3B, upper panel) and cell signaling genes (FIG. 3B, lower panel). A parallel comparison between MDA231 parental and resistant cells indicates that there was no significant alteration in the expression profile of these genes after induction of TRA-8-resistance.

Selective Blockade of TRAIL-R2 Apoptosis Signal Transduction in TRA-8 Resistant Tumor Cells.

Figures 4A, 4B:
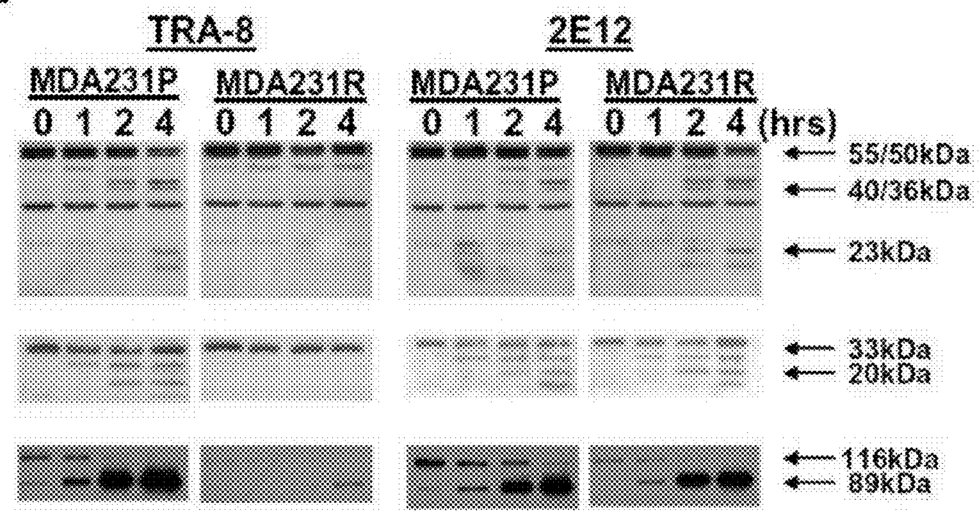
FIGS. 4A and 4B show activation of caspase pathway and JNK/p38 kinase pathway in TRA-8 resistant cells.

Sequential activation of upstream caspase 8 and downstream caspase 3 is a key event in TRAIL-R2 apoptosis signal transduction. Thus, time-dependent activation of these two caspases was examined. As shown previously, the treatment of TRA-8 sensitive parental MDA231 cells with TRA-8 induced activation of caspase 8 (FIG. 4A, upper panel) and caspase 3 (FIG. 4A, middle panel) as shown by generation of cleaved fragments of caspases after TRA-8 treatment. As a very sensitive marker of caspase activation, PARP was quickly cleaved (FIG. 4A, lower panel). However, activation of caspase 8, caspase 3 and subsequent cleavage of PARP did not occur in the resistant cells after TRA-8 treatment. The failure of activation of a caspase cascade is not due to an intrinsic defect in caspase pathways as the 2E12-triggered TRAIL-R1 caspase activation cascade was not impaired in TRA-8 resistant cells (FIG. 4A, left panel). These results indicate that the TRAIL-R2-associated caspase cascade is selectively blocked at the level of the upstream caspase 8 after induction of TRA-8 resistance.

Caspase 8-dependent activation of the JNK/p38 kinase pathway plays a critical synergistic role in TRAIL-R2-mediated apoptosis (Ohtsuka, et al. 2003; Ohtsuka, et al. 2002). The activation of the JNK/p38 kinases was measured by Western blot analysis of the phosphorylation of JNK/p38 kinases during TRA-8 treatment. Correspondent to caspase 8 activation, JNK (FIG. 4B, upper panel) and p38 (FIG. 4B, lower panel) were quickly phosphorylated in a time-dependent fashion. However, in TRA-8 resistant cells, only 2E12 but not TRA-8 was able to induce phosphorylation of the JNK/p38, indicating that the JNK/p38 kinase pathways are also selectively inhibited in TRA-8-resistant cells.

Selective Blockade of TRAIL-R2 Death Domain Function in TRA-8 Resistant Tumor Cells.

Figure 5A:
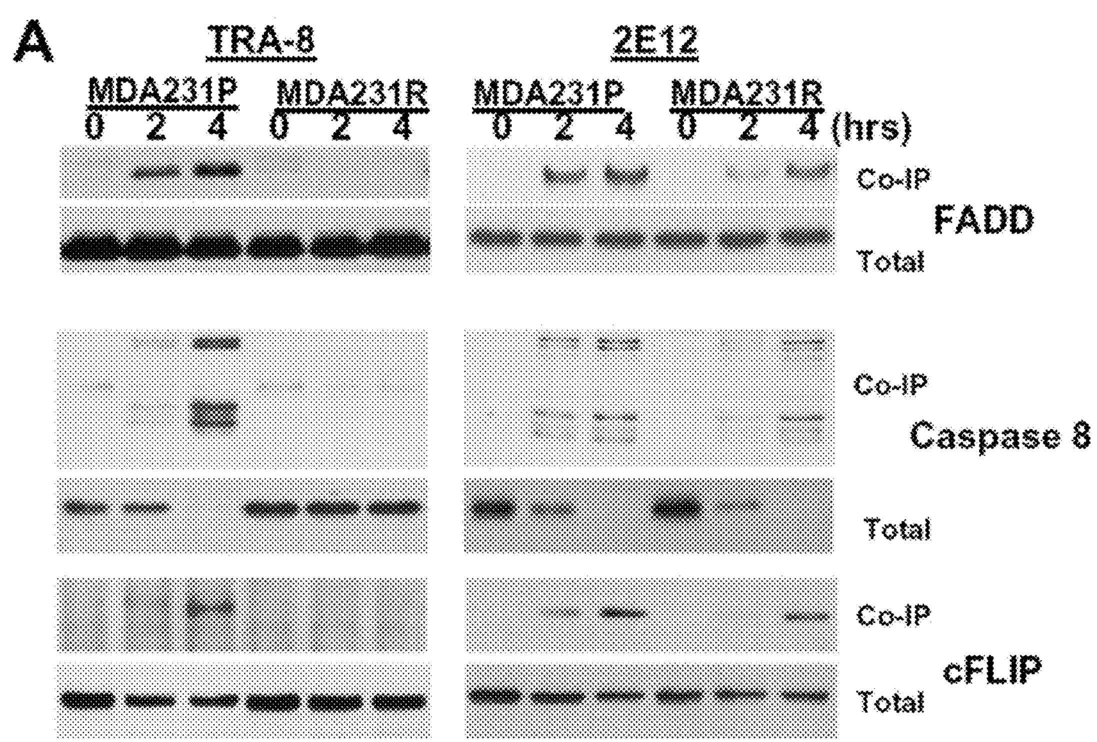
FIGS. 5A, 5B, 5C, 5D, and 5E show altered DISC formation in TRA-8 resistant cells.

As FADD and caspase 8 are recruited to the death domain of TRAIL-R2 and are major components of DISC, the capability of forming a DISC at TRAIL-R1 and TRAIL-R2 was examined in both parental and resistant cells by co-immunoprecipitation assay. In MDA231 parental cells, after treatment with TRA-8 or 2E12, there was a time-dependent increase of FADD (FIG. 5A, upper panel) and caspase 8 (FIG. 5A, middle panel), which were co-immunoprecipitated with TRAIL-R2 (FIG. 5A, left panel) or TRAIL-R1 (FIG. 5A, right panel), respectively. In TRA-8 resistant cells, there was no TRAIL-R2 co-immunoprecipited FADD and caspase 8 during TRA-8-mediated apoptosis, but the co-immunoprecipitation of FADD and caspase 8 with TRAIL-R1 after 2E12 treatment was not affected. Furthermore, to determine whether cFLIP, an inhibitory competitor for caspase 8 to the death domain, plays a role in the blockade of DISC formation, the co-immunoprecipitation of cFLIP with TRAIL-R1 and TRAIL-R2 was also examined. In a similar time-dependent pattern, cFLIP was co-immunoprecipited with TRAIL-R2 during TRA-8-mediated apoptosis in the parental cells but not in the resistant cells (FIG. 5A, lower panel). The co-immunoprecipitation of cFLIP with TRAIL-R1 during 2E12-mediated apoptosis was not different between the parental and TRA-8 resistant cells. Since there were similar levels of total protein expression of FADD, caspase 8 and cFLIP, the failure of the recruitment of these death domain-associated proteins is not due to defective expression of these proteins. These results indicate that the induced TRA-8 resistance is likely due to a selective defect for TRAIL-R2 to recruit FADD and caspase 8 in the formation of DISC after TRA-8 treatment.

Figure 5B:
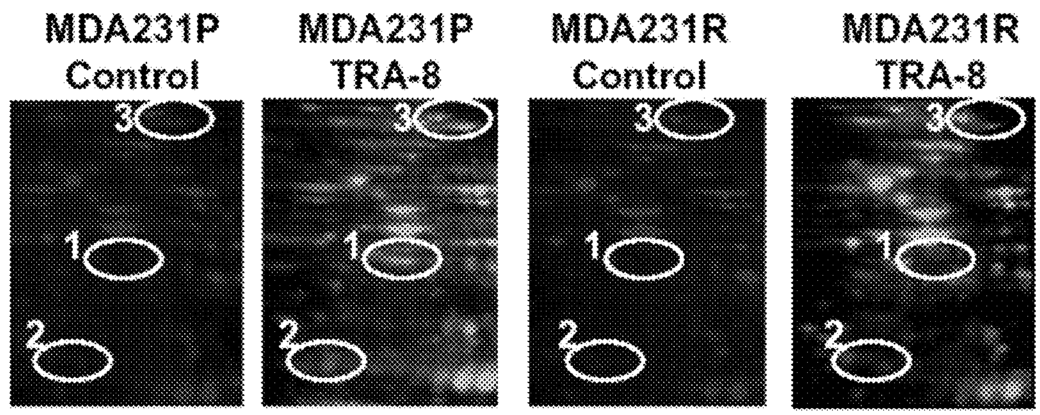
Figure 5C:
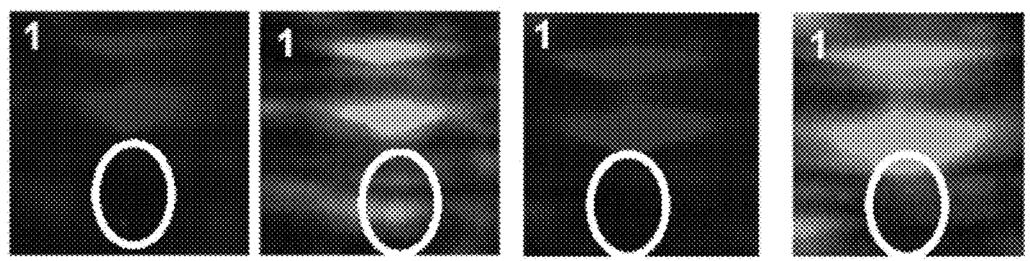
Figure 5D:
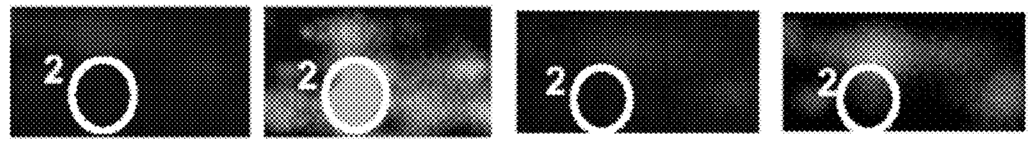
Figure 5E:
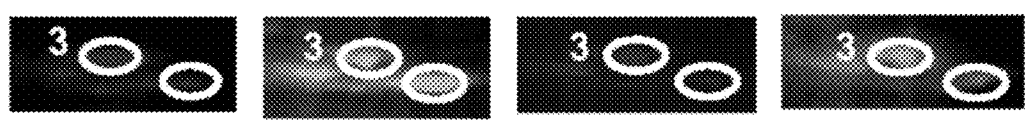

Failure of the assembly of DISC at the death domain of TRAIL-R2 in TRA-8 resistant cells indicates that the function and composition of TRAIL-R2 protein complex is altered, in which a newly generated or functionally altered protein can associate with TRAIL-R2 and prevent the recruitment of FADD and caspase 8 to the death domain of TRAIL-R2. Thus, the proteomic profiles of TRAIL-R2-associated proteins were compared in TRA-8-sensitive parental and TRA-8-resistant MDA231 cells before and after TRA-8 treatment by two dimension proteomic and mass spectrometry analysis. The differentially expressed proteins that were co-immunoprecipitated with TRAIL-R2 were analyzed by the PDQuest software, which led us to focus on three protein spots that were altered during TRA-8-mediated apoptosis between parental and resistant cells (FIG. 5B). The spot 1 and 2 representing a protein mass with a molecular weight of 50 kDa or 20 kDa, respectively, appeared only in MAD-231 parental cells after TRA-8 treatment but not in untreated cells and TRA-8-treated resistant cells, indicating that these proteins can are recruited to the TRAIL-R2 during TRA-8-mediated apoptosis. Based on their molecular weight and isoelectric point, the protein in the spot 1 was confirmed as caspase 8 (FIG. 5C), and the spot 2 as FADD (FIG. 5D) by Western blot analysis. The proteins in the spot 3 were interesting because they were constantly associated with TRAIL-R2 and a shift occurred during TRA-8-mediated apoptosis from a higher molecular weight protein to a lower molecular weight protein (FIG. 5E). This conversion appeared to be relevant to the induced TRA-8 resistance as it was only observed in TRA-8-treated MDA231 parental cells but not in resistant cells. Furthermore, mass spectrometry analysis identified both spots were derived from DDX3, a member of the DEAD-box RNA helicase family. Because a higher molecular weight form of DDX3 is constantly associated with TRAIL-R2 in TRA-8 resistant cells, it can be a factor that prevents the recruitment of FADD and caspase 8 to the death domain of TRAIL-R2.

Reversal of TRA-8 Resistance by Chemotherapeutic Agents.

Chemotherapeutic agents synergistically enhance TRA-8-mediated apoptosis both in vitro and in vivo (Ohtsuka, et al. 2003; Ohtsuka, et al. 2002; Buchsbaum et al. 2003), particularly in those TRA-8 resistant cells. To determine whether chemotherapeutic agents are able to reverse induced TRA-8 resistance, the effect of a group of chemotherapeutic agents, Adriamycin, Taxol, Cisplatin and Bisindolymaleimide VIII (BisVIII), were examined on TRA-8-mediated apoptosis of the induced resistant cells. In the presence of indicated concentrations of chemotherapeutic agents, a TRA-8 dose-dependent response was restored in both TRA-8 resistant MDA-231 and UL-3C cells (FIG. 6A), indicating that all chemotherapeutic agents are able to reverse TRA-8-induced resistance. Activation of the caspase cascade in MAD-231 resistant cells after combination treatment with Adriamycin and TRA-8 was examined using a panel of monoclonal anti-caspase antibodies. As anti-caspase 8 (clone: 2F4) and anti-caspase 2 (clone: 2A3) only recognize the pro-forms of caspase 8 and 2, respectively, the activation of caspase 8 and 2 was demonstrated by reduced amount of the pro-forms due to the cleavage. Anti-caspase 9 (Clone: 4B4) and anti-caspase 3 (clone: 1H6) recognize both pro- and cleaved forms of caspase 9 and 3, respectively, their activation was shown by the presence of the cleaved fragments of caspase 9 and 3. The single agent treatment alone with TRA-8 (FIG. 6B, lane 5) or Adriamycin (FIG. 6B, lane 4) at 4 hours did not induce any significant activation of all tested caspases compared to non-treated controls (FIG. 6B, lane 1). In contrast, activation of caspase 2, 9 and 3 was induced as early as one hour after combination treatment with Adriamycin and TRA-8 (FIG. 6B, lane 2), which was further enhanced at the four hour time point (FIG. 6B, lane 3). Activation of caspase 8 was evident at four-hour time point after combination treatment. These results indicate that treatment with Adriamycin restored TRAIL-R2-associated caspase cascade in TRA-8 resistant cells. In the presence of Adriamycin, TRA-8 was able to trigger the recruitment 5 of FADD to TRAIL-R2 (FIG. 6C, lane 2 and 3), the recruiting function of TRAIL-R2 was restored by Adriamycin treatment.

Example 2

Role of DDX3 in TRAIL-R2-Mediated Apoptosis

Materials and Methods

Cell Lines, Antibodies, and Reagents.

Human breast cancer cell line, MDA-MB-231, was purchased from the American Tissue Culture Collection (ATCC) (Manassas, Va.). Human ovarian cancer cell line, UL-3C, was obtained. Cells were maintained in DMEM or RPMI1640 supplemented with 10% heat-inactivated FCS, 50 ng/ml streptomycin, and 50 U/mL penicillin (Cellgro, Medi-atec, Inc., Herndon, Va.). Anti-human TRAIL-R1 (clone: 2E12) and anti-human TRAIL-R2 (clone: TRA-8) monoclonal antibodies were previously described (Ichikawa et al., 2003; Ichikawa et al., 2001). Anti-human TRAIL-R2 (clone: 2B4) was developed for flow cytometry and immunoprecipitation assays. Recombinant soluble TRAIL was purchased from Alexis Biochemicals (San Diego, Calif.). Polyclonal anti-caspase 3 and anti-caspase 8 antibodies were purchased from BD Pharmingen (San Diego, Calif.). Monoclonal anti-human caspase 2, 3, 8, 9 and 10 antibodies, and monoclonal anti-human Bcl-2, Bcl-xL, Bax, cIAP-1, cIAP-2, XIAP, and survivin antibodies, were prepared. Anti-PARP antibody was purchased from Cell Signaling Technology, Inc. (Beverly, Mass.). Anti-β-actin antibody was purchased from Sigma. Anti-FADD were purchased from Transduction Laboratories (Lexington, Ky.). All horseradish peroxidase (HRP)-conjugated secondary reagents were purchased from Southern Biotechnology Associates, Inc. (Birmingham, Ala.). Active Caspase-1, Caspase-2, Caspase-3, Caspase-6, Caspase-7, Caspase-8, Caspase-9, and Caspase-10 were purchased from EMD Biosciences, Inc (San Diego, Calif.). The fluorogenic peptide derivatives Ac-Val-Asp-Val-Asp-AMC (Ac-VDVAD-AMC, 260060M001, SEQ ID NO:40), Ac-Asp-Glu-Val-Asp-amino-4-methylcoumarin (Ac-DEVD-AMC, 260031M001, SEQ ID NO:41), and Ac-carbonyl-11e-Glu-Thr-Asp-7-amido-4-methylcoumarin (Z-IETD-AMC, 260042M001, SEQ ID NO:42) were purchased from Alexis Biochemicals, San Diego, Calif. Caspase-2, -3, -8, -10 inhibitor (FMKSP01) were purchased from R&D Systems, Inc.

Cytotoxicity analysis of tumor cell susceptibility to TRA-8, 2E12, and TRAIL-mediated apoptosis. Cells (1,000 cells per well) were seeded into 96-well plates in triplicate with eight concentrations (double serial dilutions from 1000 ng/ml) of TRA-8, 2E12, or TRAIL. Cell viability was determined after overnight culture using an ATPLITE™ assay according to the manufacturer's instructions (Packard Instruments, Meriden, Conn.). The results are presented as the precentage of viable cells in treated wells compared to medium control wells.

3 ml wash with FACS buffer, 10,000 cells per sample were analyzed by FACSCAN flow cytometer (BD Biosciences, San Jose, Calif.).

Western Blot Analysis of Apoptosis-Associated Proteins.

Tumor cells ($3\times10^6$) were washed twice with cold PBS and lysed with 300 μl lysis buffer containing 10 mM Tris-HCl (pH 7.6), 150 mM NaCl, 0.5 mM EDTA, 1 mM EGTA, 0.1% SDS, 1 mM sodium orthovanadate, and a mixture of protease inhibitors (1 mM phenylmethylsulfonyl fluoride, 1 ng/ml pepstatin A, 2 ng/ml aprotinin). The cell lysates were sonicated for 10 seconds and centrifuged for 20 minutes at 12,000 g. The cell lysates with equal amounts of total proteins were boiled for 5 minutes with SDS-PAGE sample buffer. Total cell lysates were separated in 8%, 10%, or 12% SDS-PAGE, and electrophoretically transferred to a nitrocellulose membrane. The blots were blocked with 5% nonfat dry milk in TBST buffer (20 mM Tris-HCl (pH 7.4), 500 mM NaCl, and 0.1% Tween 20) and incubated with primary antibody in blocking buffer at 4° C. overnight. The blots were washed three times with TBST and probed with HRP-conjugated secondary antibodies for 1 hour at room temperature. After being washed four times with TBST, the probed proteins were visualized using the ECL Western blotting detection system (Amersham Biosciences) according to the manufacturer's instructions.

Under-Expression of DDX3.

Design RNAi: An online design tool, BLOOK-iT RNAi Designer (Invitrogen), was used to identify RNAi targets for DDX3. Five targeted shRNA sequences were selected from the top 10 highest scoring RNAi targets (see Table 2).

TABLE 2 shRNA orientation: SENSE-loop-ANTISENSE

| Construct | | Strand | Sequence | |
|---|---|---|---|---|
| 1 | 108-123 | top | CACCAAGCTTGCGCTATATTCCTCCTCATTTcgaaAAAT GAGGAGGAATATAGCGCCTCGAG | SEQ ID NO: 8 |
| | | bottom | AAAACTCGAGGCGCTATATTCCTCCTCATTTttcgAAAT GAGGAGGAATATAGCGCAAGCTT | SEQ ID NO: 9 |
| 2 | 562-582 | top | CACCGGAGAAATTATCATGGGAAACcgaaGTTTCCCAT GATAATTTCTCC | SEQ ID NO: 10 |
| | | bottom | AAAAGGAGAAATTATCATGGGAAACttcgGTTTCCCAT GATAATTTCTCC | SEQ ID NO: 11 |
| 3 | 1554-1574 | top | CACCGCCAAGTGATATTGAAGAATAaacgTATTCTTCA ATATCACTTGGC | SEQ ID NO: 12 |
| | | bottom | AAAAGCCAAGTGATATTGAAGAATAcgttTATTCTTCAA TATCACTTGGC | SEQ ID NO: 13 |
| 4 | 5'UTR | top | CACCGCTTTCCAGCGGGTATATTAGcgaaCTAATATACC CGCTGGAAAGC | SEQ ID NO: 14 |
| | | bottom | AAAAGCTTTCCAGCGGGTATATTAGttcgCTAATATACC CGCTGGAAAGC | SEQ ID NO: 15 |
| 5 | 1045-1065 | top | CACCGCTGATCGGATGTTGGATATGcgaaCATATCCAA CATCCGATCAGC | SEQ ID NO: 16 |
| | | bottom | AAAAGCTGATCGGATGTTGGATATGttcgCATATCCAAC ATCCGATCAGC | SEQ ID NO: 17 |

Flow Cytometry.

Cells ($10^6$) were washed once with PBS and resuspended in 1 ml cold FACS buffer (PBS with 5% FBS and 0.01% $NaN_3$) containing the primary antibody (1 ng/ml of TRA-8). Cells were stained on ice for 60 minutes, then washed with 3 ml cold FACS buffer, and incubated with the secondary antibody (1:100 dilution of PE-conjugated goat anti-mouse IgG) at 4° C. for 60 minutes in the dark. After an additional They were then cloned into the BLOCK-iT U6 entry vector. The shRNA is driven by the U6 promoter and can be transiently expressed in most dividing or nondividing mammalian cell types. Resistant cells were transfected with RNAi used LIPOFECTAMINE 2000 (Invitrogen) for the RNAi response. The decreased DDX3 expression was determined by Western blot analysis using anti-DDX3 antibody 36 hours after transfection. Once decreased DDX3 expression was achieved, the siRNA oligo was synthesized (Target sequence: GGAGAAATTATCATGGGAAAC (SEQ ID NO:27): Sense RNA 5'-Fl-GGAGAAATTATCATGGGAAAC (Fl-SEQ ID NO:27) (Fl=fluorescein); Anti-senseRNA 5'-GUUUCCCAUGAUAAUUUCUCC-3' (SEQ ID NO:28), and RNAi control oligo (RI-010-DP) was purchased from Molecula (Columbia, Md.).

Generation of Expression Vectors.

The full-length DDX3 was cloned into pcDNA3.1 plasmid (Invitrogen) with a His tag at the N-terminus of DDX3. DDX3 and TRAIL-R2 cDNA was generated by reverse transcriptase polymerase chain reaction (RT-PCR) performed with total RNA extracted from MDA231 cells using the following primer pair: DDX31 forward primer with BamHI: 5'-acggatccaaatgagtcatgtggcagtgga-3' (SEQ ID NO:29); DDX3662 reverse primer with xhoI: 5'-ctctcgagcaaagcaggctcagttaccc-3' (SEQ ID NO:30). TRAIL-R21 forward primer with KpnI: 5'-aaaggtaccagccatggaacaacggggacag-3' (SEQ ID NO:31); TRAIL-R2441 reverse primer with EcoV: 5'-aaagatatcttaggacatggcagagtctgcatt-3' (SEQ ID NO:32); the isolated polymerase chain reaction fragment of DDX3 was in frame into pcDNA3.1-His vector (Invitrogen). TRAIL-R2 cDNA was cloned into the pshutter-CMV vector. The correct sequences were confirmed by DNA sequencing.

DDX3/pcDNA3.1-His expression plasmid was generated by deleting the DDX3 sequence between the BamHI and xhoI sites. DDX3151 forward primer with BamHI: 5'-acggatccaaatgttttctggaggcaacactggg-3' (SEQ ID NO:33); TRAIL-R2/pshutter-CMV expression plasmid was generated by deleting the TRAIL-R2 sequence using the following primer: TRAIL-R2340 reverse primer with EcoRV: 5'-aaagatatcttactgtctcagagtctcagtgggatc-3' (SEQ ID NO:34); TRAIL-R2330 reverse primer with EcoRV and xhoI: 5'-aaagatatcctcgagatttgctggaaccagcagcct-3' (SEQ ID NO:35).

Constructions of Expression Plasmids for DDX3 in Bacteria.

DDX3 or cIAP1 fragment was inserted into the TOPO100 vector (Invitrogen). The resulting plasmids were transformed into the *E. coli* strain BL21 (DE3), which was grown in LB media to exponential phases and induced with 0.4 mM isopropyl-1-thio-β-D-galactopyranoside for 3 hours. Cells were pelleted, resuspended in lysis buffer (30 mM Tris-HCl, pH 7.5, 0.1 mM NaCl, 1 mM DTT, 0.1 mM EDTA, 1% Nonidet P-40, and 20 μg/ml PMSF), and sonicated. The supernatant after centrifugation at 14,000×g for 15 minutes was purified by Ni column. The protein concentration was determined by BCA assay (Pierce, Rockford, Ill.), and ali-quots were stored at 80° C.

Transient Transfections of 293 or 3T3 Cells.

293 or 3T3 cells were transfected with expression vectors using LIPOFECTAMINE™ 2000 (Invitrogen, Inc.). After 24 hours transfection, protein expression was determined by Western blot analysis using respective monoclonal antibody. For co-immunoprecipitation analysis, cells were lysed with immunoprecipitation-lysis buffer containing a protease inhibitor cocktail.

Co-Immunoprecipitation Assay.

Anti-DDX3 or anti-TRAIL-R2 antibody was conjugated to Sepharose beads (Sigma). The composition of the TRAIL-R2 DISC was determined as follows. $5\times10^6$ cells (if not otherwise indicated) were treated with 500 ng/ml of TRA-8 for the indicated time at 37° C. and then lysed in immunoprecipitation-lysis buffer (20 mM Tris-HCl, pH 7.4, 150 mM NaCl, 0.2% NONIDET P40, and 10% glycerol and complete protease inhibitor cock-tail) or lysed without treatment (unstimulated condition). The TRAIL-R2 DISC was then precipitated overnight at 4° C. with 30 μl beads. After immunoprecipitation, the beads were washed four times with lysis buffer. The beads were then washed five times with 10 mM Tris buffer and resuspended in loading buffer for SDS-PAGE and immunoblotting analyses.

Assay of Caspase Activity In Vitro.

Fluorometric assays were conducted in 96-well clear bottom plates, and all measurements were carried out in triplicate wells. 100 μl of assay buffer (10 mM HEPES pH 7.0, 50 mM NaCl, 2 mM $MgCl_2$, 5 mM EDTA, and 1 mM DTT) was added. Active caspase-8 and peptide substrates (Ac-IETD-AMC) were added to each well to a final concentration of 100 ng/μl. Co-immunoprecipitation eluted fraction was added to start the reaction. Background fluorescence was measured in wells containing assay buffer, substrate, and lysis buffer without the cell lysates. Assay plates were incubated at 37° C. for 1 hour. Fluorescence was measured on a fluorescence plate reader (Bio-Tek, Winooski, Vt.) set at 355-nm excitation and 440-nm emission.

In Vitro Caspase Cleavage Assay.

The ability of caspases to cleave DDX3 was examined in an in vitro assay. The cleavage reactions carried out for 30 min at 37° C., including 10 ul of eluted fraction from TRAIL-R2 co-IP, 10 ul of reaction buffer (10 mM HEPES [pH 7.0], 50 mM NaCl, 2 mM $MgCl_2$, 5 mM EGTA, 1 mM DTT, 2 mM ATP), and 5 ul (0.1 U/μl) recombinant active forms of caspases. The cleavage was determined by Western blot with anti-DDX3 antibody.

Results

Proteomics Analysis of a Candidate Protein, DDX3, that Causes a Blockade of the Death Domain of TRAIL-R2 in Resistant Cells.

The spontaneously developed or induced apoptosis resistance to the therapeutic agents, TRAIL and agonistic antibodies, that target the death receptors represents a major obstacle in effective treatment of cancer with these agents. In order to determine whether alternative compositions of TRAIL-R2 death domain complexes in resistant cells, the proteomic profiles of existing TRAIL-R2-associated proteins were compared in TRA-8-sensitive parental and TRA-8-resistant MDA231 cells before and after TRA-8 treatment by two-dimensional proteomic and mass spectrometry analysis. In the examination of two-dimensional gels stained with SYPRO™ ruby (Molecular Probes, Eugene, Oreg.), a protein spot about ~80 KDa was found. The association of this protein with TRAIL-R2 block the formation of TRAIL-R2 DISC, thereby causing TRA-8 resistance. The ~80 kd protein was excised from SDS-PAGE and digested with trypsin, and peptide sequences were analyzed by mass spectrometry. The protein amino acid sequences from six digested fragments were 100% identical to the Genbank sequence of human DDX3 (Table 3), indicating that DDX3 disassociates from TRAIL-R2 during TRA-8-induced apoptosis correlated to DISC formation. If this protein remains associated with the TRAIL-R2-associated protein complex, it can prevent FADD recruitment and cause failure of DISC formation.

TABLE 3

DDX3 Fragments

| Peptide | Sequence | DDX3 | SEQ ID |
|---|---|---|---|
| 1 | HVINFDLPSDIEEYVHR | aa512-528 | SEQ ID NO: 1 |
| 2 | DFLDEYIFLAVGR | aa395-407 | SEQ ID NO: 2 |

TABLE 3-continued

| DDX3 Fragments | | | |
|---|---|---|---|
| Peptide | Sequence | DDX3 | SEQ ID |
| 3 | DLLDLLVEAK | aa555-564 | SEQ ID NO: 3 |
| 4 | SFLLDLLNATGK | aa429-440 | SEQ ID NO: 4 |
| 5 | TAAFLLPILSQIYSDGP GEALR | aa231-252 | SEQ ID NO: 5 |
| 6 | QYPISLVLAPT | aa265-275 | SEQ ID NO: 6 |

DDX3 is a Novel TRAIL-R2-Associated Protein in TRAIL-R2-Mediated Apoptosis.

Figures 8A, 8B:
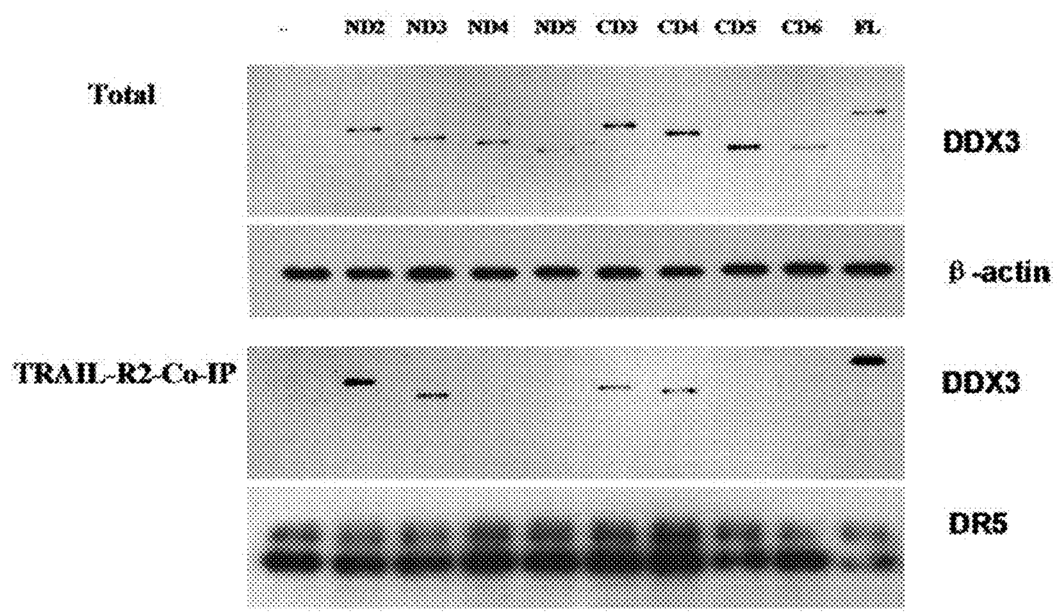
FIGS. 8A, 8B, 8C, 8D, 8E, 8F, 8G, and 8H show mapping of the interaction region of DDX3 and TRAIL-R2.

To determine whether DDX3 is indeed associated with TRAIL-R2, the full-length (aa1-662), N-terminal fragment (aa1-316), and a C-terminal fragment (aa310-662) of DDX3 were cloned into PcDNAIII3.1 with 6-His tag at the N-terminus. These expression vectors were transfected into MDA231 parental cells to achieve overexpression of the recombinant full-length and deletion mutants of DDX3. However, only full-length DDX3, not its N-terminal and C-terminal deletion mutants, was associated with TRAIL-R2 as detected by co-immunoprecipitation analysis followed by Western blot analysis using anti-6-His antibody (FIG. 8A). These results confirmed that DDX3 associated with TRAIL-R2 and its binding to TRAIL-R2 are full-length dependent. DDX3 was immunoprecipitated with anti-TRAIL-R2 in MDA231 cells.

Figure 7A:
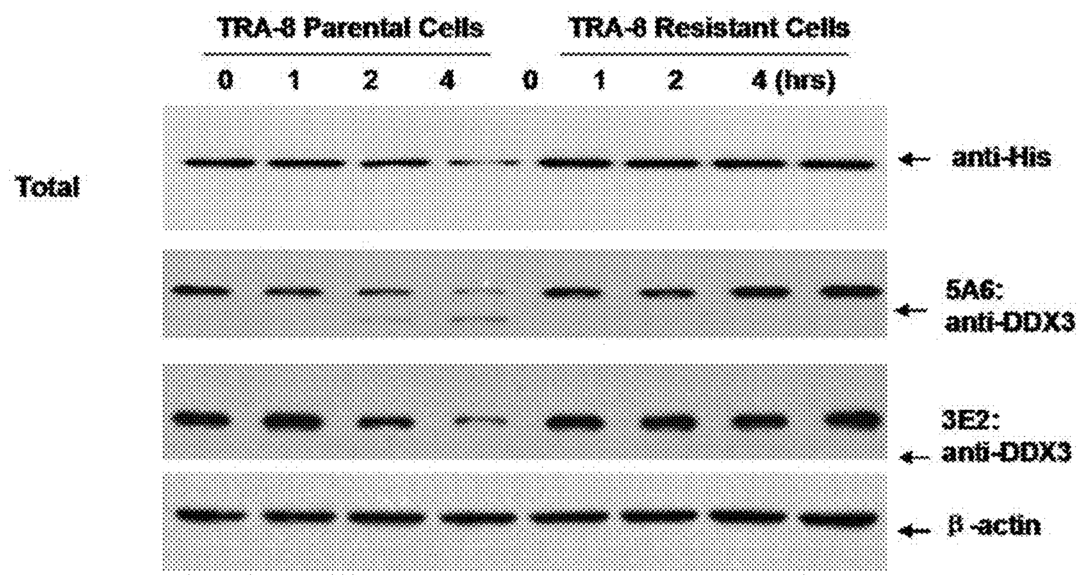
FIGS. 7A and 7B show DDX3 association with TRAIL-R2. MDA231 parental cells and resistant cells were transfected with the recombinant full-length DDX3. 48 hours after transfection, cells were treated with 500 ng/ml TRA-8 for the indicated time. Total cell proteins were probed with monoclonal anti-His antibody (FIG. 7A). β-actin was used as the loading control. Co-immunoprecipitation assay of recombinant DDX3 associated with TRAIL-R2 determined using anti-His antibody (FIG. 7B). To analyze endogenous DDX3 associated with TRAIL-, MDA231 parental cells and resistant cells were treated with 500 ng/ml TRA-8 for the indicated time. TRAIL-R2 was immunoprecipitated with 2B4-conjugated Sepharose 4B. Total cell proteins were probed with monoclonal anti-DDX3 antibodies, 3E2 and 5A6 (FIG. 7A). The co-immunoprecipitated endogenous DDX3 was probed with monoclonal anti-DDX3 antibodies, 3E2 and 5A6 (FIG. 7B). TRAIL-R2 in parental cells and resistant cells were determined by Western Blot with anti-TRAIL-R2 polyclonal antibody.
Figure 7B:
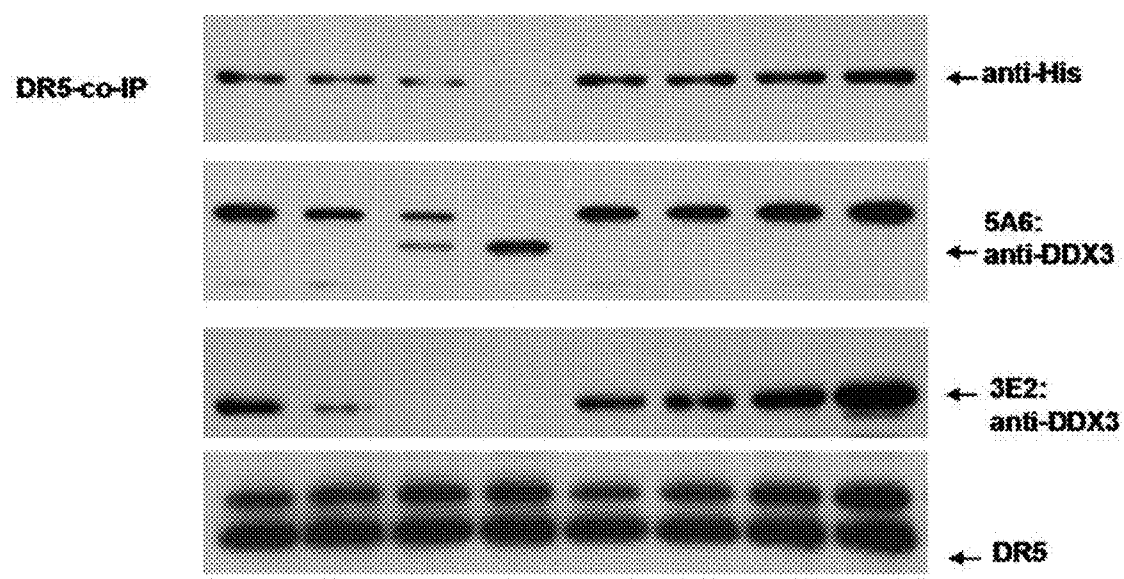

To further confirm that association of DDX3 with TRAIL-R2, N-terminal, C-terminal fragment, and full-length versions of DDX3 were expressed in *E. coli*. Proteins were purified and used as an antigen to generate polyclonal and a panel of monoclonal antibodies against DDX3. TRAIL-R2-associated DDX3 was detected by co-immunoprecipitation and Western blot analysis using mouse anti-DDX3 monoclonal antibody. The results demonstrated that DDX3 was co-immunoprecipitated with TRAIL-R2 in both nonapoptotic parental and resistant cells (FIG. 7). There was a time-dependent decrease of DDX3 in TRA-8-sensitive cells but not in TRA-8-resistant cells during apoptosis. In addition, by Western blot analysis, a rapid decrease and cleavage of TRAIL-R2-associated DDX3 during TRA-8-induced apoptosis was observed. This indicated that the cleavage of DDX3 is caspase-dependent. Based on these results, the DDX3 sequence was scrutinized for potential cleavage sites at the N-terminal, and a relatively conserved caspase cleavage motif DKSDEDD (SEQ ID NO:46) was found at amino acids 129-135. It is apparent that cleavage occurs on the DISC and results in a critical functional element of DDX3 being released from TRAIL-R2. The data were compatible with the latter model, which suggests that initiated caspase is rapidly recruited to TRAIL-R2 and cleaves DDX3 readily. In addition, FADD and caspase-8 associate with and recruit to TRAIL-R2 to form DISC, which in turn leads to caspase cascade activation correlated to the TRAIL-R2-associated DDX3 cleavage, this indicates that in certain circumstances DDX3 is essential for the apoptotic program, illustrating that DDX3 associates with TRAIL-R2 involved TRAIL-R2-mediated apoptosis resistance.

Mapping Interaction Region of DDX3 with TRAIL-R2.

In order to better understand the regulation of DDX3 in TRAIL-R2-mediated signal transduction, the approximate DDX3 region that is required for binding TRAIL-R2 was determined using HEK293A cells that had been transiently transfected with plasmids encoding deletion mutants of DDX3 (FIGS. 8A-B). The interaction of recombinant DDX3 and TRAIL-R2 was determined by co-immunoprecipitation using TRA-8. Full-length DDX3, DDX3Δ201-662, or DDX3Δ1-400 bound to TRAIL-R2. However, neither DDX3Δ251-662 nor DDX3Δ1-350 could bind to TRAIL-R2 (FIGS. 8A-B), this indicates that DDX3 has two binding motifs at TRAIL-R2. One is located at the N-terminus (aa 200-250); the other is adjacent to aa 350-400. Western blot analysis of lysates from the same cells confirmed the production of comparable amounts of wild-type DDX3 and deletion fragments of DDX3, which exclude differences in protein expression as an explanation for these results.

Figure 8C:
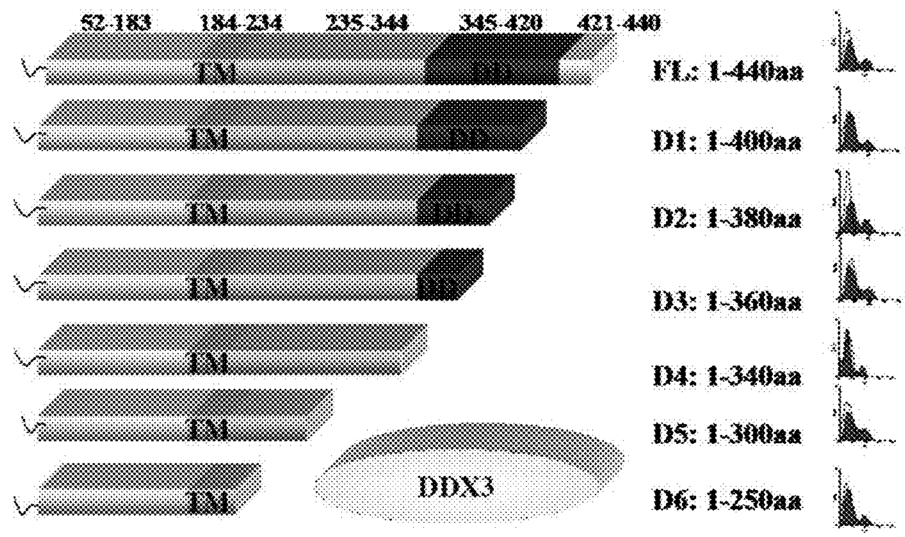
Figure 8D:
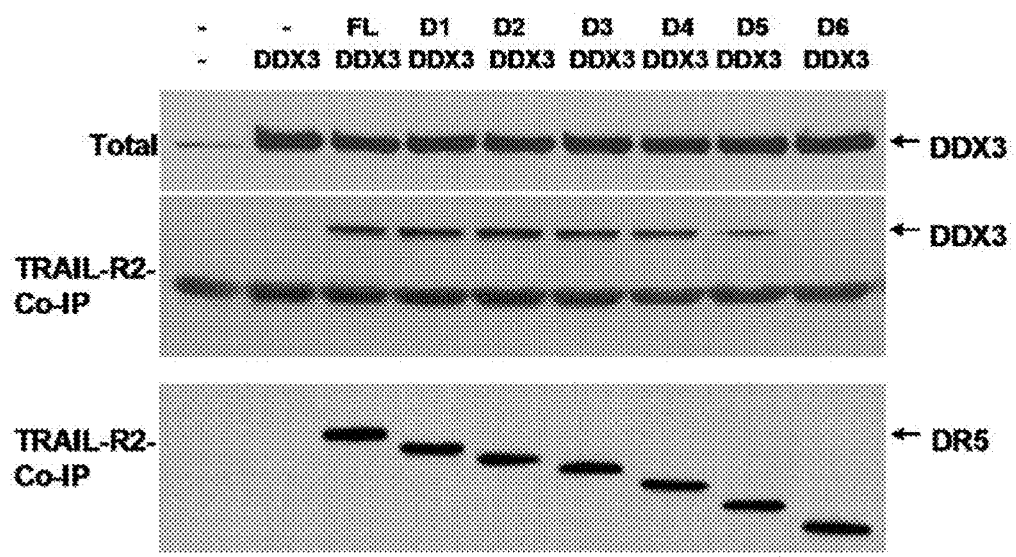
Figure 8E:
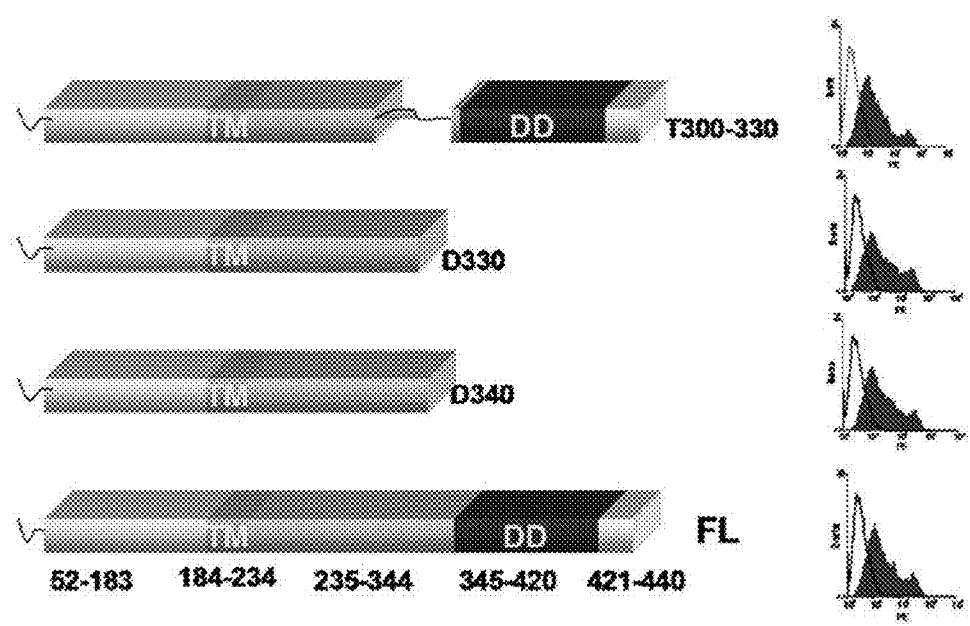
Figure 8F:
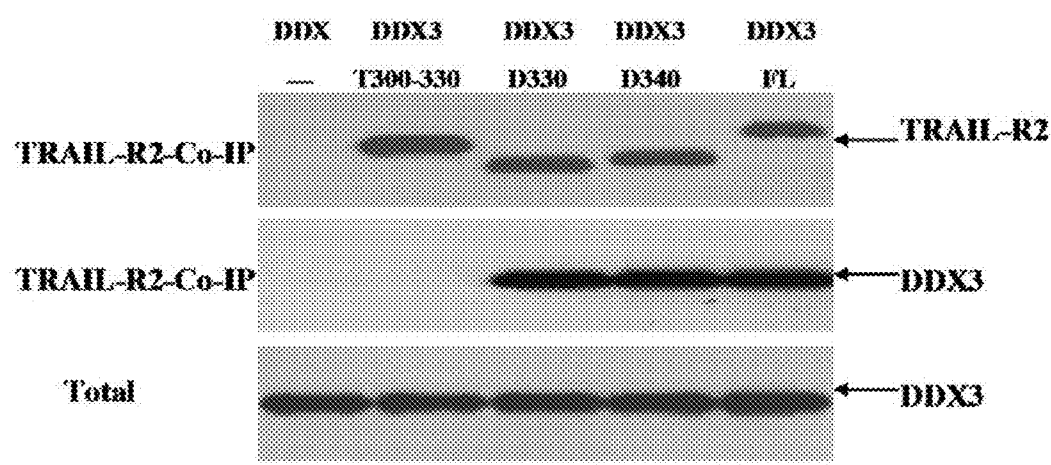
Figures 8G, 8H:
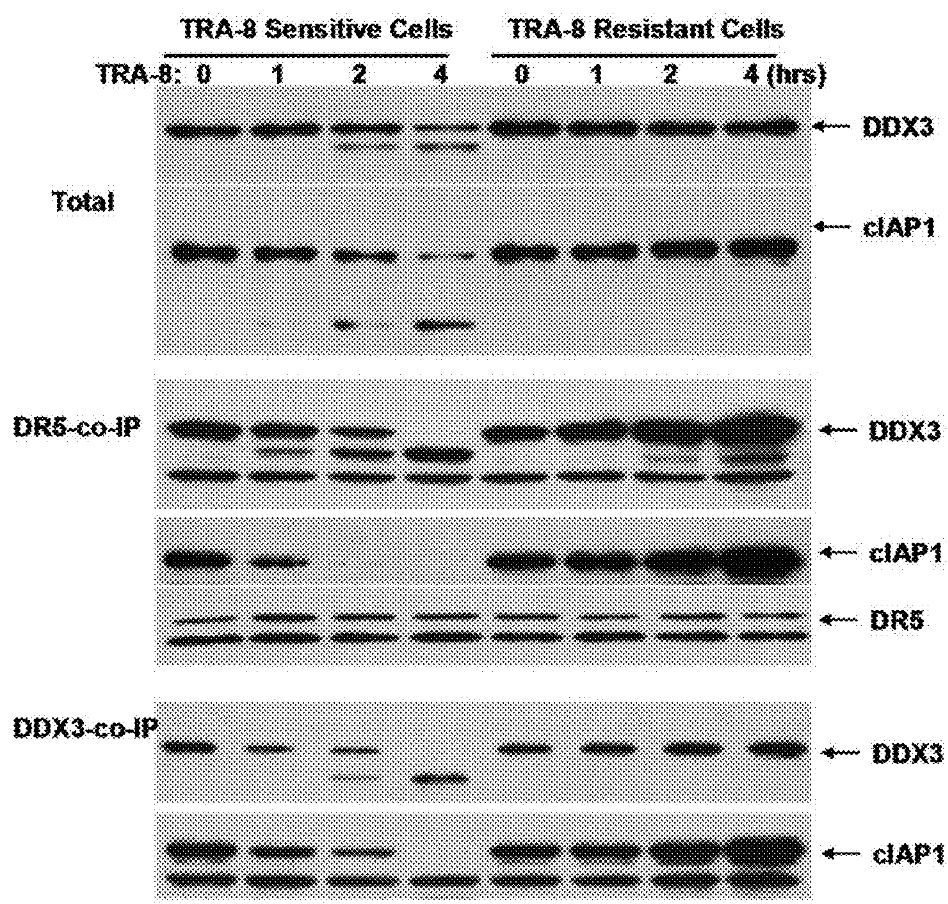

DDX3 is permanently associated with TRAIL-R2 and correlates with the blockade of FADD recruitment in TRA-8-resistant cells, indicating that the TRAIL-R2-associated DDX3 prevents the recruitment of FADD. There can be a connection between DDX3 and FADD through TRAIL-R2. To test whether DDX3 and FADD share a common binding motif at the death domain of TRAIL-R2 or the two binding motifs are close together, so that pre-engaged DDX3 interferes with the recruitment of FADD, the location of the DDX3-binding domain in TRAIL-R2 was determined Vectors encoding the full-length TRAIL-R2, and a series of amino-terminal domain deletion of TRAIL-R2 including complete deletion of death domain were constructed (FIGS. 8C-D). In an analogous approach to assess the function of DDX3, and to exclude endogenous human TRAIL-R2, a murine fibroblast cell line, NIH3T3, was chosen as the host cell for the co-expression of human TRAIL-R2 and DDX3. 3T3 cells were co-transfected with plasmids encoding His-tagged DDX3 and full-length TRAIL-R2, DDX3 and a series of deletion mutants of TRAIL-R2, and DDX3 alone. Cell surface TRAIL-R2 expression was examined by flow cytometry using TRA-8 staining. All transfected cells exhibited similar levels of cell surface TRAIL-R2 (FIGS. 8C-D), indicating that deletion of the intracellular domain did not alter cell surface TRAIL-R2. In addition, all transfected cells expressed similar levels of recombinant DDX3, as detected by Western blot analysis of total cell lysates using the anti-6-his antibody. The association of recombinant DDX3 with the deletion mutants of TRAIL-R2 was examined by co-immunoprecipitation with TRA-8 and Western blot analysis with anti-6-His antibody (FIG. 8D). The interaction of TRAIL-R2 with DDX3 is independent of the death domain of TRAIL-R2. To further define the TRAIL-R2 binding motif more accurately, further deletion mutants of TRAIL-R2, D330, and the truncation of TRAIL-R2 (T300-330) were constructed (FIGS. 8E-F), co-transfected with DDX3 into 3T3 cells, and analyzed for their interactions. The results demonstrated that DDX3 did not bind to the TRAIL-R2 death domain but rather to a membrane proximal region (aa 300-330) close to the death domain (aa 340-aa 420) (FIG. 8F). This indicates that DDX3 might play a different role from previously identified death domain-associated proteins in TRAIL-R2 signaling. In addition, this region is highly homologous with TRAIL-R1 and DcR2 (FIG. 8G). These data indicate that DDX3 is a common adaptor protein associated with members of the death receptor family.

DDX3 Contains CARD.

The functional significance of DDX3 in TRAIL-R2-mediated apoptosis was next investigated by analyzing the specific property of this molecule. At least two RNA helicases of the DEAD box protein family have been identified recently that contain a caspase recruitment domain (CARD), The CARD in these RNA helicases functions as a regulator for apoptosis. As DDX3 plays an important role in the regulation of TRAIL-R2-mediated apoptosis, DDX3, a member of the helicases of the DEAD box protein family, can have a CARD as well, and the apoptosis inhibitory function of DDX3 can be directly dependent on the CARD. Thus the possibility that DDX3 is a CARD protein was examined. Amino acid alignment analysis indicates that DDX3 contains a conserved action motif between aa 50-aa 150, as do MDA5 and RIGI. CARD is a homotypic interaction motif. The proteins containing CARD can interact with each other via this domain. As DDX3 is a novel, highly conserved CARD-containing helicase, it is capable of interacting with other CARD proteins. cIAP1, a CARD-containing protein as well, has been widely regarded as an inhibitor of caspase and is recruited to TNFRI and TNFRII to regulate TNFRI mediated apoptosis. Whether DDX3 is able to interact with cIAP1 was tested using anti-DDX3 or anti-TRAIL-R2 antibody in a co-immunoprecipitation experiment. It was determined that cIAP1 can be readily co-immunoprecipitated with DDX3 and with TRAIL-R2 complex analyzed by TRAIL-R2 co-immunoprecipitated and DDX3 co-immunoprecipitated in both TRA-8 untreated parental and resistant cells (FIG. 8H) However, cIAP1 was rapidly released from the TRAIL-R2-DDX3 complex, and this was correlated to DDX3 cleavage in the parent cells. In contrast, cIAP1 level increased at the TRAIL-R2-DDX3 complex in resistant cells after TRA-8 treatment (FIG. 8H). These results indicate that DDX3 could serve as the link between TRAIL-R2 and cIAP1.

Reverse Resistance by Knockdown DDX3.

Figure 9F:
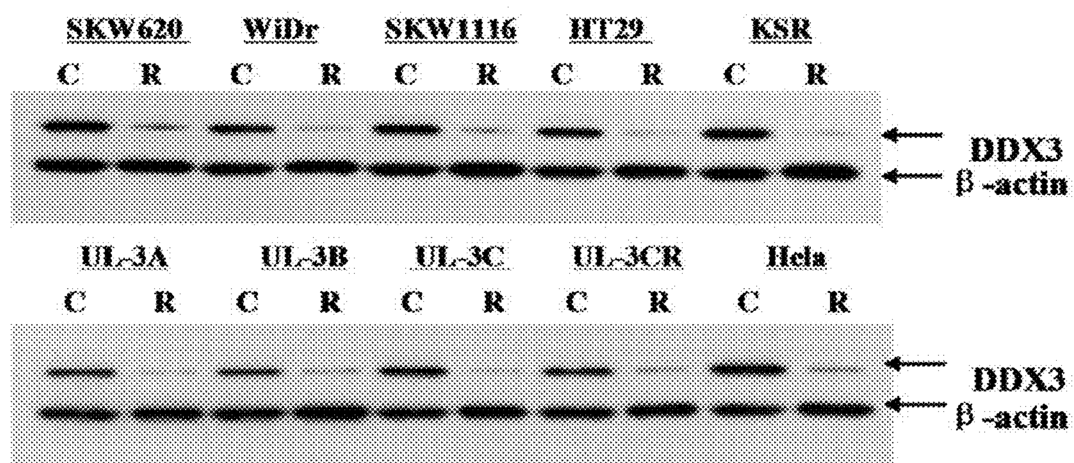
Figure 9G:
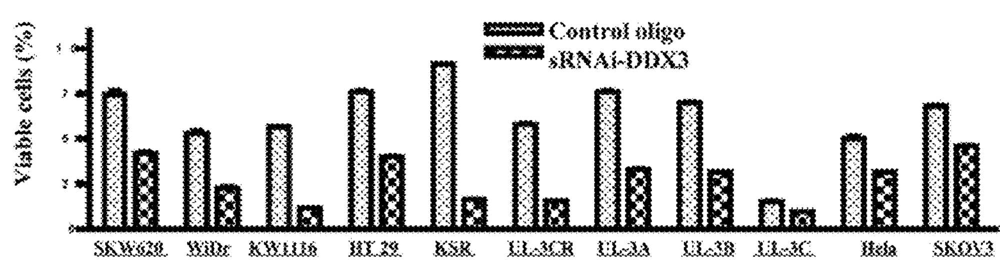

To study the role of DDX3 in TRAIL-R2 signaling, the importance of endogenous DDX3 in TRA8-induced apoptosis was examined. As DDX3 did not decrease in the resistant cells during TRA-8-induced apoptosis, a reduced level of expression of DDX3 can be required for cancer cells to be susceptible to apoptosis. An RNAi strategy was employed to determine the role of DDX3 in the resistance to TRAIL-R2-mediated apoptosis. An online design tool, BLOCK-IT™ RNAi Designer (Invitrogen), was used to identify RNAi targets for DDX3. Five targeted shRNA sequences were selected from the top 10 highest scoring RNAi targets and cloned into the BLOCK-IT™ U6 entry vector. TRA-8-resistant MDA231 cells were transfected with five RNAi constructs, and protein expression levels of DDX3 were determined by Western blot analysis using monoclonal anti-DDX3 antibody 48 hours post-transfection. Four out of five tested RNAi constructs were very effective (over 50% reduction) inhibitors of DDX3 expression compared to nontransfected or GFP-transfected controls (FIGS. 9A-9B). The most effective of these constructs, #2, was selected for analysis of the effect of DDX3 knockdown in TRA-8-mediated apoptosis. To determine whether knockdown DDX3 expression reverses TRA-8 susceptibility in TRA-8-resistant cells, TRA-8-resistant MDA231 cells were co-transfected with an RNAi vector (construct #2) and a GFP expression vector as an indicator of transfected cells. 48 hours after transfection, DDX3 was co-immunoprecipitated with TRAIL-R2 and probed with an anti-DDX3 antibody. As expected, the expression of DDX3 significantly decreased compared to the control cells (FIG. 9C). GFP-positive cells were sorted and cultured with various concentrations of TRA-8 overnight. Using the ATPLITE assay, MDA231 cells transfected with GFP and control vectors did not undergo apoptosis after TRA-8 treatment, indicating that the cells retained resistance to TRA-8. However, cells co-transfected with the DDX3 RNAi and GFP exhibited TRA-8 dose-dependent cell death (FIG. 9D). Using TUNEL staining, a significant number of DDX3 knockdown cells were found to be undergoing apoptosis (FIG. 9E). These results indicate that down-regulation of DDX3 expression reverses TRA-8 resistance. To further determine the causal role of DDX3 in TRAIL-R2-mediated apoptosis, DDX3 expression was reduced in a panel of tumor cells and their susceptibility to TRA-8-induced apoptosis analyzed. DDX3 RNAi reduced the amount of endogenous DDX3 and enhanced the TRA8-induced apoptosis in the panel of tumor cells, including some spontaneous resistant cells (FIGS. 9F-G). In contrast, cells transfected with a control oligonucleotide showed normal DDX3 expression and remained resistant to TRA-8-induced apoptosis (FIGS. 9F-G). Thus, DDX3 is a critical component of the TRAIL-R2 signal transduction apparatus and is essential for resistance to TRAIL-R2-mediated apoptosis.

TRAIL-R2 without DDX3 Binding Region is Pro-Apoptotic.

To test whether, the DDX3 binding motif represents a novel negative regulatory domain modulating to the death domain function of TRAIL-R2, the apoptotic-inducing function of mutant TRAIL-R2 was compared to the wild-type TRAIL-R2. Cells transfected with TRAIL-R2 without death domain appeared to not respond to TRA-8 treatment, but cells transfected with TRAIL-R2 with a truncated DDX3 binding domain appeared pro-apoptotic and exhibited more susceptibility to TRA-8-induced apoptosis compared to wild-type TRAIL-R2-transfected cells (FIG. 10). There was a pronounced inhibitory effect of DDX3 that could suppress TRAIL-R2-mediated apoptosis. These findings indicate that DDX3 is an inhibitory mediator of TRAIL-R2-induced apoptosis.

DDX3 is a CARD Protein Regulating TRAIL-R2-Mediated Apoptosis.

To dissect TRAIL-R2-DDX3-cIAP1 signaling, the region required for its binding to cIAP1 was evaluated. As CARD is at the N terminus of DDX3 and is supposed to interact with cIAP1, this region can be responsible for binding cIAP1. HEK293A cells were transfected with plasmids encoding His-tagged full-length DDX3, DDX3Δ 51-662, DDX3Δ101-662, DDX3Δ151-662, or DDX3Δ1-350. Both full-length and C-terminal deleted DDX3 were able to co-immunoprecipitate cIAP1, the DDX3 with the first 100 aa deleted was unable to co-immunoprecipitate cIAP1 (FIG. 11A-11B). These results confirm that the N-terminal CARD of DDX3 is responsible for recruiting cIAP1 to the TRAIL-R2 complex. It also indicated that the cIAP1 binding motif is located at aa 50-100 of DDX3 in front of the cleavage site, aa 129-135 (DKSDEDD; SEQ ID NO:46). If DDX3 is cleaved during the TRAIL-R2-mediated apoptosis, the N-terminal fragment of DDX3 combination with cIAP1 would be disengaged from the TRAIL-R2 complex, thereby relieving the inhibition of cIAP1 to death signaling. Thus, DDX3 is a candidate for coupling cIAP1 and death receptors to the apoptosis resistance.

To further substantiate this concept, dominant negative mutant DDX3 lacking aa 1-150 was used. This mutant DDX3ΔCARD (DDX3Δ151-662) fails to interact with cIAP1, but is still able to bind to TRAIL-R2 (FIG. 11C). Thus, whether DDX3Δ151-662 could be a dominant negative inhibitor of endogenous DDX3 by competing with wild-type DDX3 binding TRAIL-R2 was assessed. Four type cells were transfected with DDX3ΔCARD. As FIG. 5B shows, DDX3ΔCARD-transfected cells exhibited higher levels of expression of DDX3ΔCARD compared to endogenous, full-length DDX3, suggesting that the truncated DDX3 is able to compete with endogenous DDX3 for TRAIL-R2 binding. As FIG. 11C shows, cIAP1 was co-immunoprecipitated with the full-length DDX3, but not with DDX3ΔCARD, as analyzed by TRAIL-R2-co-IP and Western blotting probed with anti-DDX3 and anti-cIAP1 antibody. Furthermore, the susceptibility of tranfected cells to TRA-8-mediated apoptosis was examined using the ATPLITE assay. Expression of the full-length recombinant DDX3 did not alter the susceptibility to TRA-8-mediated apoptosis as all tested cells remained resistant after TRA-8 treatment. However, TRA-8-resistant tumor cells that expressed high levels of DDX3ΔCARD regained their susceptibility to TRA-8-induced apoptosis after down-regulated TRAIL-R2 associated cIAP1. These data indicate that the inhibition of cIAP1 to TRA-8-induced-apoptosis is mediated by the intact CARD of DDX3. DDX3 lacking the N-terminal CARD may serve as a dominant negative that partially reverses TRA-8 resistance. The potential susceptibility of cancer cells to TRA-8-induced apoptosis could be regulated by the level of DDX3 and cIAP1 on the TRAIL-R2 associated complex.

TRAIL-R2-DDX3-cIAP1 Complex Inhibits Caspase-8 Activation.

DDX3 was quantified to examine how levels of DDX3 present in the cells correlated with caspase-8 recruitment and processing at the TRAIL-R2 DISC. MDA231 and UL-3C parental and resistant cells were treated with TRA-8 for four hours, and TRAIL-R2 was immunoprecipitated with a new anti-TRAIL-R2 monoclonal antibody (clone: 2B4), which recognizes a different TRAIL-R2 epitope than TRA-8. The TRAIL-R2/DDX3/cIAP1 complex was released from the beads, and the TRAIL-R2-associated DDX3 and cIAP1 were subjected to immunoblotting and sandwich ELISA analysis using anti-DDX3 and anti-cIAP1 antibody. ELISA plates were coated with 2B4 anti-TRAIL-R2 antibody to capture the immunoprecipitated TRAIL-R2, and DDX3 and cIAP1 were measured by specific monoclonal antibodies against DDX3 (3E2) and cIAP1. Treatment of either parental-sensitive or induced-resistant tumor cells with TRA-8 did not alter TRAIL-R2 protein levels (FIG. 12A). However, the TRAIL-R2-associated DDX3 levels were significantly altered by TRA-8 treatment in both sensitive and resistant cells. First, untreated resistant cells expressed higher levels of TRAIL-R2-associated DDX3 compared to untreated sensitive cells as detected by 3E2 anti-DDX3 antibody (FIG. 12B). Importantly, after TRA-8 treatment, the TRAIL-R2-associated DDX3 was significantly increased in TRA-8-resistant cells but demonstrated a marked decrease in sensitive cells. The levels of cIAP1 in TRAIL-R2 complex were also altered in the same pattern as DDX3 (FIG. 12C). These results suggest that the CARD domain of DDX3 was released by cleavage from the TRAIL-R2 complex in TRA-8-sensitive cells during apoptosis by the cleavage, whereas DDX3 and cIAP1 indeed were recruited more efficiently to the TRAIL-R2 upon TRA-8 stimulation in resistant cells rather than sensitive cells.

To form functional DISC, it is essential for cancer cells to release cIAP1 from the TRAIL-R2 complex to reduce its suppression to caspase during TRA-8-induced apoptosis. This process requires the cleavage of DDX3, indicating that this step is important to initiating a feed-forward apoptosis amplification loop. Because TRAIL-R2-associated DDX3 resistance to cleavage is correlated with a failure of DISC formation in resistant cells, DDX3 cleavage susceptibility at the TRAIL-R2-DDX3-cIAP1 complex is different between parental and resistant cells. TRAIL-R2-associated DDX3 cleavage potential by different caspases was analyzed in both cells. TRAIL-R2-DDX3-cIAP1 complex was co-immunoprecipitated with anti-TRAIL-R2 antibody. The eluted fraction from the beads was incubated with active caspase-2 and -8. The cleavage of DDX3 was detected by the Western analysis with anti-DDX3 antibody. These results in combination with ELISA analysis (FIG. 12E) demonstrated that DDX3 cleavage by caspase-8 in resistant cells was highly attenuated compared to sensitive cells, although caspase-2 exhibited similar protease potential in both cells (FIG. 12E). These results indicate that there is a functional difference in the DDX3 complex between TRA-8-sensitive and -resistant cells. It also indicates that the failure of cleavage of DDX3 by death receptor-associated initial caspases is a key step in the development of TRA-8 resistance.

As cleavage of DDX3 was inhibited in the induced resistant cells, it promoted a study to determine the step in apoptosis signaling in which DDX3 inhibits TRAIL-R2-mediated apoptosis. The DDX3/cIAP1 complex was predicted to inhibit caspase-8 activation; therefore, the activation of caspase-8 at the TRAIL-R2-DDX3-cIAP1 complex as one of the first detectable events after receptor triggering was examined. To assess the effect of the TRAIL-R2-DDX3-cIAP1 complex on caspase-8 activation, the caspase activity was measured using the fluorofenic substrate, Ac-IETD-AMC, incubated with active caspase-8 and DDX3 co-IP eluted fractions from parental sensitive or induced resistant cells. A dose-dependent inhibition of caspase-8 activity was observed over a wide range of dilutions in the TRAIL-R2 co-IP eluted fraction from resistant cells compared to sensitive cells. In addition, purified cIAP1 also suppressed caspase-8 protease activity completely (FIG. 12F). It is plausible that DDX3-associated cIAP1 is an inhibitor in the initial activation of caspase-8, thereby preventing the cleavage of DDX3. Thus, these data provided direct evidence that DDX3-cIAP1 can regulate caspase-8 activity and indicates that DDX3-cIAP1 is a specific regulator of caspase-8 engaged by TRAIL-R2.

The effect of TRAIL-R2-DDX3-cIAP1 on caspase-8 activation was examined by direct analyses of cIAP1-inhibited caspase-8 in combination with cleavage of DDX3 by caspase assay, and showed that DDX3-cIAP1 also functions as a novel type of caspase inhibitor. The DDX3-cIAP1 complex is capable of arresting death receptor pro-apoptotic signals by suppressing the activation of caspase-8, thereby inhibiting the cleavage of TRAIL-R2-associated DDX3 by the initial caspase. This model shows that DDX3 protects cells against TRA-8-induced apoptosis via the recruitment of cIAP1 and contributes to the blockage of the death signaling pathways in cancer cells.

Example 3

Regulation of DDX3 Binding to DR5 by Serine Phosphorylation at a N-Terminal Region Bioinformatics search led to identification of a serine-rich domain in DDX3 (SEQ ID NO:20, corresponding to amino acids 70 to 90 of SEQ ID NO:26) that is conserved for a potential substrate of GSK3 (FIG. 13A). Compared with β-Catenin and glycogen synthetase which are two best substrates of GSK-3, DDX3 has five sequential serines N-terminal to the primed site. There are several lines of evidence supporting that DDX3 is a substrate for GSK3: (1) DDX3 is directly associated with GSK3α as demonstrated by co-immunoprecipitation of DDX3 with GSK3α and GSK3 is able to phosphorylate DDX3 (FIGS. 13B-13C); (2) GSK3 fails to phosphorylate DDX3 with a point mutation at Ser90 (FIG. 13D). (3) The Ser90 mutant DDX3 exhibits increased disassociation from DR5 and cleavage during TRA-8-mediated apoptosis (FIGS. 13E-F). These results show that the serine-rich domain at the N-terminal of DDX3 plays a regulatory role in DDX3 association with DR5.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Throughout the description and claims of this specification, the word “comprise” and variations of the word, such as “comprising” and “comprises,” means “including but not limited to,” and is not intended to exclude, for example, other additives, components, integers or steps.

Those skilled in the art will recognize, or be able to ascertain using no more than routine experimentation, many equivalents to the specific embodiments of the method and compositions described herein. Such equivalents are intended to be encompassed by the appended claims.

REFERENCES

Akao, Y., Yoshida, H., Matsumoto, K., Matsui, T., Hogetu, K., Tanaka, N., and Usukura, J. (2003). A tumour-associated DEAD-box protein, rck/p54 exhibits RNA unwinding activity toward c-myc RNAs in vitro. Genes Cells 8, 671-676.

Alnemri, E. S., D. J. Livingston, D. W. Nicholson, G. Salvesen, N. A. Thornberry, W. W. Wong, and J. Yuan. 1996. Human ICE/CED-3 protease nomenclature. Cell 87:171.

Andrejeva, J., Childs, K. S., Young, D. F., Carlos, T. S., Stock, N., Goodbourn, S., and Randall, R. E. (2004). The V proteins of paramyxoviruses bind the IFN-inducible RNA helicase, mda-5, and inhibit its activation of the IFN-beta promoter. Proc Natl Acad Sci USA 101, 17264-17269.

Ashhab, Y., A. Alian, A. Polliack, A. Panet, and D. Ben Yehuda. 2001. Two splicing variants of a new inhibitor of apoptosis gene with different biological properties and tissue distribution pattern. FEBS Lett 495:56-60.

Ashkenazi, A, Pai, R C, Fong, S, Leung, S, Lawrence, D A, Marsters, S A, Blackie, C, Chang, L, McMurtrey, A E, Hebert, A, DeForge, L, Koumenis, I L, Lewis, D, Harris, L, Bussiere, J, Koeppen, H, Shahrokh, Z, and Schwall, R H Safety and antitumor activity of recombinant soluble Apo2 ligand. J Clin Invest 1999; 104: 155-162.

Baldwin, A. S. 2001. Control of oncogenesis and cancer therapy resistance by the transcription factor NF-kappaB. J Clin Invest 107:241-246.

Baldwin, A. S., Jr. 1996. The NF-kappa B and I kappa B proteins: new discoveries and insights. Annu Rev Immunol 14:649-683.

Belka, C., B. Schmid, P. Marini, E. Durand, J. Rudner, H. Faltin, M. Bamberg, K. Schulze-Osthoff, and W. Budach. 2001. Sensitization of resistant lymphoma cells to irradiation-induced apoptosis by the death ligand TRAIL. Oncogene 20:2190-2196.

Bockbrader, K. M., Tan, M., and Sun, Y. (2005). A small molecule Smac-mimic compound induces apoptosis and sensitizes TRAIL- and etoposide-induced apoptosis in breast cancer cells. Oncogene.

Bodmer, J. L., N. Holler, S. Reynard, P. Vinciguerra, P. Schneider, P. Juo, J. Blenis, and J. Tschopp. 2000. TRAIL receptor-2 signals apoptosis through FADD and caspase-8. Nat Cell Biol 2:241-243.

Boldin, M. P., E. E. Varfolomeev, Z. Pancer, I. L. Mett, J. H. Camonis, and D. Wallach. 1995. A novel protein that interacts with the death domain of Fas/APO1 contains a sequence motif related to the death domain. J Biol Chem 270:7795-7798.

Boldin, M. P., T. M. Goncharov, Y. V. Goltsev, and D. Wallach. 1996. Involvement of MACH, a novel MORT1/FADD-interacting protease, in Fas/APO-1- and TNF receptor-induced cell death. Cell 85:803-815.

Bonavida, B, Ng, C P, Jazirehi, A, Schiller, G, and Mizutani, Y Selectivity of TRAIL-mediated apoptosis of cancer cells and synergy with drugs: the trail to non-toxic cancer therapeutics (review). Int J Oncol 1999; 15: 793-802.

Buchsbaum, D. J., Zhou, T., Grizzle, W. E., Oliver, P. G., Hammond, C. J., Zhang, S., Carpenter, M., and LoBuglio, A. F. (2003). Antitumor efficacy of TRA-8 anti-DR5 monoclonal antibody alone or in combination with chemotherapy and/or radiation therapy in a human breast cancer model. Clin Cancer Res 9, 3731-3741.

Budihardjo, I., H. Oliver, M. Lutter, X. Luo, and X. Wang. 1999. Biochemical pathways of caspase activation during apoptosis. Annu Rev Cell Dev Biol 15:269-290.

Carthy, C M, Yanagawa, B, Luo, H, Granville, D J, Yang, D, Cheung, P, Cheung, C, Esfandiarei, M, Rudin, C M, Thompson, C B, Hunt, D W, and McManus, B M Bcl-2 and Bcl-xL overexpression inhibits cytochrome c release, activation of multiple caspases, and virus release following coxsackievirus B3 infection. Virology 2003; 313: 147-157

Causevic, M., R. G. Hislop, N. M. Kernohan, F. A. Carey, R. A. Kay, R. J. Steele, and F. V. Fuller-Pace. 2001. Overexpression and poly-ubiquitylation of the DEAD-box RNA helicase p68 in colorectal tumours. Oncogene 20:7734-7743.

Chang, H. Y., H. Nishitoh, X. Yang, H. Ichijo, and D. Baltimore. 1998. Activation of apoptosis signal-regulating kinase 1 (ASK1) by the adapter protein Daxx. Science 281:1860-1863.

Chaudhary, P. M., M. Eby, A. Jasmin, A. Bookwalter, J. Murray, and L. Hood. 1997. Death receptor 5, a new member of the TNFR family, and DR4 induce FADD-dependent apoptosis and activate the NF-kappaB pathway. Immunity 7:821-830.

Chawla-Sarkar, M, Bae, S I, Reu, F J, Jacobs, B S, Lindner, D J, and Borden, E C Downregulation of Bcl-2, FLIP or IAPs (XIAP and survivin) by siRNAs sensitizes resistant melanoma cells to Apo2L/TRAIL-induced apoptosis. Cell Death Differ 2004; 11: 915-923

Chen, C., L. C. Edelstein, and C. Gelinas. 2000. The Rel/NF-kappaB family directly activates expression of the apoptosis inhibitor Bcl-x(L). Mol Cell Biol 20:2687-2695.

Chinnaiyan, A. M., K. O'Rourke, M. Tewari, and V. M. Dixit. 1995. FADD, a novel death domain-containing protein, interacts with the death domain of Fas and initiates apoptosis. Cell 81:505-512.

Chinnaiyan, A M, Prasad, U, Shankar, S, Hamstra, D A, Shanaiah, M, Chenevert, T L, Ross, B D, and Rehemtulla, A Combined effect of tumor necrosis factor-related apoptosis-inducing ligand and ionizing radiation in breast cancer therapy. Proc Natl Acad Sci USA 2000; 97: 1754-1759.

Crook, N. E., R. J. Clem, and L. K. Miller. 1993. An apoptosis-inhibiting baculovirus gene with a zinc finger-like motif. J Virol 67:2168-2174.

Cuello, M, Ettenberg, S A, Nau, M M, and Lipkowitz, S Synergistic induction of apoptosis by the combination of trail and chemotherapy in chemoresistant ovarian cancer cells. Gynecol Oncol 2001; 81: 380-390.

Cummins, J M, Kohli, M, Rago, C, Kinzler, K W, Vogelstein, B, and Bunz, F X-linked inhibitor of apoptosis protein (XIAP) is a nonredundant modulator of tumor necrosis factor-related apoptosis-inducing ligand (TRAIL)-mediated apoptosis in human cancer cells. Cancer Res 2004; 64: 3006-3008

Damiano, J. S., and J. C. Reed. 2004. CARD proteins as therapeutic targets in cancer. Curr Drug Targets 5:367-374.

Degli-Esposti, M. A., W. C. Dougall, P. J. Smolak, J. Y. Waugh, C. A. Smith, and R. G. Goodwin. 1997. The novel receptor TRAIL-R4 induces NF-kappaB and protects against TRAIL-mediated apoptosis, yet retains an incomplete death domain. Immunity 7:813-820.

Desagher, S., and J. C. Martinou. 2000. Mitochondria as the central control point of apoptosis. Trends Cell Biol 10:369-377.

Deveraux, Q. L., Roy, N., Stennicke, H. R., Van Arsdale, T., Zhou, Q., Srinivasula, S. M., Alnemri, E. S., Salvesen, G. S., and Reed, J. C. (1998). IAPs block apoptotic events induced by caspase-8 and cytochrome c by direct inhibition of distinct caspases. Embo J 17, 2215-2223.

Deveraux, Q. L., and J. C. Reed. 1999. IAP family proteins—suppressors of apoptosis. Genes Dev 13:239-252.

Deveraux, Q. L., R. Takahashi, G. S. Salvesen, and J. C. Reed. 1997. X-linked IAP is a direct inhibitor of cell-death proteases. Nature 388:300-304.

Dubey, P., Hendrickson, R. C., Meredith, S. C., Siegel, C. T., Shabanowitz, J., Skipper, J. C., Engelhard, V. H., Hunt, D. F., and Schreiber, H. (1997). The immunodominant antigen of an ultraviolet-induced regressor tumor is generated by a somatic point mutation in the DEAD box helicase p68. J Exp Med 185, 695-705.

Emery, J G, McDonnell, P, Burke, M B, Deen, K C, Lyn, S, Silverman, C, Dul, E, Appelbaum, E R, Eichman, C, DiPrinzio, R, Dodds, R A, James, I E, Rosenberg, M, Lee, J C, and Young, PR Osteoprotegerin is a receptor for the cytotoxic ligand TRAIL. J Biol Chem 1998; 273: 14363-14367.

Fesik, S. W. 2000. Insights into programmed cell death through structural biology. Cell 103:273-282.

Fu, J. J., L. Y. Li, and G. X. Lu. 2002. Molecular cloning and characterization of human DDX36 and mouse Ddx36 genes, new members of the DEAD/H box superfamily. Sheng Wu Hua Xue Yu Sheng Wu Wu Li Xue Bao (Shanghai) 34:655-661.

Fulda, S, Meyer, E, and Debatin, K M Inhibition of TRAIL-induced apoptosis by Bcl-2 overexpression. Oncogene 2002; 21: 2283-2294

Fulda, S., E. Meyer, C. Friesen, S. A. Susin, G. Kroemer, and K. M. Debatin. 2001. Cell type specific involvement of death receptor and mitochondrial pathways in drug-induced apoptosis. Oncogene 20:1063-1075.

George, R. E., R. M. Kenyon, A. G. McGuckin, A. J. Malcolm, A. D. Pearson, and J. Lunec. 1996. Investigation of co-amplification of the candidate genes ornithine decarboxylase, ribonucleotide reductase, syndecan-1 and a DEAD box gene, DDX1, with N-myc in neuroblastoma. United Kingdom Children's Cancer Study Group. Oncogene 12:1583-1587.

Gliniak, B and Le, T Tumor necrosis factor-related apoptosis-inducing ligand's antitumor activity in vivo is enhanced by the chemotherapeutic agent CPT-11. Cancer Res 1999; 59: 6153-6158.

Godbout, R., M. Packer, and W. Bie. 1998. Overexpression of a DEAD box protein (DDX1) in neuroblastoma and retinoblastoma cell lines. J Biol Chem 273:21161-21168.

Green, A. M., and N. D. Steinmetz. 2002. Monitoring apoptosis in real time. Cancer J 8:82-92.

Green, D. R. 1998. Apoptotic pathways: the roads to ruin. Cell 94:695-698.

Green, D. R. 2000. Apoptotic pathways: paper wraps stone blunts scissors. Cell 102:1-4.

Griffith, T S, Rauch, C T, Smolak, P J, Waugh, J Y, Boiani, N, Lynch, D H, Smith, C A, Goodwin, R G, and Kubin, M Z Functional analysis of TRAIL receptors using monoclonal antibodies. J Immunol 1999; 162: 2597-2605.

Grimm, S., B. Z. Stanger, and P. Leder. 1996. RIP and FADD: two "death domain"-containing proteins can induce apoptosis by convergent, but dissociable, pathways. Proc Natl Acad Sci USA 93:10923-10927.

Hashimoto, K., Y. Nakagawa, H. Morikawa, M. Niki, Y. Egashira, I. Hirata, K. Katsu, and Y. Akao. 2001. Co-overexpression of DEAD box protein rck/p54 and c-myc protein in human colorectal adenomas and the relevance of their expression in cultured cell lines. Carcinogenesis 22:1965-1970.

Heim, M. H. (2005). RIG-I: an essential regulator of virus-induced interferon production. J Hepatol 42, 431-433.

Heinlein, U. A. 1998. Dead box for the living. J Pathol 184:345-347.

Hernandez, A., Q. D. Wang, S. A. Schwartz, and B. M. Evers. 2001. Sensitization of human colon cancer cells to TRAIL-mediated apoptosis. J Gastrointest Surg 5:56-65.

Hinz, S, Trauzold, A, Boenicke, L, Sandberg, C, Beckmann, S, Bayer, E, Walczak, H, Kalthoff, H, and Ungefroren, H Bcl-XL protects pancreatic adenocarcinoma cells against CD95- and TRAIL-receptor-mediated apoptosis. Oncogene 2000; 19: 5477-5486

Ichijo, H. 1998. [Molecular mechanisms for cell life and cell death]. Kokubyo Gakkai Zasshi 65:155-163.

Ichijo, H., E. Nishida, K. Irie, P. ten Dijke, M. Saitoh, T. Moriguchi, M. Takagi, K. Matsumoto, K. Miyazono, and Y. Gotoh. 1997. Induction of apoptosis by ASK1, a mammalian MAPKKK that activates SAPK/JNK and p38 signaling pathways. Science 275:90-94.

Ichikawa, K., W. Liu, L. Zhao, Z. Wang, D. Liu, T. Ohtsuka, H. Zhang, J. D. Mountz, W. J. Koopman, R. P. Kimberly, and T. Zhou. 2001. Tumoricidal activity of a novel anti-human DR5 monoclonal antibody without hepatocyte cytotoxicity. Nat Med 7:954-960.

Ichikawa, K., W. Liu, M. Fleck, H. Zhang, L. Zhao, T. Ohtsuka, Z. Wang, D. Liu, J. D. Mountz, M. Ohtsuki, W. J. Koopman, R. Kimberly, and T. Zhou. 2003. TRAIL-R2 (DR5) mediates apoptosis of synovial fibroblasts in rheumatoid arthritis J Immunol 171:1061-1069.

Ip, Y. T., and R. J. Davis. 1998. Signal transduction by the c-Jun N-terminal kinase (JNK)—from inflammation to development. Curr Opin Cell Biol 10:205-219.

Irmler, M., M. Thome, M. Hahne, P. Schneider, K. Hofmann, V. Steiner, J. L. Bodmer, M. Schroter, K. Burns, C. Mattmann, D. Rimoldi, L. E. French, and J. Tschopp. 1997. Inhibition of death receptor signals by cellular FLIP. Nature 388:190-195.

Jo, M., T. H. Kim, D. W. Seol, J. E. Esplen, K. Dorko, T. R. Billiar, and S. C. Strom. 2000. Apoptosis induced in normal human hepatocytes by tumor necrosis factor-related apoptosis-inducing ligand. Nat Med 6:564-567.

Kang, D. C., R. V. Gopalkrishnan, L. Lin, A. Randolph, K. Valerie, S. Pestka, and P. B. Fisher. 2004. Expression analysis and genomic characterization of human melanoma differentiation associated gene-5, mda-5: a novel type I interferon-responsive apoptosis-inducing gene. Oncogene 23:1789-1800.

Kang, D. C., R. V. Gopalkrishnan, Q. Wu, E. Jankowsky, A. M. Pyle, and P. B. Fisher. 2002. mda-5: An interferon-inducible putative RNA helicase with double-stranded RNA-dependent ATPase activity and melanoma growth-suppressive properties. Proc Natl Acad Sci USA 99:637-642.

Kasof, G. M., and B. C. Gomes. 2001. Livin, a novel inhibitor of apoptosis protein family member. J Biol Chem 276:3238-3246.

Kawai, T., Takahashi, K., Sato, S., Coban, C., Kumar, H., Kato, H., Ishii, K. J., Takeuchi, O., and Akira, S. (2005). IPS-1, an adaptor triggering RIG-I- and Mda5-mediated type I interferon induction. Nat Immunol 6, 981-988.

Keane, M M, Ettenberg, S A, Nau, M M, Russell, E K, and Lipkowitz, S Chemotherapy augments TRAIL-induced apoptosis in breast cell lines. Cancer Res 1999; 59: 734-741.

Kischkel, F. C., D. A. Lawrence, A. Chuntharapai, P. Schow, K. J. Kim, and A. Ashkenazi. 2000. Apo2L/TRAIL-dependent recruitment of endogenous FADD and caspase-8 to death receptors 4 and 5. Immunity 12:611-620.

Kischkel, F. C., D. A. Lawrence, A. Tinel, H. LeBlanc, A. Virmani, P. Schow, A. Gazdar, J. Blenis, D. Arnott, and A. Ashkenazi. 2001. Death receptor recruitment of endogenous caspase-10 and apoptosis initiation in the absence of caspase-8. J Biol Chem 276:46639-46646.

Krammer, P. H. 2000. CD95's deadly mission in the immune system. Nature 407:789-795.

Krueger, A., I. Schmitz, S. Baumann, P. H. Krammer, and S. Kirchhoff. 2001. Cellular FLICE-inhibitory protein splice variants inhibit different steps of caspase-8 activation at the CD95 death-inducing signaling complex. J Biol Chem 276:20633-20640.

Krueger, A., S. Baumann, P. H. Krammer, and S. Kirchhoff. 2001. FLICE-inhibitory proteins: regulators of death receptor-mediated apoptosis. Mol Cell Biol 21:8247-8254.

Kuang, A. A., G. E. Diehl, J. Zhang, and A. Winoto. 2000. FADD is required for DR4- and DR5-mediated apoptosis: lack of trail-induced apoptosis in FADD-deficient mouse embryonic fibroblasts. J Biol Chem 275:25065-25068.

Lassus, P., X. Opitz-Araya, and Y. Lazebnik. 2002. Requirement for caspase-2 in stress-induced apoptosis before mitochondrial permeabilization. Science 297:1352-1354.

Lawrence, D., Z. Shahrokh, S. Marsters, K. Achilles, D. Shih, B. Mounho, K. Hillan, K. Totpal, L. DeForge, P. Schow, J. Hooley, S. Sherwood, R. Pai, S. Leung, L. Khan, B. Gliniak, J. Bussiere, C. A. Smith, S. S. Strom, S. Kelley, J. A. Fox, D. Thomas, and A. Ashkenazi. 2001. Differential hepatocyte toxicity of recombinant Apo2L/TRAIL versions. Nat Med 7:383-385.

LeBlanc, H, Lawrence, D, Varfolomeev, E, Totpal, K, Morlan, J, Schow, P, Fong, S, Schwall, R, Sinicropi, D, and Ashkenazi, A Tumor-cell resistance to death receptor-induced apoptosis through mutational inactivation of the proapoptotic Bcl-2 homolog Bax. Nat. Med 2002; 8: 274-281.

Li, L., Thomas, R. M., Suzuki, H., De Brabander, J. K., Wang, X., and Harran, P. G. (2004). A small molecule Smac mimic potentiates TRAIL- and TNFalpha-mediated cell death. Science 305, 1471-1474.

Lin, Y., A. Devin, A. Cook, M. M. Keane, M. Kelliher, S. Lipkowitz, and Z. G. Liu. 2000. The death domain kinase RIP is essential for TRAIL (Apo2L)-induced activation of IkappaB kinase and c-Jun N-terminal kinase. Mol Cell Biol 20:6638-6645.

MacFarlane, M., M. Ahmad, S. M. Srinivasula, T. Fernandes-Alnemri, G. M. Cohen, and E. S. Alnemri. 1997. Identification and molecular cloning of two novel receptors for the cytotoxic ligand TRAIL. J Biol Chem 272: 25417-25420.

Marsters, S. A., J. P. Sheridan, R. M. Pitti, A. Huang, M. Skubatch, D. Baldwin, J. Yuan, A. Gurney, A. D. Goddard, P. Godowski, and A. Ashkenazi. 1997. A novel receptor for Apo2L/TRAIL contains a truncated death domain. Curr Biol 7:1003-1006.

Matsuzaki, H, Schmied, B M, Ulrich, A, Standop, J, Schneider, M B, Batra, S K, Picha, K S, and Pour, P M Combination of tumor necrosis factor-related apoptosis-inducing ligand (TRAIL) and actinomycin D induces apoptosis even in TRAIL-resistant human pancreatic cancer cells. Clin Cancer Res 2001; 7: 407-414.

McCarthy, J. V., J. Ni, and V. M. Dixit. 1998. RIP2 is a novel NF-kappaB-activating and cell death-inducing kinase. J Biol Chem 273:16968-16975.

Mitsiades, C. S., S. P. Treon, N. Mitsiades, Y. Shima, P. Richardson, R. Schlossman, T. Hideshima, and K. C. Anderson. 2001. TRAIL/Apo2L ligand selectively induces apoptosis and overcomes drug resistance in multiple myeloma: therapeutic applications. Blood 98:795-804.

Mitsiades, N., C. S. Mitsiades, V. Poulaki, K. C. Anderson, and S. P. Treon. 2002. Intracellular regulation of tumor necrosis factor-related apoptosis-inducing ligand-induced apoptosis in human multiple myeloma cells. Blood 99:2162-2171.

Muzio, M., A. M. Chinnaiyan, F. C. Kischkel, K. O'Rourke, A. Shevchenko, J. Ni, C. Scaffidi, J. D. Bretz, M. Zhang, R. Gentz, M. Mann, P. H. Krammer, M. E. Peter, and V. M. Dixit. 1996. FLICE, a novel FADD-homologous ICE/CED-3-like protease, is recruited to the CD95 (Fas/APO-1) death-inducing signaling complex. Cell 85:817-827.

Nagata, S. 1997. Apoptosis by death factor. Cell 88:355-365.

Ng, C P and Bonavida, B X-linked inhibitor of apoptosis (XIAP) blocks Apo2 ligand/tumor necrosis factor-related apoptosis-inducing ligand-mediated apoptosis of prostate cancer cells in the presence of mitochondrial activation: sensitization by overexpression of second mitochondria-derived activator of caspase/direct IAP-binding protein with low pl (Smac/DIABLO). Mol Cancer Ther 2002; 1: 1051-1058

Nicholson, D. W. (2000). From bench to clinic with apoptosis-based therapeutic agents. Nature 407, 810-816.

Nishitoh, H., M. Saitoh, Y. Mochida, K. Takeda, H. Nakano, M. Rothe, K. Miyazono, and H. Ichijo. 1998. ASK1 is essential for JNK/SAPK activation by TRAF2. Mol Cell 2:389-395.

Ohtsuka, T., and T. Zhou. 2002. Bisindolylmaleimide VIII enhances DR5-mediated apoptosis through the MKK4/JNK/p38 kinase and the mitochondrial pathways. J Biol Chem 277:29294-29303.

Ohtsuka, T., D. Buchsbaum, P. Oliver, S. Makhija, R. Kimberly, and T. Zhou. 2003. Synergistic induction of tumor cell apoptosis by death receptor antibody and chemotherapy agent through JNK/p38 and mitochondrial death pathway. Oncogene 22:2034-2044.

Owsianka, A. M., and A. H. Patel. 1999. Hepatitis C virus core protein interacts with a human DEAD box protein DDX3. Virology 257:330-340.

Pan, G., J. Ni, Y. F. Wei, G. Yu, R. Gentz, and V. M. Dixit. 1997. An antagonist decoy receptor and a death domain-containing receptor for TRAIL. Science 277:815-818.

Pan, G., O'Rourke, K., Chinnaiyan, A. M., Gentz, R., Ebner, R., Ni, J., and Dixit, V. M. (1997). The receptor for the cytotoxic ligand TRAIL. Science 276, 111-113.

Park, S Y, Billiar, T R, and Seol, D W IFN-gamma inhibition of TRAIL-induced IAP-2 upregulation, a possible mechanism of IFN-gamma-enhanced TRAIL-induced apoptosis. Biochem Biophys Res Commun 2002; 291: 233-236

Payan, and Y. Luo. 1999. Identification of RIP3, a RIP-like kinase that activates apoptosis and NFkappaB. Curr Biol 9:539-542.

Pitti, R. M., Marsters, S. A., Ruppert, S., Donahue, C. J., Moore, A., and Ashkenazi, A. (1996). Induction of apoptosis by Apo-2 ligand, a new member of the tumor necrosis factor cytokine family. J Biol Chem 271, 12687-12690.

Roa, W H, Chen, H, Fulton, D, Gulavita, S, Shaw, A, Th'ng, J, Farr-Jones, M, Moore, R, and Petruk, K X-linked inhibitor regulating TRAIL-induced apoptosis in chemoresistant human primary glioblastoma cells. Clin Invest Med 2003; 26: 231-242

Rokhlin, O W, Guseva, N, Tagiyev, A, Knudson, C M, and Cohen, M B Bcl-2 oncoprotein protects the human prostatic carcinoma cell line PC3 from TRAIL-mediated apoptosis. Oncogene 2001; 20: 2836-2843

Saleh, A., S. M. Srinivasula, S. Acharya, R. Fishel, and E. S. Alnemri. 1999. Cytochrome c and dATP-mediated oligomerization of Apaf-1 is a prerequisite for procaspase-9 activation. J Biol Chem 274:17941-17945.

Scaffidi, C., S. Fulda, A. Srinivasan, C. Friesen, F. Li, K. J. Tomaselli, K. M. Debatin, P. H. Krammer, and M. E. Peter. 1998. Two CD95 (APO-1/Fas) signaling pathways. Embo J 17:1675-1687.

Schneider, P., J. L. Bodmer, M. Thome, K. Hofmann, N. Holler, and J. Tschopp. 1997. Characterization of two receptors for TRAIL. FEBS Lett 416:329-334.

Schneider, P., M. Thome, K. Burns, J. L. Bodmer, K. Hofmann, T. Kataoka, N. Holler, and J. Tschopp. 1997. TRAIL receptors 1 (DR4) and 2 (DR5) signal FADD-dependent apoptosis and activate NF-kappaB. Immunity 7:831-836.

Sheridan, J. P., S. A. Marsters, R. M. Pitti, A. Gurney, M. Skubatch, D. Baldwin, L. Ramakrishnan, C. L. Gray, K. Baker, W. I. Wood, A. D. Goddard, P. Godowski, and A. Ashkenazi. 1997. Control of TRAIL-induced apoptosis by a family of signaling and decoy receptors. Science 277:818-821.

Sinicrope, F A, Penington, R C, and Tang, X M Tumor necrosis factor-related apoptosis-inducing ligand-induced apoptosis is inhibited by Bcl-2 but restored by the small molecule Bcl-2 inhibitor, HA 14-1, in human colon cancer cells. Clin Cancer Res 2004; 10: 8284-8292

Sprick, M. R., M. A. Weigand, E. Rieser, C. T. Rauch, P. Juo, J. Blenis, P. H. Krammer, and H. Walczak. 2000. FADD/MORT1 and caspase-8 are recruited to TRAIL receptors 1 and 2 and are essential for apoptosis mediated by TRAIL receptor 2. Immunity 12:599-609.

Stanger, B. Z., P. Leder, T. H. Lee, E. Kim, and B. Seed. 1995. RIP: a novel protein containing a death domain that interacts with Fas/APO-1 (CD95) in yeast and causes cell death. Cell 81:513-523.

Sun, S Y, Yue, P, Hong, W K, and Lotan, R Augmentation of tumor necrosis factor-related apoptosis-inducing ligand (TRAIL)-induced apoptosis by the synthetic retinoid 6-[3-(1-adamantyl)-4-hydroxyphenyl]-2-naphthalene carboxylic acid (CD437) through up-regulation of TRAIL receptors in human lung cancer cells. Cancer Res 2000; 60: 7149-7155.

Suzuki, Y., Y. Nakabayashi, K. Nakata, J. C. Reed, and R. Takahashi. 2001. X-linked inhibitor of apoptosis protein (XIAP) inhibits caspase-3 and -7 in distinct modes. J Biol Chem 276:27058-27063.

Ting, A. T., F. X. Pimentel-Muinos, and B. Seed. 1996. RIP mediates tumor necrosis factor receptor 1 activation of NF-kappaB but not Fas/APO-1-initiated apoptosis. Embo J 15:6189-6196.

Toshiaki Ohtsuka, Buchsbaum D, Patsy Oliver, Sharmila Makhija, Robert Kimberly, and Tong Zhou Synergistic Induction of Tumor Cell Apoptosis by Death Receptor Antibody and Chemotherapy Agent Through JNK/p38 and Mitochondrial Death Pathway. Onogene 2003; in press:

Tournier, C., P. Hess, D. D. Yang, J. Xu, T. K. Turner, A. Nimnual, D. Bar-Sagi, S. N. Jones, R. A. Flavell, and R. J. Davis. 2000. Requirement of JNK for stress-induced activation of the cytochrome c-mediated death pathway. Science 288:870-874.

Vucic, D., H. R. Stennicke, M. T. Pisabarro, G. S. Salvesen, and V. M. Dixit. 2000. ML-IAP, a novel inhibitor of apoptosis that is preferentially expressed in human melanomas. Curr Biol 10:1359-1366.

Wagner, K W, Engels, I H, and Deveraux, Q L Caspase-2 can function upstream of bid cleavage in the TRAIL apoptosis pathway. J Biol Chem 2004; 279: 35047-35052

Walczak, H, Miller, R E, Ariail, K, Gliniak, B, Griffith, T S, Kubin, M, Chin, W, Jones, J, Woodward, A, Le, T, Smith, C, Smolak, P, Goodwin, R G, Rauch, C T, Schuh, J C, and Lynch, D H Tumoricidal activity of tumor necrosis factor-related apoptosis-inducing ligand in vivo. Nat Med 1999; 5: 157-163.

Walczak, H., Degli-Esposti, M. A., Johnson, R. S., Smolak, P. J., Waugh, J. Y., Boiani, N., Timour, M. S., Gerhart, M. J., Schooley, K. A., Smith, C. A., et al. (1997). TRAIL-R2: a novel apoptosis-mediating receptor for TRAIL. Embo J 16, 5386-5397.

Walczak, H., M. A. Degli-Esposti, R. S. Johnson, P. J. Smolak, J. Y. Waugh, N. Boiani, M. S. Timour, M. J. Gerhart, K. A. Schooley, C. A. Smith, R. G. Goodwin, and C. T. Rauch. 1997. TRAIL-R2: a novel apoptosis-mediating receptor for TRAIL. Embo J 16:5386-5397.

Wang, C. Y., D. C. Guttridge, M. W. Mayo, and A. S. Baldwin, Jr. 1999. NF-kappaB induces expression of the Bcl-2 homologue A1/Bfl-1 to preferentially suppress chemotherapy-induced apoptosis. Mol Cell Biol 19:5923-5929.

Wieland, I., Ropke, A., Stumm, M., Sell, C., Weidle, U. H., and Wieacker, P. F. (2000). Molecular characterization of the DICE1 (DDX26) tumor suppressor gene in lung carcinoma cells. Oncol Res 12, 491-500.

Wiley, S. R., K. Schooley, P. J. Smolak, W. S. Din, C. P. Huang, J. K. Nicholl, G. R. Sutherland, T. D. Smith, C. Rauch, C. A. Smith, and et al. 1995. Identification and characterization of a new member of the TNF family that induces apoptosis. Immunity 3:673-682.

Yamanaka, T., K. Shiraki, K. Sugimoto, T. Ito, K. Fujikawa, M. Ito, K. Takase, M. Moriyama, T. Nakano, and A. Suzuki. 2000. Chemotherapeutic agents augment TRAIL-induced apoptosis in human hepatocellular carcinoma cell lines. Hepatology 32:482-490.

Yang, X., R. Khosravi-Far, H. Y. Chang, and D. Baltimore. 1997. Daxx, a novel Fas-binding protein that activates JNK and apoptosis. Cell 89:1067-1076.

Yang, Y. L., and Li, X. M. (2000). The IAP family: endogenous caspase inhibitors with multiple biological activities. Cell Res 10, 169-177.

Yedavalli, V. S., Neuveut, C., Chi, Y. H., Kleiman, L., and Jeang, K. T. (2004). Requirement of DDX3 DEAD box RNA helicase for HIV-1 Rev-RRE export function. Cell 119, 381-392.

Yoneyama, M., and Fujita, T. (2004). [RIG-I: critical regulator for virus-induced innate immunity]. Tanpakushitsu Kakusan Koso 49, 2571-2578.

Yoneyama, M., Kikuchi, M., Matsumoto, K., Imaizumi, T., Miyagishi, M., Taira, K., Foy, E., Loo, Y. M., Gale, M., Jr., Akira, S., et al. (2005). Shared and Unique Functions of the DExD/H-Box Helicases RIG-I, MDA5, and LGP2 in Antiviral Innate Immunity. J Immunol 175, 2851-2858.

Yoneyama, M., M. Kikuchi, T. Natsukawa, N. Shinobu, T. Imaizumi, M. Miyagishi, K. Taira, S. Akira, and T. Fujita. 2004. The RNA helicase RIG-I has an essential function in double-stranded RNA-induced innate antiviral responses. Nat Immunol 5:730-737.

Zhou, T., J. D. Mountz, and R. P. Kimberly. 2002 Immunobiology of tumor necrosis factor receptor superfamily. Immunol Res 26:323-336.

Zhou, T., L. Song, P. Yang, Z. Wang, D. Lui, and R. S. Jope. 1999. Bisindolylmaleimide VIII facilitates Fas-mediated apoptosis and inhibits T cell-mediated autoimmune diseases. Nat Med 5:42-48.

Zhu, N., Ware, C. F., and Lai, M. M. (2001). Hepatitis C virus core protein enhances FADD-mediated apoptosis and suppresses TRADD signaling of tumor necrosis factor receptor. Virology 283, 178-187.

Zong, W. X., L. C. Edelstein, C. Chen, J. Bash, and C. Gelinas. 1999. The prosurvival Bcl-2 homolog Bfl-1/A1 is a direct transcriptional target of NF-kappaB that blocks TNFalpha-induced apoptosis. Genes Dev 13:382-387.

Zou, H., Y. Li, X. Liu, and X. Wang. 1999. An APAF-1.cytochrome c multimeric complex is a functional apoptosome that activates procaspase-9. J Biol Chem 274: 11549-11556.

What is claimed is:

1. A method of screening cancer cells from a subject with cancer for a biomarker of resistance to a death receptor 5 (DR5) agonist and treating the subject with cancer, comprising (a) monitoring the association of DR5 and a caspase-associated recruitment domain (CARD) containing protein, wherein the CARD-containing protein is DDX3 comprising amino acids 50-100 of SEQ ID NO:26 and wherein association signifies resistance to the DR5 agonist, and (b) administering to the subject lacking resistance to the DR5 agonist a therapeutic amount of the DR5 agonist.

2. The method of claim 1, further comprising pre-contacting the cell with the DR5 agonist.

3. The method of claim 1, wherein the subject has been treated with a DR5 antibody.

4. The method of claim 1, wherein the DR5 agonist is an antibody.

5. The method of claim 1, further comprising administering to the subject a therapeutic agent selected from the group consisting of chemotherapeutic agents, antibodies, members of the TNF family, anti-inflammatory agents, antibiotics, and immunosuppressives.

6. A method of screening cancer cells from a subject with cancer for a biomarker of resistance to a death receptor 5 (DR5) agonist and treating the subject with cancer, comprising (a) monitoring the association of DR5 and a caspase-associated recruitment domain (CARD) containing protein, wherein the CARD-containing protein is DDX3 comprising amino acids 50-100 of SEQ ID NO:26 and wherein association signifies resistance to the DR5 agonist, and (b) administering to the subject resistant to the DR5 agonist a therapeutic amount of the DR5 agonist and a modulator of one or more activities of the CARD containing protein that reduces resistance to the DR5 agonist, wherein the modulator is selected from the group consisting of Adriamycin, taxol, cisplatin and Bisindolymaleimide VIII (BisVIII).

7. The method of claim 6, further comprising pre-contacting the cell with the DR5 agonist.

8. The method of claim 6, wherein the subject has been treated with a DR5 antibody.

9. The method of claim 6, wherein the DR5 agonist is an antibody.

10. The method of claim 6, further comprising administering to the subject a therapeutic agent selected from the group consisting of chemotherapeutic agents, antibodies, members of the TNF family, anti-inflammatory agents, antibiotics, and immunosuppressives.

* * * * *

SEQUENCE LISTING

```
<160> NUMBER OF SEQ ID NOS: 46

<210> SEQ ID NO 1
<211> LENGTH: 17
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 1

His Val Ile Asn Phe Asp Leu Pro Ser Asp Ile Glu Glu Tyr Val His
 1               5                  10                  15

Arg


<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 2

Asp Phe Leu Asp Glu Tyr Ile Phe Leu Ala Val Gly Arg
 1               5                  10


<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 3
```

```
Asp Leu Leu Asp Leu Leu Val Glu Ala Lys
 1               5                  10


<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 4

Ser Phe Leu Leu Asp Leu Leu Asn Ala Thr Gly Lys
 1               5                  10


<210> SEQ ID NO 5
<211> LENGTH: 22
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 5

Thr Ala Ala Phe Leu Leu Pro Ile Leu Ser Gln Ile Tyr Ser Asp Gly
 1               5                  10                  15

Pro Gly Glu Ala Leu Arg
            20


<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 6

Gln Tyr Pro Ile Ser Leu Val Leu Ala Pro Thr
 1               5                  10


<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 7

Asp Glu Asp Asp
 1


<210> SEQ ID NO 8
<211> LENGTH: 62
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 8

caccaagctt gcgctatatt cctcctcatt tcgaaaaatg aggaggaata tagcgcctcg      60

ag                                                                     62


<210> SEQ ID NO 9
```

```
<211> LENGTH: 62
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 9

aaaactcgag gcgctatatt cctcctcatt tttcgaaatg aggaggaata tagcgcaagc     60

tt                                                                     62


<210> SEQ ID NO 10
<211> LENGTH: 50
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 10

caccggagaa attatcatgg gaaaccgaag tttcccatga taatttctcc                50


<210> SEQ ID NO 11
<211> LENGTH: 50
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 11

aaaaggagaa attatcatgg gaaacttcgg tttcccatga taatttctcc                50


<210> SEQ ID NO 12
<211> LENGTH: 50
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 12

caccgccaag tgatattgaa gaataaacgt attcttcaat atcacttggc                50


<210> SEQ ID NO 13
<211> LENGTH: 50
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 13

aaaagccaag tgatattgaa gaatacgttt attcttcaat atcacttggc                50


<210> SEQ ID NO 14
<211> LENGTH: 50
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 14

caccgctttc cagcgggtat attagcgaac taatataccc gctggaaagc                50
```

```
<210> SEQ ID NO 15
<211> LENGTH: 50
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 15

aaaagctttc cagcgggtat attagttcgc taatataccc gctggaaagc                50


<210> SEQ ID NO 16
<211> LENGTH: 50
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 16

caccgctgat cggatgttgg atatgcgaac atatccaaca tccgatcagc                50


<210> SEQ ID NO 17
<211> LENGTH: 50
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 17

aaaagctgat cggatgttgg atatgttcgc atatccaaca tccgatcagc                50


<210> SEQ ID NO 18
<211> LENGTH: 13
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 18

Ser Gly Ile His Ser Gly Ala Thr Thr Thr Ala Pro Ser
 1               5                   10


<210> SEQ ID NO 19
<211> LENGTH: 17
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 19

Ser Val Pro Pro Ser Pro Ser Gly Ser Gln Ala Ser Ser Pro Gln Ser
 1               5                   10                  15

Ser


<210> SEQ ID NO 20
<211> LENGTH: 21
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 20
```

```
Ser Ser Phe Gly Ser Arg Ser Asp Ser Arg Gly Lys Ser Ser Phe Phe
 1              5                   10                  15

Ser Asp Arg Gly Ser
            20


<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 21

Asp Glu Ala Asp
 1


<210> SEQ ID NO 22
<211> LENGTH: 440
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 22

Met Glu Gln Arg Gly Gln Asn Ala Pro Ala Ala Ser Gly Ala Arg Lys
 1              5                   10                  15

Arg His Gly Pro Gly Pro Arg Glu Ala Arg Gly Ala Arg Pro Gly Leu
            20                  25                  30

Arg Val Pro Lys Thr Leu Val Leu Val Val Ala Ala Val Leu Leu Leu
        35                  40                  45

Val Ser Ala Glu Ser Ala Leu Ile Thr Gln Gln Asp Leu Ala Pro Gln
    50                  55                  60

Gln Arg Val Ala Pro Gln Gln Lys Arg Ser Ser Pro Ser Glu Gly Leu
65                  70                  75                  80

Cys Pro Pro Gly His His Ile Ser Glu Asp Gly Arg Asp Cys Ile Ser
                85                  90                  95

Cys Lys Tyr Gly Gln Asp Tyr Ser Thr His Trp Asn Asp Leu Leu Phe
            100                 105                 110

Cys Leu Arg Cys Thr Arg Cys Asp Ser Gly Glu Val Glu Leu Ser Pro
        115                 120                 125

Cys Thr Thr Thr Arg Asn Thr Val Cys Gln Cys Glu Glu Gly Thr Phe
    130                 135                 140

Arg Glu Glu Asp Ser Pro Glu Met Cys Arg Lys Cys Arg Thr Gly Cys
145                 150                 155                 160

Pro Arg Gly Met Val Lys Val Gly Asp Cys Thr Pro Trp Ser Asp Ile
                165                 170                 175

Glu Cys Val His Lys Glu Ser Gly Thr Lys His Ser Gly Glu Ala Pro
            180                 185                 190

Ala Val Glu Glu Thr Val Thr Ser Ser Pro Gly Thr Pro Ala Ser Pro
        195                 200                 205

Cys Ser Leu Ser Gly Ile Ile Ile Gly Val Thr Val Ala Ala Val Val
    210                 215                 220

Leu Ile Val Ala Val Phe Val Cys Lys Ser Leu Leu Trp Lys Lys Val
225                 230                 235                 240

Leu Pro Tyr Leu Lys Gly Ile Cys Ser Gly Gly Gly Gly Asp Pro Glu
                245                 250                 255
```

```
Arg Val Asp Arg Ser Ser Gln Arg Pro Gly Ala Glu Asp Asn Val Leu
            260                 265                 270

Asn Glu Ile Val Ser Ile Leu Gln Pro Thr Gln Val Pro Glu Gln Glu
        275                 280                 285

Met Glu Val Gln Glu Pro Ala Glu Pro Thr Gly Val Asn Met Leu Ser
    290                 295                 300

Pro Gly Glu Ser Glu His Leu Leu Glu Pro Ala Glu Ala Glu Arg Ser
305                 310                 315                 320

Gln Arg Arg Arg Leu Leu Val Pro Ala Asn Glu Gly Asp Pro Thr Glu
                325                 330                 335

Thr Leu Arg Gln Cys Phe Asp Asp Phe Ala Asp Leu Val Pro Phe Asp
            340                 345                 350

Ser Trp Glu Pro Leu Met Arg Lys Leu Gly Leu Met Asp Asn Glu Ile
        355                 360                 365

Lys Val Ala Lys Ala Glu Ala Ala Gly His Arg Asp Thr Leu Tyr Thr
    370                 375                 380

Met Leu Ile Lys Trp Val Asn Lys Thr Gly Arg Asp Ala Ser Val His
385                 390                 395                 400

Thr Leu Leu Asp Ala Leu Glu Thr Leu Gly Glu Arg Leu Ala Lys Gln
                405                 410                 415

Lys Ile Glu Asp His Leu Leu Ser Ser Gly Lys Phe Met Tyr Leu Glu
            420                 425                 430

Gly Asn Ala Asp Ser Ala Met Ser
        435                 440


<210> SEQ ID NO 23
<211> LENGTH: 90
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 23

Gly Gly Gly Gly Asp Pro Glu Arg Val Asp Arg Ser Ser Gln Arg Pro
 1               5                  10                  15

Gly Ala Glu Asp Asn Val Leu Asn Glu Ile Val Ser Ile Leu Gln Pro
            20                  25                  30

Thr Gln Val Pro Glu Gln Glu Met Glu Val Gln Glu Pro Ala Glu Pro
        35                  40                  45

Thr Gly Val Asn Met Leu Ser Pro Gly Glu Ser Glu His Leu Leu Glu
    50                  55                  60

Pro Ala Glu Ala Glu Arg Ser Gln Arg Arg Arg Leu Leu Val Pro Ala
65                  70                  75                  80

Asn Gly Asp Pro Thr Glu Thr Leu Arg Gln
                85                  90


<210> SEQ ID NO 24
<211> LENGTH: 30
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 24

Gln Pro Thr Gln Val Pro Glu Gln Glu Met Glu Val Gln Glu Pro Ala
 1               5                  10                  15
```

```
Glu Pro Thr Gly Val Asn Met Leu Ser Pro Gly Glu Ser Glu
            20                  25                  30


<210> SEQ ID NO 25
<211> LENGTH: 3408
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 25

ctttcccctt actccgctcc cctcttttcc ctccctctcc tccccttccc tctgttctct     60

cctcctcttc ccctcccctc ccccgtccgg ggcactctat attcaagcca ccgtttcctg    120

cttcacaaaa tggccaccgc acgcgacacc tacggtcacg tggcctgccg ccctctcagt    180

ttcgggaatc tgcctagctc ccactaaggg gaggctaccc gcggaagagc gagggcagat    240

tagaccggag aaatcccacc acatctccaa gcccgggaac tgagagagga agaagagtga    300

aggccagtgt taggaaaaaa aaaaacaaaa acaaaaaaaa cgaaaaacga aagctgagtg    360

catagagttg gaaaggggag cgaatgcgta aggttggaaa ggggggcgaa gaggcctagg    420

ttaacatttt caggcgtctt agccggtgga aagcgggaga cgcaagttct cgcgagatct    480

cgagaactcc gaggctgaga ctagggtttt agcggagagc acgggaagtg tagctcgaga    540

gaactgggac agcatttcgc accctaagct ccaaggcagg actgctaggg gcgacaggac    600

taagtaggaa atcccttgag cttagacctg agggagcgcg cagtagccgg gcagaagtcg    660

ccgcgacagg gaattgcggt gtgagaggga gggcacacgt tgtacgtgct gacgtagccg    720

gctttccagc gggtatatta gatccgtggc cgcgcggtgc gctccagagc cgcagttctc    780

ccgtgagagg gccttcgcgg tggaacaaac actcgcttag cagcggaaga ctccgagttc    840

tcggtactct tcagggatga gtcatgtggc agtggaaaat gcgctcgggc tggaccagca    900

gtttgctggc ctagacctga actcttcaga taatcagagt ggaggaagta cagccagcaa    960

agggcgctat attcctcctc atttaaggaa ccgagaagct actagaggtt tctacgataa   1020

agacagttca gggtggagtt ctagcaaaga taaggatgcg tatagcagtt ttggatctcg   1080

tagtgattca agagggaagt ctagcttctt cagtgatcgt ggaagtggat caaggggaag   1140

gtttgatgat cgtggacgga gtgattacga tggcattggc agccgtggtg acagaagtgg   1200

ctttggcaaa tttgaacgtg gtggaaacag tcgctggtgt gacaaatcag atgaagatga   1260

ttggtcaaaa ccactcccac caagtgaacg cttggaacag gaactctttt ctggaggcaa   1320

cactgggatt aattttgaga aatacgatga cattccagtt gaggcaacag gcaacaactg   1380

tcctccacat attgaaagtt tcagtgatgt tgagatggga gaaattatca tgggaaacat   1440

tgagcttact cgttatactc gcccaactcc agtgcaaaag catgctattc ctattatcaa   1500

agagaaaaga gacttgatgg cttgtgccca aacagggtct ggaaaaactg cagcatttct   1560

gttgcccatc ttgagtcaga tttattcaga tggtccaggc gaggctttga gggccatgaa   1620

ggaaaatgga aggtatgggc gccgcaaaca atacccaatc tccttggtat tagcaccaac   1680

gagagagttg gcagtacaga tctacgaaga agccagaaaa ttttcatacc gatctagagt   1740

tcgtccttgc gtggtttatg gtggtgccga tattggtcag cagattcgag acttggaacg   1800

tggatgccat ttgttagtag ccactccagg acgtctagtg gatatgatgg aaagaggaaa   1860

gattggatta gacttttgca aatacttggt gttagatgaa gctgatcgga tgttggatat   1920

ggggtttgag cctcagattc gtagaatagt cgaacaagat actatgcctc caaagggtgt   1980
```

```
ccgccacact atgatgttta gtgctacttt tcctaaggaa atacagatgc tggctcgtga   2040

tttcttagat gaatatatct tcttggctgt aggaagagtt ggctctacct ctgaaaacat   2100

cacacagaaa gtagtttggg tggaagaatc agacaaacgg tcatttctgc ttgacctcct   2160

aaatgcaaca ggcaaggatt cactgacctt agtgtttgtg gagaccaaaa agggtgcaga   2220

ttctctggag gatttcttat accatgaagg atacgcatgt accagcatcc atggagaccg   2280

ttctcagagg gatagagaag aggcccttca ccagttccgc tcaggaaaaa gcccaatttt   2340

agtggctaca gcagtagcag caagaggact ggacatttca aatgtgaaac atgttatcaa   2400

ttttgacttg ccaagtgata ttgaagaata tgtacatcgt attggtcgta cgggacgtgt   2460

aggaaacctt ggcctggcaa cctcattctt taacgagagg aacataaata ttactaagga   2520

tttgttggat cttcttgttg aagctaaaca agaagtgccg tcttggttag aaaacatggc   2580

ttatgaacac cactacaagg gtagcagtcg tggacgttct aagagtagca gatttagtgg   2640

agggtttggt gccagagact accgacaaag tagcggtgcc agcagttcca gcttcagcag   2700

cagccgcgca agcagcagcc gcagtggcgg aggtggccac ggtagcagca gaggatttgg   2760

tggaggtggc tatggaggct tttacaacag tgatggatat ggaggaaatt ataactccca   2820

gggggttgac tggtggggta actgagcctg ctttgcagta ggtcaccctg ccaaacaagc   2880

taatatggaa accacatgta acttagccag actatacctt gtgtagtttc aagaactcgc   2940

agtacattac cagctgtgat tctccactga aattttttt ttaagggagc tcaaggtcac   3000

aagaagaaat gaaaggaaca atcagcagcc ctgttcagaa ggatcatgct catctgtgga   3060

gcaagtgccc ccatgaaatg ccatattttg tgaagaaagt gcatgcagga atattcaggg   3120

agtccagcat gtagtcatgg cagccttagg tatttgagac cgaccaaccc tcctgatgaa   3180

gacaaccata actcatgcag aacttggagc gtgatgccca gaagtgtgtg aactggtctg   3240

tgaccacaaa gatgagaacc gcatgctgag attggtggaa tggagatttc agtgagccta   3300

catgcagatg acatggtgac acccgtgccc agcctgagct gttttcttct ggccctctta   3360

ttacatgaga aaaataaaca cctatgcacc ttggcctcaa aaaaaaaa                3408
```

<210> SEQ ID NO 26
<211> LENGTH: 662
<212> TYPE: PRT
<213> ORGANISM: Artificial Sequence
<220> FEATURE:
<223> OTHER INFORMATION: Description of Artificial Sequence; note = synthetic construct

<400> SEQUENCE: 26

```
Met Ser His Val Ala Val Glu Asn Ala Leu Gly Leu Asp Gln Gln Phe
 1               5                  10                  15

Ala Gly Leu Asp Leu Asn Ser Ser Asp Asn Gln Ser Gly Gly Ser Thr
            20                  25                  30

Ala Ser Lys Gly Arg Tyr Ile Pro Pro His Leu Arg Asn Arg Glu Ala
        35                  40                  45

Thr Arg Gly Phe Tyr Asp Lys Asp Ser Ser Gly Trp Ser Ser Ser Lys
    50                  55                  60

Asp Lys Asp Ala Tyr Ser Ser Phe Gly Ser Arg Ser Asp Ser Arg Gly
65                  70                  75                  80

Lys Ser Ser Phe Phe Ser Asp Arg Gly Ser Gly Ser Arg Gly Arg Phe
                85                  90                  95

Asp Asp Arg Gly Arg Ser Asp Tyr Asp Gly Ile Gly Ser Arg Gly Asp
```

```
            100                 105                 110

Arg Ser Gly Phe Gly Lys Phe Glu Arg Gly Gly Asn Ser Arg Trp Cys
        115                 120                 125

Asp Lys Ser Asp Glu Asp Asp Trp Ser Lys Pro Leu Pro Pro Ser Glu
    130                 135                 140

Arg Leu Glu Gln Glu Leu Phe Ser Gly Gly Asn Thr Gly Ile Asn Phe
145                 150                 155                 160

Glu Lys Tyr Asp Asp Ile Pro Val Glu Ala Thr Gly Asn Asn Cys Pro
                165                 170                 175

Pro His Ile Glu Ser Phe Ser Asp Val Glu Met Gly Glu Ile Ile Met
            180                 185                 190

Gly Asn Ile Glu Leu Thr Arg Tyr Thr Arg Pro Thr Pro Val Gln Lys
        195                 200                 205

His Ala Ile Pro Ile Ile Lys Glu Lys Arg Asp Leu Met Ala Cys Ala
    210                 215                 220

Gln Thr Gly Ser Gly Lys Thr Ala Ala Phe Leu Leu Pro Ile Leu Ser
225                 230                 235                 240

Gln Ile Tyr Ser Asp Gly Pro Gly Glu Ala Leu Arg Ala Met Lys Glu
                245                 250                 255

Asn Gly Arg Tyr Gly Arg Arg Lys Gln Tyr Pro Ile Ser Leu Val Leu
            260                 265                 270

Ala Pro Thr Arg Glu Leu Ala Val Gln Ile Tyr Glu Glu Ala Arg Lys
        275                 280                 285

Phe Ser Tyr Arg Ser Arg Val Arg Pro Cys Val Val Tyr Gly Gly Ala
    290                 295                 300

Asp Ile Gly Gln Gln Ile Arg Asp Leu Glu Arg Gly Cys His Leu Leu
305                 310                 315                 320

Val Ala Thr Pro Gly Arg Leu Val Asp Met Met Glu Arg Gly Lys Ile
                325                 330                 335

Gly Leu Asp Phe Cys Lys Tyr Leu Val Leu Asp Glu Ala Asp Arg Met
            340                 345                 350

Leu Asp Met Gly Phe Glu Pro Gln Ile Arg Arg Ile Val Glu Gln Asp
        355                 360                 365

Thr Met Pro Pro Lys Gly Val Arg His Thr Met Met Phe Ser Ala Thr
    370                 375                 380

Phe Pro Lys Glu Ile Gln Met Leu Ala Arg Asp Phe Leu Asp Glu Tyr
385                 390                 395                 400

Ile Phe Leu Ala Val Gly Arg Val Gly Ser Thr Ser Glu Asn Ile Thr
                405                 410                 415

Gln Lys Val Val Trp Val Glu Glu Ser Asp Lys Arg Ser Phe Leu Leu
            420                 425                 430

Asp Leu Leu Asn Ala Thr Gly Lys Asp Ser Leu Thr Leu Val Phe Val
        435                 440                 445

Glu Thr Lys Lys Gly Ala Asp Ser Leu Glu Asp Phe Leu Tyr His Glu
    450                 455                 460

Gly Tyr Ala Cys Thr Ser Ile His Gly Asp Arg Ser Gln Arg Asp Arg
465                 470                 475                 480

Glu Glu Ala Leu His Gln Phe Arg Ser Gly Lys Ser Pro Ile Leu Val
                485                 490                 495

Ala Thr Ala Val Ala Ala Arg Gly Leu Asp Ile Ser Asn Val Lys His
            500                 505                 510

Val Ile Asn Phe Asp Leu Pro Ser Asp Ile Glu Glu Tyr Val His Arg
        515                 520                 525
```

```
Ile Gly Arg Thr Gly Arg Val Gly Asn Leu Gly Leu Ala Thr Ser Phe
    530                 535                 540

Phe Asn Glu Arg Asn Ile Asn Ile Thr Lys Asp Leu Leu Asp Leu Leu
545                 550                 555                 560

Val Glu Ala Lys Gln Glu Val Pro Ser Trp Leu Glu Asn Met Ala Tyr
                565                 570                 575

Glu His His Tyr Lys Gly Ser Ser Arg Gly Arg Ser Lys Ser Ser Arg
            580                 585                 590

Phe Ser Gly Gly Phe Gly Ala Arg Asp Tyr Arg Gln Ser Ser Gly Ala
        595                 600                 605

Ser Ser Ser Ser Phe Ser Ser Ser Arg Ala Ser Ser Ser Arg Ser Gly
    610                 615                 620

Gly Gly Gly His Gly Ser Ser Arg Gly Phe Gly Gly Gly Gly Tyr Gly
625                 630                 635                 640

Gly Phe Tyr Asn Ser Asp Gly Tyr Gly Gly Asn Tyr Asn Ser Gln Gly
                645                 650                 655

Val Asp Trp Trp Gly Asn
            660


<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 27

ggagaaatta tcatgggaaa c                                                21


<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 28

guuucccaug auaauuucuc c                                                21


<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 29

acggatccaa atgagtcatg tggcagtgga                                       30


<210> SEQ ID NO 30
<211> LENGTH: 28
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 30

ctctcgagca aagcaggctc agttaccc                                         28
```

<210> SEQ ID NO 31
<211> LENGTH: 31
<212> TYPE: DNA
<213> ORGANISM: Artificial Sequence
<220> FEATURE:
<223> OTHER INFORMATION: Description of Artificial Sequence; note = synthetic construct

<400> SEQUENCE: 31
aaaggtacca gccatggaac aacggggaca g 31

<210> SEQ ID NO 32
<211> LENGTH: 33
<212> TYPE: DNA
<213> ORGANISM: Artificial Sequence
<220> FEATURE:
<223> OTHER INFORMATION: Description of Artificial Sequence; note = synthetic construct

<400> SEQUENCE: 32
aaagatatct taggacatgg cagagtctgc att 33

<210> SEQ ID NO 33
<211> LENGTH: 34
<212> TYPE: DNA
<213> ORGANISM: Artificial Sequence
<220> FEATURE:
<223> OTHER INFORMATION: Description of Artificial Sequence; note = synthetic construct

<400> SEQUENCE: 33
acggatccaa atgttttctg gaggcaacac tggg 34

<210> SEQ ID NO 34
<211> LENGTH: 36
<212> TYPE: DNA
<213> ORGANISM: Artificial Sequence
<220> FEATURE:
<223> OTHER INFORMATION: Description of Artificial Sequence; note = synthetic construct

<400> SEQUENCE: 34
aaagatatct tactgtctca gagtctcagt gggatc 36

<210> SEQ ID NO 35
<211> LENGTH: 36
<212> TYPE: DNA
<213> ORGANISM: Artificial Sequence
<220> FEATURE:
<223> OTHER INFORMATION: Description of Artificial Sequence; note = synthetic construct

<400> SEQUENCE: 35
aaagatatcc tcgagatttg ctggaaccag cagcct 36

<210> SEQ ID NO 36
<211> LENGTH: 31
<212> TYPE: PRT
<213> ORGANISM: Artificial Sequence
<220> FEATURE:
<223> OTHER INFORMATION: Description of Artificial Sequence; note = synthetic construct

<400> SEQUENCE: 36

Val Asn Met Leu Ser Pro Gly Glu Ser Glu His Leu Leu Glu Pro Ala
1 5 10 15

```
Glu Ala Glu Arg Ser Gln Arg Arg Arg Leu Leu Val Pro Ala Asn
            20                  25                  30


<210> SEQ ID NO 37
<211> LENGTH: 51
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 37

Tyr Thr Arg Pro Thr Pro Val Gln Lys His Ala Ile Pro Ile Ile Lys
 1               5                  10                  15

Glu Lys Arg Asp Leu Met Ala Cys Ala Gln Thr Gly Ser Gly Lys Thr
            20                  25                  30

Ala Ala Phe Leu Leu Pro Ile Leu Ser Gln Ile Tyr Ser Asp Gly Pro
        35                  40                  45

Gly Glu Ala
    50


<210> SEQ ID NO 38
<211> LENGTH: 51
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 38

Val Tyr Gly Gly Ala Asp Ile Gly Gln Gln Ile Arg Asp Leu Glu Arg
 1               5                  10                  15

Gly Cys His Leu Leu Val Ala Thr Pro Gly Arg Leu Val Asp Met Met
            20                  25                  30

Glu Arg Gly Lys Ile Gly Leu Asp Phe Cys Lys Tyr Leu Val Leu Asp
        35                  40                  45

Glu Ala Asp
    50


<210> SEQ ID NO 39
<211> LENGTH: 512
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 39

Phe Ser Gly Gly Asn Thr Gly Ile Asn Phe Glu Lys Tyr Asp Asp Ile
 1               5                  10                  15

Pro Val Glu Ala Thr Gly Asn Asn Cys Pro Pro His Ile Glu Ser Phe
            20                  25                  30

Ser Asp Val Glu Met Gly Glu Ile Ile Met Gly Asn Ile Glu Leu Thr
        35                  40                  45

Arg Tyr Thr Arg Pro Thr Pro Val Gln Lys His Ala Ile Pro Ile Ile
    50                  55                  60

Lys Glu Lys Arg Asp Leu Met Ala Cys Ala Gln Thr Gly Ser Gly Lys
65                  70                  75                  80

Thr Ala Ala Phe Leu Leu Pro Ile Leu Ser Gln Ile Tyr Ser Asp Gly
                85                  90                  95
```

```
Pro Gly Glu Ala Leu Arg Ala Met Lys Glu Asn Gly Arg Tyr Gly Arg
            100                 105                 110

Arg Lys Gln Tyr Pro Ile Ser Leu Val Leu Ala Pro Thr Arg Glu Leu
        115                 120                 125

Ala Val Gln Ile Tyr Glu Glu Ala Arg Lys Phe Ser Tyr Arg Ser Arg
    130                 135                 140

Val Arg Pro Cys Val Val Tyr Gly Gly Ala Asp Ile Gly Gln Gln Ile
145                 150                 155                 160

Arg Asp Leu Glu Arg Gly Cys His Leu Leu Val Ala Thr Pro Gly Arg
                165                 170                 175

Leu Val Asp Met Met Glu Arg Gly Lys Ile Gly Leu Asp Phe Cys Lys
            180                 185                 190

Tyr Leu Val Leu Asp Glu Ala Asp Arg Met Leu Asp Met Gly Phe Glu
        195                 200                 205

Pro Gln Ile Arg Arg Ile Val Glu Gln Asp Thr Met Pro Pro Lys Gly
    210                 215                 220

Val Arg His Thr Met Met Phe Ser Ala Thr Phe Pro Lys Glu Ile Gln
225                 230                 235                 240

Met Leu Ala Arg Asp Phe Leu Asp Glu Tyr Ile Phe Leu Ala Val Gly
                245                 250                 255

Arg Val Gly Ser Thr Ser Glu Asn Ile Thr Gln Lys Val Val Trp Val
            260                 265                 270

Glu Glu Ser Asp Lys Arg Ser Phe Leu Leu Asp Leu Leu Asn Ala Thr
        275                 280                 285

Gly Lys Asp Ser Leu Thr Leu Val Phe Val Glu Thr Lys Lys Gly Ala
    290                 295                 300

Asp Ser Leu Glu Asp Phe Leu Tyr His Glu Gly Tyr Ala Cys Thr Ser
305                 310                 315                 320

Ile His Gly Asp Arg Ser Gln Arg Asp Arg Glu Glu Ala Leu His Gln
                325                 330                 335

Phe Arg Ser Gly Lys Ser Pro Ile Leu Val Ala Thr Ala Val Ala Ala
            340                 345                 350

Arg Gly Leu Asp Ile Ser Asn Val Lys His Val Ile Asn Phe Asp Leu
        355                 360                 365

Pro Ser Asp Ile Glu Glu Tyr Val His Arg Ile Gly Arg Thr Gly Arg
    370                 375                 380

Val Gly Asn Leu Gly Leu Ala Thr Ser Phe Phe Asn Glu Arg Asn Ile
385                 390                 395                 400

Asn Ile Thr Lys Asp Leu Leu Asp Leu Leu Val Glu Ala Lys Gln Glu
                405                 410                 415

Val Pro Ser Trp Leu Glu Asn Met Ala Tyr Glu His His Tyr Lys Gly
            420                 425                 430

Ser Ser Arg Gly Arg Ser Lys Ser Ser Arg Phe Ser Gly Gly Phe Gly
        435                 440                 445

Ala Arg Asp Tyr Arg Gln Ser Ser Gly Ala Ser Ser Ser Ser Phe Ser
    450                 455                 460

Ser Ser Arg Ala Ser Ser Ser Arg Ser Gly Gly Gly Gly His Gly Ser
465                 470                 475                 480

Ser Arg Gly Phe Gly Gly Gly Gly Tyr Gly Gly Phe Tyr Asn Ser Asp
                485                 490                 495

Gly Tyr Gly Gly Asn Tyr Asn Ser Gln Gly Val Asp Trp Trp Gly Asn
            500                 505                 510
```

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence; note = synthetic construct

<400> SEQUENCE: 40

Val Asp Val Ala Asp
1 5

<210> SEQ ID NO 41
<211> LENGTH: 4
<212> TYPE: PRT
<213> ORGANISM: Artificial Sequence
<220> FEATURE:
<223> OTHER INFORMATION: Description of Artificial Sequence; note = synthetic construct

<400> SEQUENCE: 41

Asp Glu Val Asp
1

<210> SEQ ID NO 42
<211> LENGTH: 4
<212> TYPE: PRT
<213> ORGANISM: Artificial Sequence
<220> FEATURE:
<223> OTHER INFORMATION: Description of Artificial Sequence; note = synthetic construct

<400> SEQUENCE: 42

Ile Glu Thr Asp
1

<210> SEQ ID NO 43
<211> LENGTH: 27
<212> TYPE: PRT
<213> ORGANISM: Artificial Sequence
<220> FEATURE:
<223> OTHER INFORMATION: Description of Artificial Sequence; note = synthetic construct

<400> SEQUENCE: 43

Ser Pro Gly Glu Ser Glu His Leu Leu Glu Pro Ala Glu Ala Glu Arg
1 5 10 15

Ser Gln Arg Arg Arg Leu Leu Val Pro Ala Asn
20 25

<210> SEQ ID NO 44
<211> LENGTH: 27
<212> TYPE: PRT
<213> ORGANISM: Artificial Sequence
<220> FEATURE:
<223> OTHER INFORMATION: Description of Artificial Sequence; note = synthetic construct

<400> SEQUENCE: 44

Ser Pro Glu Glu Pro Gln Arg Leu Leu Glu Gln Ala Glu Ala Glu Gly
1 5 10 15

Cys Gln Arg Arg Arg Leu Leu Val Pro Val Asn
20 25

<210> SEQ ID NO 45
<211> LENGTH: 27
<212> TYPE: PRT

-continued

```
<213> ORGANISM: Artificial Sequence
<220> FEATURE:
<223> OTHER INFORMATION: Description of Artificial Sequence; note =
      synthetic construct

<400> SEQUENCE: 45

Ser Pro Gly Glu Ala Gln Cys Leu Leu Gly Pro Ala Glu Ala Glu Gly
 1              5                   10                  15

Ser Gln Arg Arg Arg Leu Leu Val Pro Ala Asn
            20                  25


<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 46

Asp Lys Ser Asp Glu Asp Asp
 1              5
```